(12) United States Patent
Beria et al.

(10) Patent No.: US 10,071,074 B2
(45) Date of Patent: *Sep. 11, 2018

(54) THIENO-INDOLE MOIETIES AND METHODS OF TREATING USING THE SAME

(71) Applicant: NERVIANO MEDICAL SCIENCES S.R.L., Nerviano (MI) (IT)

(72) Inventors: Italo Beria, Nerviano (IT); Michele Caruso, Milan (IT); Vittoria Lupi, Milan (IT); Paolo Orsini, Legnano (IT); Matteo Salsa, Bellinzago Novarese (IT); Achille Panzeri, Merate (IT)

(73) Assignee: NERVIANO MEDICAL SCIENCES S.R.L., Nerviano (IT)

(*) Notice: Subject to any disclaimer, the term of this patent is extended or adjusted under 35 U.S.C. 154(b) by 0 days.

This patent is subject to a terminal disclaimer.

(21) Appl. No.: 15/359,703

(22) Filed: Nov. 23, 2016

(65) Prior Publication Data

US 2017/0071907 A1    Mar. 16, 2017

Related U.S. Application Data

(62) Division of application No. 14/390,644, filed as application No. PCT/EP2013/056743 on Mar. 28, 2013, now Pat. No. 9,527,863.

(30) Foreign Application Priority Data

Apr. 5, 2012 (EP) .................................... 12163459
Jul. 12, 2012 (EP) .................................... 12176162

(51) Int. Cl.
*A61K 31/407* (2006.01)
*A61K 31/496* (2006.01)
(Continued)

(52) U.S. Cl.
CPC .......... *A61K 31/407* (2013.01); *A61K 31/496* (2013.01); *A61K 38/05* (2013.01);
(Continued)

(58) Field of Classification Search
None
See application file for complete search history.

(56) References Cited

U.S. PATENT DOCUMENTS 5,659,022 A    8/1997   Kutyavin et al.
6,566,336 B1   5/2003   Sugiyama et al.
2015/0051154 A1 2/2015 Beria et al.

FOREIGN PATENT DOCUMENTS

GB     2 344 818 A     6/2000
JP     60-193989       10/1985
(Continued)

OTHER PUBLICATIONS

Baird R. et al., "Neighboring Carbon and Hydrogen. LI. Dienones from Arl o-3 Participation. Isolation and Behavior of Spiro (2,5)Octa-1, 4-Diene-3-One", Department of Chemistry 85:567-578 (Mar. 5, 1963).
(Continued)

*Primary Examiner* — Valerie Rodriguez-Garcia
(74) *Attorney, Agent, or Firm* — Scully, Scott, Murphy & Presser, P.C.

(57) ABSTRACT

The present invention relates to a novel class of alkylating agents comprising a thieno-indole moiety linked to a DNA-binding moiety, which have cytotoxic activity and are useful in treating diseases such as cancer, cellular proliferation disorders and viral infections. The present invention also provides methods for preparing these compounds, pharmaceutical compositions comprising them and methods of treating diseases utilizing such compounds or the pharma-
(Continued)

ceutical composition containing them. The invention also relates to the use of this novel class of alkylating agents in the preparation of conjugates. The present invention also relates to methods of treating ovarian cancer by administration of compounds of formula (II):

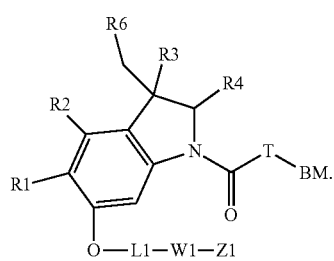

(II)

3 Claims, 4 Drawing Sheets

(51) Int. Cl.
    A61K 38/05    (2006.01)
    A61K 38/06    (2006.01)
    A61K 45/06    (2006.01)
    C07D 495/04   (2006.01)
    C07K 5/062    (2006.01)
    C07K 5/083    (2006.01)
    A61K 47/54    (2017.01)

(52) U.S. Cl.
    CPC .............. A61K 38/06 (2013.01); A61K 45/06
           (2013.01); A61K 47/545 (2017.08); C07D
           495/04 (2013.01); C07K 5/06017 (2013.01);
                                  C07K 5/0804 (2013.01)

(56) References Cited

FOREIGN PATENT DOCUMENTS

| JP | 2005-502703 A | 1/2005 |
|---|---|---|
| JP | 2005-532287 A | 10/2005 |
| JP | 2007-538099 A | 12/2007 |
| JP | 2009-525322 A | 7/2009 |
| WO | 00/15641 A1 | 3/2000 |
| WO | WO 02/083180 A1 | 10/2002 |
| WO | 02/096910 A1 | 12/2002 |
| WO | WO 2004/043493 A1 | 5/2004 |
| WO | 2004/069201 A2 | 8/2004 |
| WO | WO 2005/079398 A2 | 9/2005 |
| WO | WO 2005/105154 A1 | 11/2005 |
| WO | WO 2005/112919 A2 | 12/2005 |
| WO | WO 2006/012527 A1 | 2/2006 |
| WO | WO 2010/009124 A2 | 1/2010 |
| WO | 2013/149946 A1 | 10/2013 |

OTHER PUBLICATIONS

Beria I. et al., "Cytotoxic a-Halogenoacrylic Derivatives of Distamycin A and Congeners", Journal of Medicinal Chemistry 47(10):2611-2623 (2004).
Boger D.L. et al., "Enantioselective Total Synthesis of (+)-Duocarmycin A, epi-(+)-Duocarmycin A, and Their Unnatural Enantiomers", J. Am. Chem. Soc. 118(9):2301-2302 (1996).
Colombo M. et al., "A Fully Automated Method for Accurate Mass Determination Using High-Performance Liquid Chromatography With a Quadrupole/Orthogonal Acceleration Time-of-Flight Mass Spectrometer", Rapid Communications in Mass Spectrometry 18:511-517 (2004).
Greenwald R.B. et al., "Effective Drug Delivery by PEGylated Drug Conjugates", Advanced Drug Delivery Reviews 55:217-250 (2003).
Jeffrey S.C. et al., "Design, Synthesis, and In Vitro Evaluation of Dipeptide-Based Antibody Minor Groove Binder Conjugates", Journal of Medicinal Chemistry 48(5):1344-1358 (2005).
Kingsbury W.D. et al., "A Novel Peptide Delivery System Involving Peptidase Activated Prodrugs as Antimicrobial Agents. Synthesis and Biological Activity of Peptidyl Derivatives of 5-Fluorouracil", Journal of Medicinal Chemistry 27(11):1447-1451 (1984).
Tichenor M.S. et al., "Rational Design, Synthesis, and Evaluation of Key Analogues of CC-1065 and the Cuocarmycins", J. Am. Chem. Soc. 129(45):14092-14099 (2007).
Tranoy-Opalinski I. et al., "Design of Self-Immolative Linkers for Tumour-Activated Prodrug Therapy", Anti-Cancer Agents in Medicinal Chemistry 8(6):618-637 (2008).
Wang Y. et al., "CC-1065 Analogues Bearing Different DNA-Binding Subunits: Synthesis, Antitumour, and Preliminary Toxicity Study", Journal of Medicinal Chemistry 46:634-637 (2003).
Zhao R.Y. et al., "Synthesis and Biological Evaluation of Antibody Conjugates of Phosphate Prodrugs of Cytotoxic DNA Alkylators for the Targeted Treatment of Cancer", Journal of Medicinal Chemistry 55:766-782 (2012).
International Search Report dated Jun. 19, 2013 received from International Application No. PCT/EP2013/056743.
Database Registry, RN 1028273-07-05, retrieved from STN International [online]; retrieved on Oct. 21, 2016 (2008).
European Office Action dated Nov. 27, 2015 received in European Patent Application No. 13 715 931.5.
English-language translation of Japanese Notice of Rejection dated Nov. 1, 2016 received in Japanese Patent Application No. 2015-503835.

THIENO-INDOLE MOIETIES AND METHODS OF TREATING USING THE SAME

CROSS REFERENCE TO RELATED APPLICATIONS

The present application is a divisional of co-pending application having U.S. Ser. No. 14/390,644, filed on Oct. 3, 2014, which is a 371 of International Application having Serial No. PCT/EP2013/056743, filed on Mar. 28, 2013, which claims priority of European Patent Application No. 12176162.1, filed on Jul. 12, 2012 and European Patent Application No. 12163459.6, filed on Apr. 5, 2012, which the contents of all of which are incorporated herein by reference.

The present invention relates to a novel class of alkylating agents comprising a thieno-indole moiety linked to a DNA-binding moiety, methods for their preparation, pharmaceutical composition containing them and use thereof in treating certain mammalian tumors.

A wide range of chemicals is now available to treat cancers. Despite the efforts in anticancer research, cancer remains a looming and elusive target, therefore there is still a need for new anticancer agents. Alkylating agents are cytotoxic agents that have been used for the treatment of cancer for over six decades, yet their repertoire continues to grow. These agents act during all phases of the cell cycle directly on DNA, causing DNA strand breaks, leading to abnormal base pairing, inhibition of cell division and eventually resulting in cell death.

The present invention provides a novel class of alkylating agents comprising a thieno-indole moiety linked to a DNA-binding moiety.

Thieno-indoles derivatives are described in GB2344818; some specific compounds of the aforementioned patent applications are excluded from the present general formula.

Accordingly, a first object of the present invention is to provide a compound of formula (I) or (II)

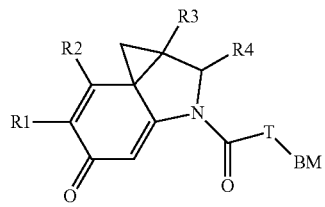

(I)

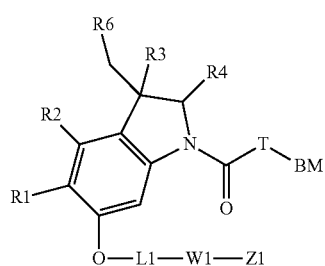

(II)

wherein R1 and R2 taken together form a group (D) or (G):

wherein R5 is hydrogen, linear or branched $C_1$-$C_4$ alkyl, linear or branched $C_1$-$C_4$ hydroxyalkyl or linear or branched $C_1$-$C_4$ aminoalkyl;

R3 and R4 are, each independently, hydrogen or a group selected from optionally substituted linear or branched $C_1$-$C_4$ alkyl and linear or branched $C_1$-$C_4$ hydroxyalkyl;

R6 is a leaving group;

T is null or N;

BM is a DNA binding moiety of formula (V):

(V)

wherein:

X is null, linear or branched $C_1$-$C_4$ alkyl, linear or branched $C_2$-$C_4$ alkenyl or linear or branched $C_2$-$C_4$ alkynyl;

Y and Y' are independently an optionally substituted aryl or heteroaryl;

U is a moiety of formula (VI) or (VII):

(VI)

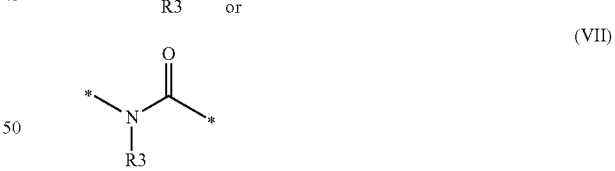

(VII)

wherein R3 is as defined above;

q is an integer from 0 to 4;

L1 is hydrogen or L, wherein L is null or a conditionally-cleavable moiety;

W1 is null or a self-immolative system comprising one or more self-immolative groups;

Z1 is null or a peptidic, non peptidic or hydrid peptidic and non peptidic linker; provided that a compound of formula (I) or a compound of formula (II) wherein L1 is hydrogen is excluded when 1) both T and X are null, q is 0 and Y' is an heterocycyl moiety of formula (VIII), (VIII)' or (VIII)":

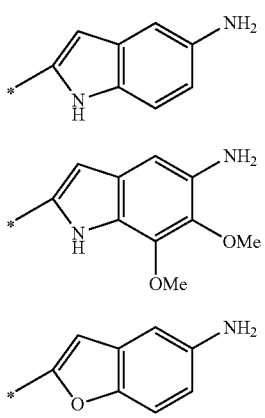

or
2) both T and X are null, q is 1, U is a group of formula (VII), Y is an heterocycyl moiety of formula (IX)

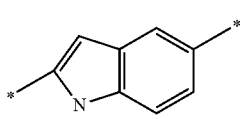

and
Y' is an heterocycyl moiety of formula III)'''

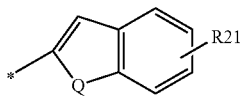

wherein Q is N or O, and R21 is hydrogen or a group selected from —N(C$_2$H$_5$)$_2$ and —C(NH)NH$_2$;
and
the pharmaceutically acceptable salts thereof.

Cytotoxic drugs act on rapidly proliferating cells with different mechanisms, usually by interfering directly or indirectly with DNA replication. Although this therapy resulted effective in different tumor types, it may suffer from some limitations: interfering with cell proliferation affects indeed also normal cells that proliferate frequently, such as bone marrow, cells of the gastrointestinal tract and hair follicles. Drug concentrations that would completely eradicate the tumor may not be reached because of dose-limiting side effects on these tissues leading immunosuppression, gastrointestinal tract toxicity and hair loss.

In addition cytotoxic drugs show in some cases non optimal physicochemical properties and may lack of suitable pharmacokinetic properties limiting their use in patients.

Conjugation of cytotoxic drugs to molecules able to vehicle the drug and thus improving tumor targeting or able to modify its pharmacokinetic properties is one of the strategies that has been undertaken to solve the above mentioned issues. Different examples of conjugation of cytotoxic drugs with proteins, peptides or aptamer, polymers or nanoparticles allowing better target delivery, improving solubility and in some cases other pharmacokinetic properties such as increasing half life or local concentration of the drug and improving drug performances have been reported. As a matter of facts, the resultant conjugates have improved characteristics in term of solubility, permeability into the cell, in vivo therapeutic window, controlled release, ability to reach the target according to the nature of the specific molecule conjugated with the cytotoxic agent.

For this reason, there is an increasing demand for the development of functionalized cytotoxic agents suitable to be conjugated with different types of molecules.

The present invention also provides functionalized alkylating agents which, other than having cytotoxic activity, are also suitable to be conjugated with different types of nucleophiles.

Accordingly, a second object of the present invention is to provide a compound of formula (III) or (IV):

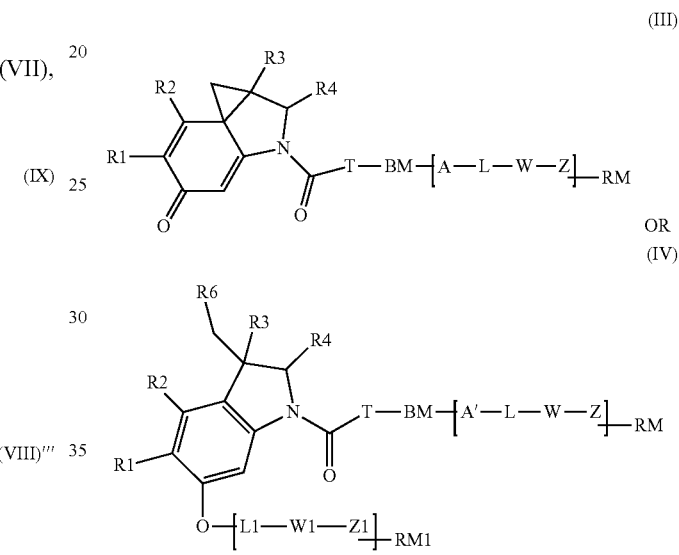

wherein
BM is a DNA binding moiety of formula (V)':

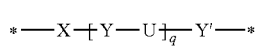

wherein:
X, Y, U, Y' and q are as defined above;
A is an atom selected from —O—, —NH—, —CO—;
A' is null or A, wherein A is as defined above;
L is null or a conditionally-cleavable moiety;
W is null or a self-immolative system comprising one or more self-immolative groups;
Z is null or a peptidic, non peptidic or hybrid peptidic and non peptidic linker;
RM is null or a reactive moiety attached to one or more of A, L, W or Z groups;
RM1 is null or a reactive moiety attached to one or more of L1, W1 or Z1 groups; and R1, R2, R3, R4, R6, T, BM, L1, W1 and Z1 are as defined above; provided that
1) a compound of formula (IV) is excluded when A' is null and RM1 is null;

2) a compound of formula (III) or (IV) is excluded when
a) both T and X are null, q is 0 and
   Y' is an heterocycyl moiety of formula (VIII)$^{IV}$

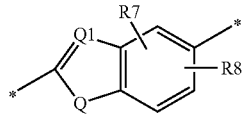

(VIII)$^{IV}$ wherein
Q is —O—, —S—, —NR14, wherein R14 is hydrogen, $C_1$-$C_4$ alkyl or $C_1$-$C_4$ hydroxyalkyl;
Q1 is —CH= or —N=;
R7 and R8 are independently hydrogen, halogen, hydroxy, $C_1$-$C_4$ alkoxy, cyano, —NCOOR3, —C(NH)—NH$_2$ or —NR3R4, wherein R3 and R4 are as defined above;
or
b) both T and X are null, q is 1 or 2, U is a group of formula (VII),
   Y is a heterocyclyl moiety of formula (IX)':

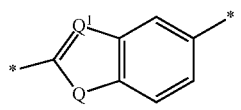

(IX)' and Y' is a heterocyclyl moiety of formula (VIII)$^{IV}$

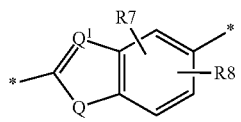

(VIII)$^{IV}$ wherein Q, Q1, R7 and R8 are as defined above;
and the pharmaceutically acceptable salts thereof.

It is noted that when L1 is hydrogen or a conditionally-cleavable moiety, and the 0-L1 bond is broken so generating a OH function, then the compounds of formula (II) or (IV) may be transformed in a compound of formula (I) or (III) respectively, through the well reviewed reaction mechanism reported in the literature (see e.g. Baiard, R; et al., *J. Am. Chem. Soc.* 1963, 85, 567-578; Zhao, R. Y. et al. *J. Med. Chem.* 2012, 55, 766-782.)

In addition, it is to be noted that a compound of formula (III) has one functionalization

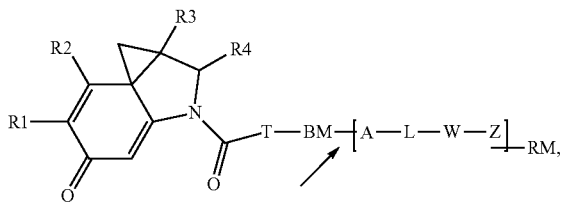

(III)

while a compound of formula (IV) may have one or two functionalization(s).

Specifically, a compound of formula (IV) has functionalization when:
   A' is A and L1 is hydrogen, as in a compound of formula (IV)'

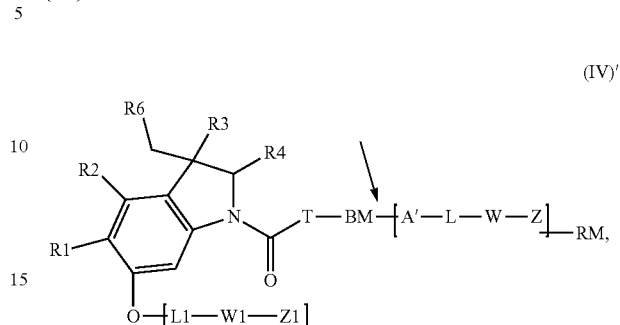

(IV)' or
   A' is null and L1 is not hydrogen, as in a compound of formula (IV)''', (IV)''' since L, W, Z and/or RM cannot be attached directly to BM.
A compound of formula (IV) has two functionalizations when
   A' is A and L1 is L, as in a compound of formula (IV)''

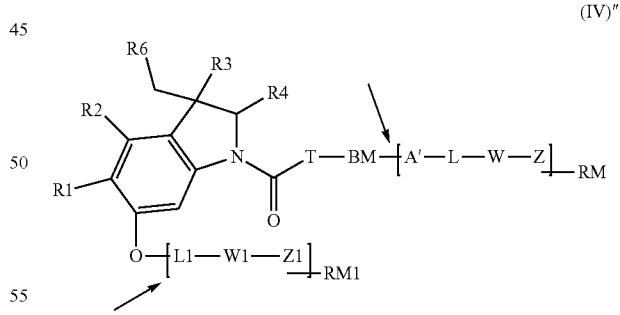

(IV)''

The present invention also provides methods of synthesizing the compounds of formula (I), (II), (III) and (IV), prepared through a process consisting of standard synthetic transformations and isomers, tautomers, hydrates, solvates, complexes, metabolites, prodrugs, carriers, N-oxides.

The present invention also provides a method for treating cancer, which comprises administering to a mammal, in need thereof, an effective amount of a compound of formula (I), (II), (III) or (IV) as defined above. The mammal in need thereof may be for example a human.

The present invention also provides a compound of formula (I), (II), (III) or (IV), as defined above, for use in a method of treating cancer, cellular proliferation disorders and viral infections.

Preferably, a compound of formula (I), (II), (III) or (IV), as defined above is for use in a method of treating specific types of cancers, including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukaemias, myelodysplastic syndrome and promyelocytic leukemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma and mesothelioma.

Furthermore, a compound of formula (I), (II), (III) or (IV), as defined above is for use in a method of treating specific cellular proliferation disorders such as, for example, benign prostate hyperplasia, familial adenomatosis polyposis (FAP), neurofibromatosis, psoriasis, vascular smooth cell proliferation associated with atherosclerosis, pulmonary fibrosis, arthritis, glomerulonephritis and post-surgical stenosis and restenosis.

In addition, a compound of formula (I), (II), (III) or (IV), as defined above is for use in a method of inhibiting tumor angiogenesis and metastasis, as well as in a method of treating organ transplant rejection and host versus graft disease.

The present invention also provides a pharmaceutical composition comprising a therapeutically effective amount of compounds of formula (I), (II), (III) or (IV) or a pharmaceutically acceptable salt thereof as defined above and at least one pharmaceutically acceptable excipient, carrier and/or diluent.

The present invention further provides a pharmaceutical composition comprising a compound of formula (I), (II), (III) or (IV) and one or more chemotherapeutic agents.

The present invention further provides a pharmaceutical composition comprising a compound of formula (I), (II), (III) or (IV) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix-metalloprotease inhibitors, telomerase inhibitors, tyrosine kinase inhibitors, anti-growth factor receptor agents, anti-HER2 agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product comprising a compound of formula (I), (II), (III), or (IV) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I), (II), (III) or (IV) or a pharmaceutically acceptable salt thereof, as defined above, for use as a medicament.

Moreover the invention provides the use of a compound of formula (I), (II), (III) or (IV) or a pharmaceutically acceptable salt thereof, as defined above, in the manufacture of a medicament with anticancer activity.

Finally, the invention provides the use of a compound of formula (I), (II), (III) or (IV) or a pharmaceutically acceptable salt thereof, as defined above, in the preparation of conjugates.

Unless stated otherwise, the following terms and phrases as used herein are intended to have the following meanings.

With the term "linear or branched $C_1$-$C_4$ alkyl" we intend any of the groups such as, for instance, methyl, ethyl, n-propyl, isopropyl, n-butyl, isobutyl, sec-butyl, tert-butyl.

With the term "linear or branched $C_1$-$C_4$ hydroxyalkyl" we intend any of the groups such as, for instance, 2-hydroxyethyl, 3-hydroxypropyl, 2-hydroxypropyl, 4-hydroxybutyl, 3-hydroxybutyl, 2-hydroxybutyl.

With the term "linear or branched $C_1$-$C_4$ alkoxy", we intend any of the groups such as, for instance, methoxy, ethoxy, propoxy, etc.

With the term "halogen" we intend a fluorine, chlorine, bromine or iodine.

With the term "linear or branched $C_1$-$C_4$ aminoalkyl" we intend any of the groups such as, for instance, 2-aminoethyl, 3-aminopropyl, 4-aminobutyl, 3-aminobutyl, etc.

The term "$C_3$-$C_8$ cycloalkyl" as used herein refers to a saturated or unsaturated non-aromatic all-carbon monocyclic ring, which may consist of one ring or two or more rings fused together. Examples include, but are not limited to, cyclopropyl, cyclobutyl, cyclopentyl, cyclopentenyl, cydopentadienyl, cyclohexyl, cyclohexenyl, 1,3-cyclohexadienyl, decalinyl, and 1,4-cyclohexadienyl.

The term "heterocyclyl" as used herein refers to a saturated or unsaturated non-aromatic $C_4$-$C_8$ carbocydic ring which may consist of one ring or two or more rings fused together, wherein from 1 to 4 carbon atoms are replaced by heteroatoms such as nitrogen, oxygen, sulfur, wherein said heteroatoms may be directly connected to each other; nitrogen and sulfur may optionally be oxidized and nitrogen may optionally be quaternized. Non limiting examples of heterocyclyl groups are, for instance, tetrahydrofuranyl, pyrrolidinyl, piperidinyl, 1,4-dioxanyl, decahydroquinolinyl, piperazinyl, oxazolidinyl and morpholinyl.

The term "aryl" as used herein refers to a mono-, bi- or poly-carbocyclic hydrocarbon from 1 to 4 ring systems, optionally further fused or linked to each other by single bonds, wherein at least one of the carbocyclic rings is aromatic, wherein the term "aromatic" refers to completely conjugated T-electron bond system. Non limiting examples of such aryl groups are phenyl, α- or β-naphthyl or anthracenyl groups.

The term "heteroaryl" as used herein refers to aromatic heterocyclic rings, typically 4- to 7-membered heterocycles, with from 1 to 4 heteroatoms selected among oxygen, nitrogen and sulfur, wherein nitrogen and sulfur may optionally be oxidized and nitrogen may optionally be quaternized; said heteroaryl ring can be optionally further fused or linked to one or two or more rings fused together, aromatic and non-aromatic carbocyclic and heterocylic rings. Heteroatoms may be directly connected to each other. Examples of heteroaryl groups include, but are not limited to, pyridinyl, pyrimidyl, furanyl, pyrrolyl, triazolyl, pyrazolyl, pyrazinyl, oxazolyl, isoxazolyl, thiazolyl, imidazolyl, thienyl, indolyl, benzofuranyl, benzimidazolyl, benzothiazolyl, purinyl, indazolyl, benzotriazolyl, benzisoxazolyl, quinoxalinyl, isoquinolyl, and quinolyl. In one embodiment, a heteroaryl group comprises from 1 to 4 heteroatoms. It should be noted that "$C_1$ heteroaryl group" denotes that there is only one carbon present in the ring system of the heteroaromatic group (carbon atoms in optional substituents are thus not counted). An example of such a heteroaromatic group is a tetrazolyl group.

The term "leaving group" refers to a group that can be substituted by another group in a substitution reaction. Such leaving groups are well-known in the art and examples include, but are not limited to, an halide (fluoride, chloride, bromide, and iodide), an azide, a sulfonate (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), succinimide-N-oxide, p-nitrophenoxide, pentafluorophenoxide, tetrafluorophenoxide, a carboxylate, an aminocarboxylate (carbamate) and an alkoxycarboxylate (carbonate). For substitutions at saturated carbon, halides and sulfonates are preferred leaving groups. For substitutions at a carbonyl carbon a halide, succinimide-N-oxide, p-nitrophenoxide, pentafluorophenoxide, tetrafluorophenoxide, a carboxylate, or an alkoxycarboxylate (carbonate) may for example be used as a leaving group. The term "leaving group" also refers to a group that is eliminated as a consequence of an elimination reaction, e.g., an electronic cascade reaction or a spirocyclization reaction. In this instance, an halide, a sulfonate, an azide, an aminocarboxylate (carbamate) or an alkoxycarboxylate (carbonate) may for example be used as a leaving group.

The term "active ester" refers to a functional group in which the alkoxy group of the ester moiety is a good leaving group. Examples of such alkoxy groups include, but are not limited to, succinimide-N-oxide, p-nitrophenoxide, pentafluorophenoxide, tetrafluorophenoxide, 1-hydroxybenzotriazole, and 1-hydroxy-7-azabenzotriazole, and groups with comparable leaving capability. Unsubstituted alkyl-based alkoxy groups such as methoxy, ethoxy, isopropoxy, and t-butoxy do not qualify as good leaving groups and methyl, ethyl, isopropyl, and t-butyl esters are therefore not considered to be active esters.

The term "nucleophiles" refers to molecules that bear a nucleophilic group. The term "nucleophilic group" refers to a species that donates an electron-pair to an electrophilic group to form a chemical bond in a chemical reaction. Examples of such nucleophilic groups include, but are not limited to halogens, amines, nitrites, azides, alcohols, alkoxyde anions, carboxylate anions, thiols, thiolates, etc.

The term "electrophilic group" refers to a species that accepts an electron-pair from a nucleophilic group to form a chemical bond in a chemical reaction. Examples of such electrophilic groups include, but are not limited to esters, aldehydes, amides, ketons, etc.

The term "alkylating moiety" refers to the structure that remain after breaking of one or more cleavable bonds and that may or may not be covalently bound to the nucleic acid strand.

The term "unnatural amino acid" refers to the D-stereoisomer of the naturally occurring amino acid.

Pharmaceutically acceptable salts of the compounds of formula (I), (II), (III) or (IV) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid.

Pharmaceutically acceptable salts of the compounds of formula (I), (II), (III) or (IV) also include the salts with inorganic or organic bases, e.g., alkali or alkaline-earth metals, especially sodium, potassium, calcium ammonium or magnesium hydroxides, carbonates or bicarbonates, acyclic or cyclic amines.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases when compounds can exist in tautomeric forms, each form is contemplated as being included within this invention whether existing in equilibrium or predominantly in one form.

The DNA-Binding Moiety BM

The BM moiety is a binding moiety that binds or associates the compound of formula (I), (II), (III) or (IV) with the double strand of the DNA. The binding moiety can improve affinity properties of the derivatives to the DNA or improve alkylating reactivity of the alkylating agent or target different sequences of the DNA so to modulate target specificity of the compounds.

Preferably, in a compound of formula (I) or (II) the BM moiety is a group of formula (V) as defined above, wherein X is null or a $C_2$-$C_4$ alkenyl of formula (XIV):

(XIV)

wherein R3, independently the same or different, is as define above;

U and q are as defined above;

Y, if present, is a group selected from:

(XVa)

(XVb)

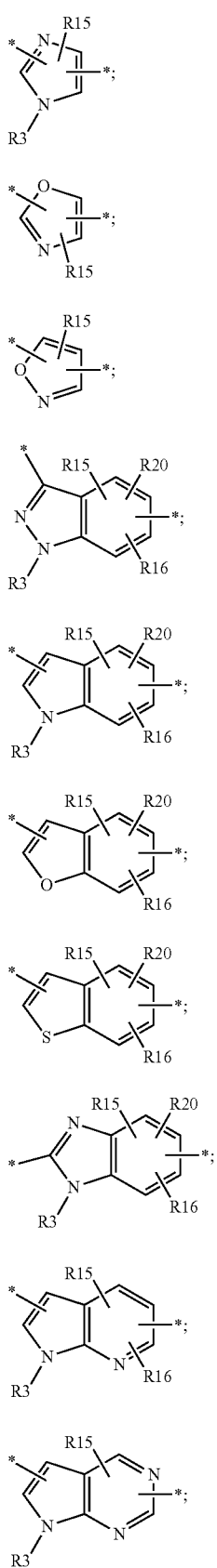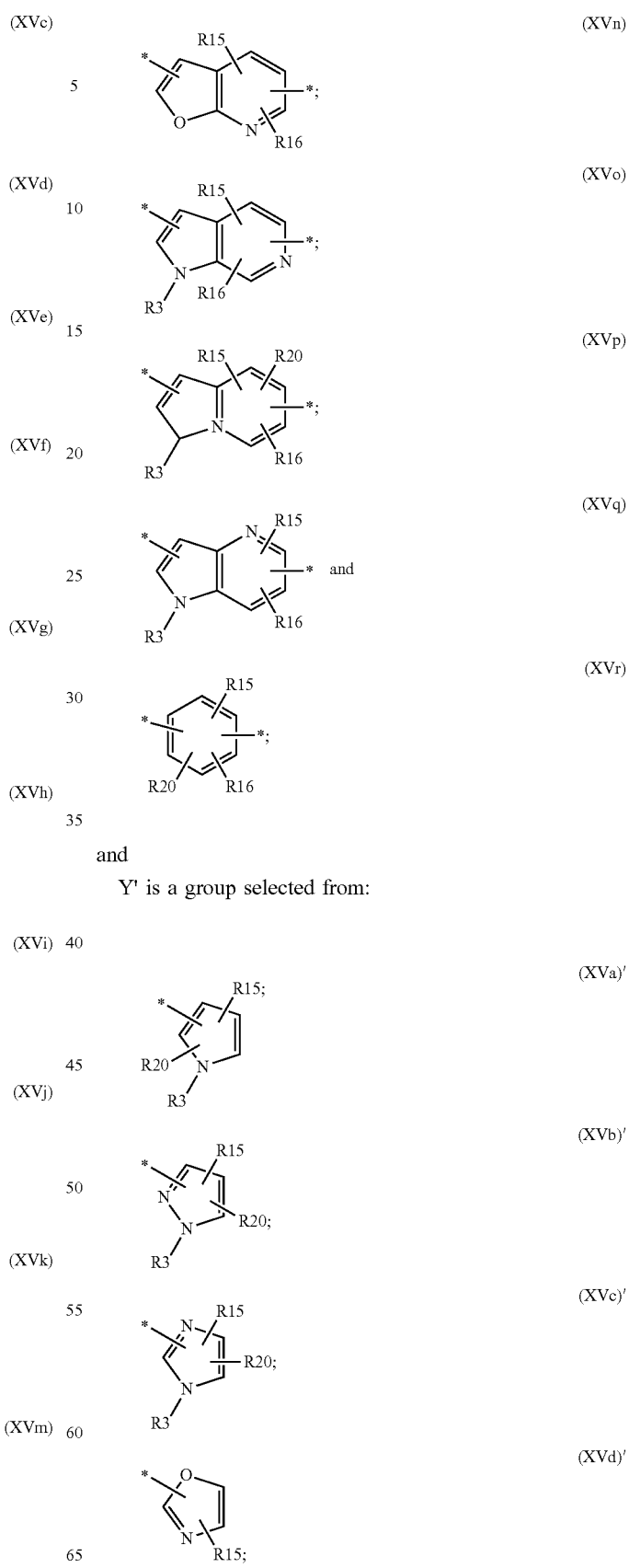
and
Y' is a group selected from:

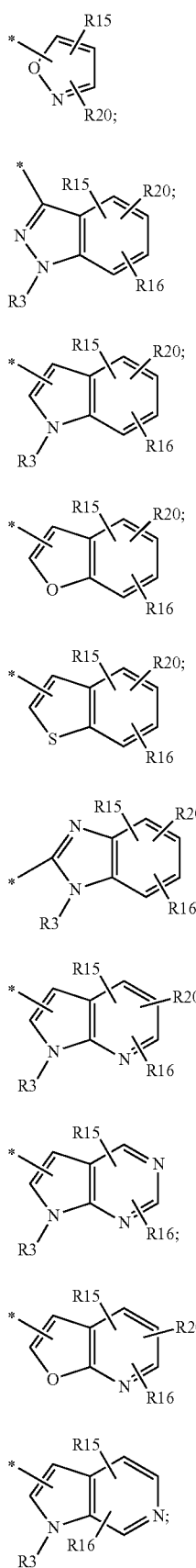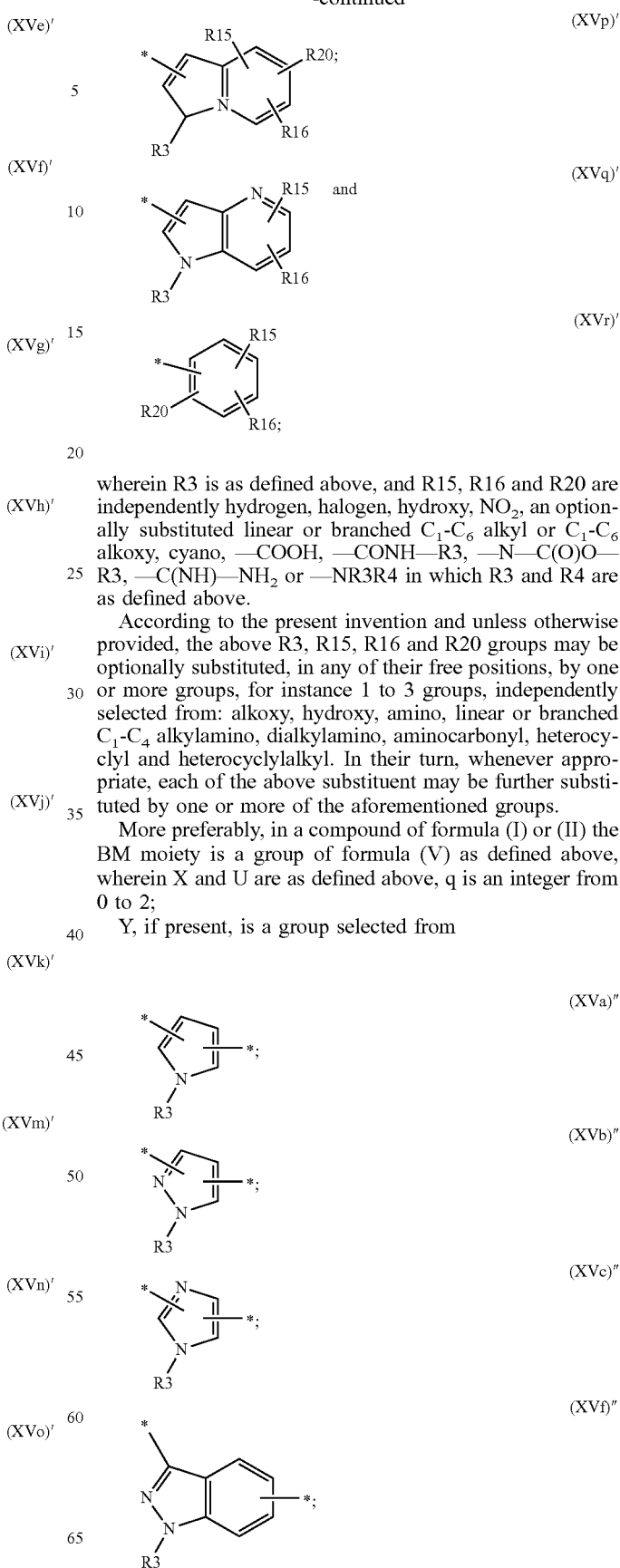

wherein R3 is as defined above, and R15, R16 and R20 are independently hydrogen, halogen, hydroxy, NO₂, an optionally substituted linear or branched $C_1$-$C_6$ alkyl or $C_1$-$C_6$ alkoxy, cyano, —COOH, —CONH—R3, —N—C(O)O—R3, —C(NH)—NH₂ or —NR3R4 in which R3 and R4 are as defined above.

According to the present invention and unless otherwise provided, the above R3, R15, R16 and R20 groups may be optionally substituted, in any of their free positions, by one or more groups, for instance 1 to 3 groups, independently selected from: alkoxy, hydroxy, amino, linear or branched $C_1$-$C_4$ alkylamino, dialkylamino, aminocarbonyl, heterocyclyl and heterocyclylalkyl. In their turn, whenever appropriate, each of the above substituent may be further substituted by one or more of the aforementioned groups.

More preferably, in a compound of formula (I) or (II) the BM moiety is a group of formula (V) as defined above, wherein X and U are as defined above, q is an integer from 0 to 2;

Y, if present, is a group selected from

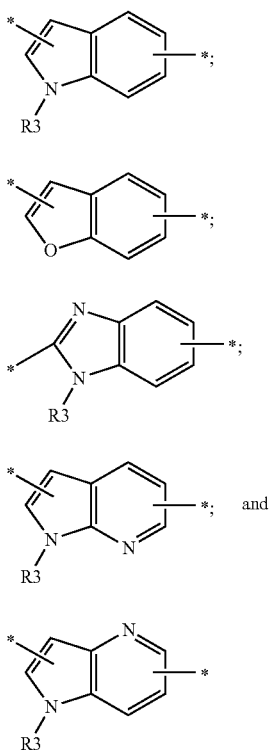

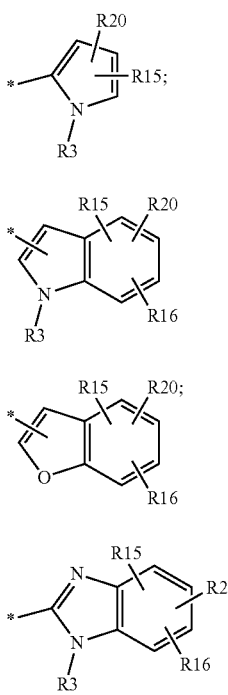

wherein R3 is as defined above; and

Y' is a group selected from:

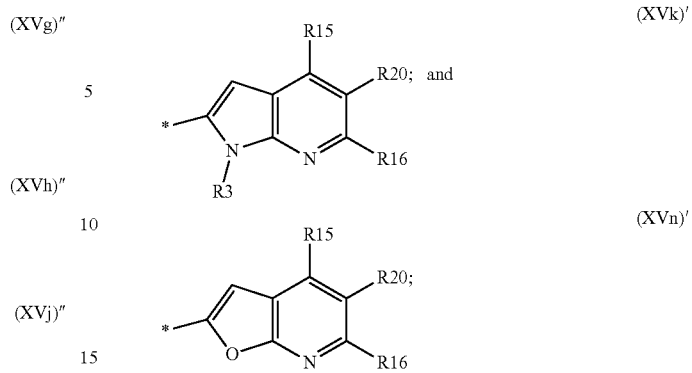

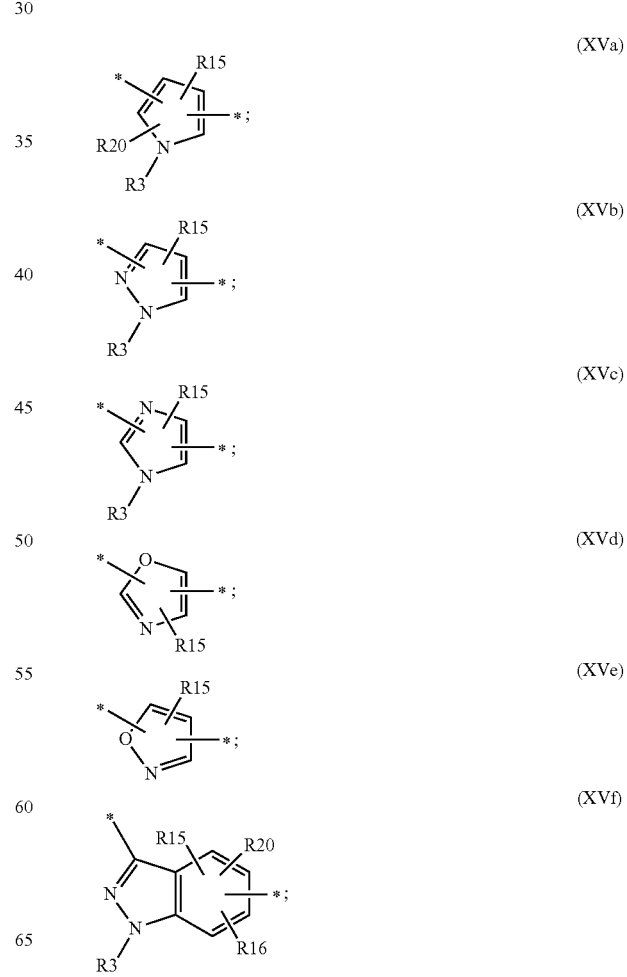

wherein R3 is as defined above, and R15, R16 and R20 are independently hydrogen or methoxy.

Preferably, in a compound of formula (III) or (IV), the BM moiety is a group of formula (V)' as defined above, wherein X is null or a $C_2$-$C_4$ alkenyl of formula (XIV) as defined above;

U and q are as defined above; and

Y, if present, and Y' are independently selected from:

-continued
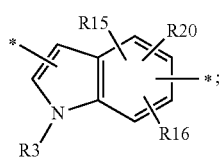 (XVg)
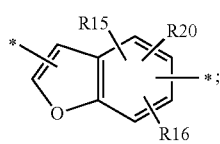 (XVh)
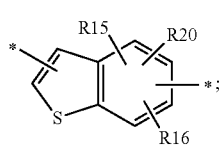 (XVi)
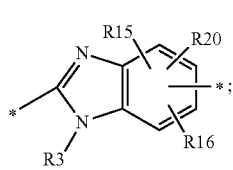 (XVj)
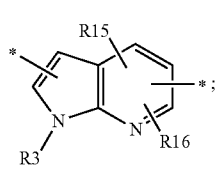 (XVk)
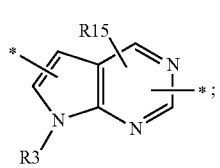 (XVm)
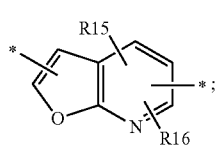 (XVn)
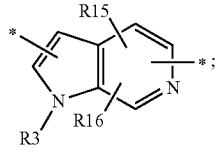 (XVo)
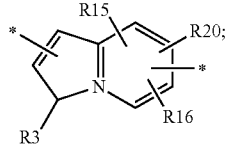 (XVp)
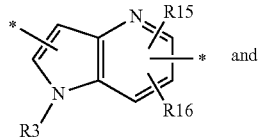 (XVq)
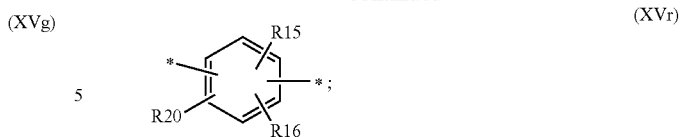 (XVr)
wherein R3, R15, R16 and R20 are as defined above.
More preferably, in a compound of formula (III) or (IV), the BM moiety is a group of formula (V)' as defined above, wherein X and U are as defined above, q is an integer from 0 to 2;
Y, if present, is selected from:
 (XVa)″
 (XVb)″
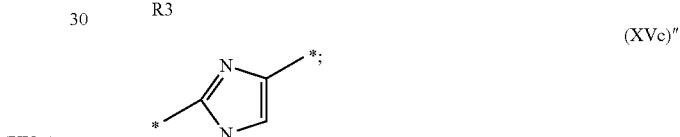 (XVc)″
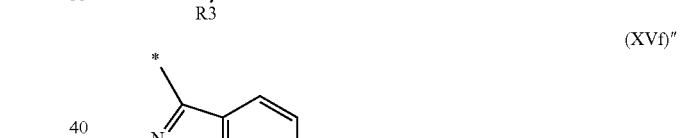 (XVf)″
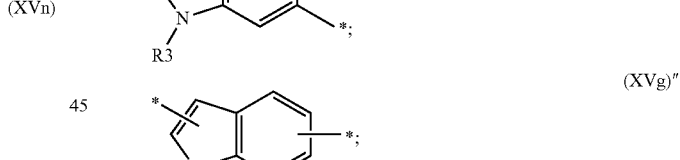 (XVg)″
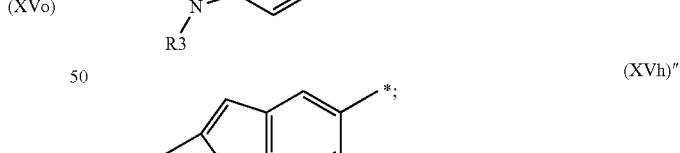 (XVh)″
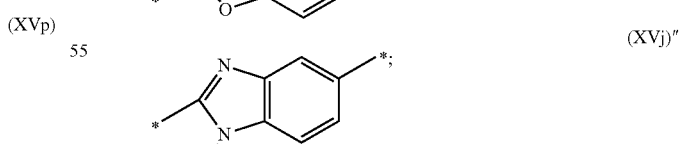 (XVj)″
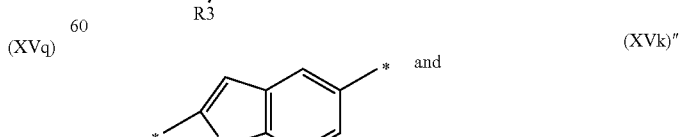 (XVk)″

-continued

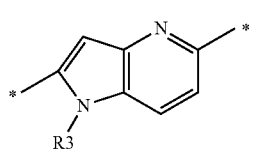
(XVq)″ wherein R3 is as defined above; and
Y' is a group selected from:

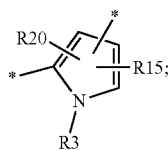
(XVa)

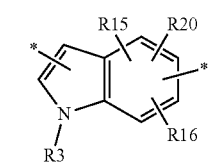
(XVg)

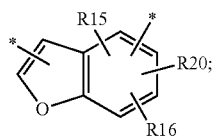
(XVh)

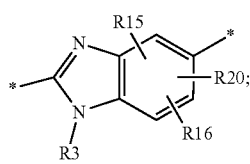
(XVj)

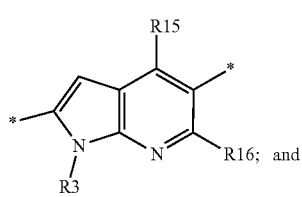
(XVk)

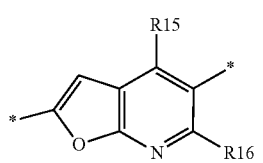
(XVn)

wherein R3 is as defined above and R15, R16 and R20 are independently hydrogen or methoxy.

The Conditionally-Cleavable Moiety L or L1

The L or L1 moiety, if present, is a conditionally-cleavable group that can be cleaved by a chemical, photochemical, physical biological or enzymatic process upon being brought in or under certain conditions. One of these condition may for example be bringing a compound of the invention in an aqueous environment, which leads to hydrolysis of L and/or L1, or bringing a compound of the invention in an environment that contains an enzyme that recognizes and cleaves L and/or L1, or bringing a compound of the invention under reducing conditions, which leads to reduction and/or removal of L and/or L1, or bringing a compound of the invention under oxidizing conditions, which leads to oxidation and removal of L and/or L1, or bringing a compound of the invention in contact with radiation, e.g., UV light, which leads to cleavage, or bringing a compound of the invention in contact with heat, which leads cleavage of L and/or L1. This condition may be met directly after administrating a compound of this invention to an animal, e.g., a mammal, for example a human, due to the presence of ubiquitous enzymes in the circulation. Alternatively, said condition may be met when the compound localizes to a specific organ, tissue, cell, subcellular target, or bacterial, viral, or microbial target, for example by the presence of internal factors (e.g., target-specific enzymes or hypoxia) or application of external factors (e.g., radiation, magnetic fields). Cleavage of L or L1 means that the bond between A and L in a compound of formula (III) or (IV), or between the oxygen and L1 in a compound of formula (II) or (IV) is broken:

$$\left. \begin{array}{c} \end{array} \right\} \left[ A \right] L - W - Z \right]_{RM} \text{ OR} \quad \text{(III) or (IV)}$$

$$\left. \begin{array}{c} \end{array} \right\} O \left] L - W - Z \right. \text{ OR} \quad \text{(II)}$$

$$\left. \begin{array}{c} \end{array} \right\} O \left[ \left[ L - W - Z1 \right]_{RM1} \right. \quad \text{(IV)}$$

It is noted that in a compound of formula (IV), two conditionally-cleavable groups can be present. In this case the two moieties may or may not be the same and may or may not require the same conditions for cleavage.

In one embodiment, L and/or L1 can be moieties that are cleaved by an enzyme or hydrolytic conditions present in the vicinity or inside the target cells as compared to other parts of the body, or by an enzyme or hydrolytic conditions, present only in the vicinity of or inside the target cells. It is important to recognize that if target site specificity is achieved solely based upon the selective transformation and/or cleavage of said L at the target site, the condition causing the cleavage should preferably, at least to a certain degree, be target site-specific. In one embodiment, cleavage of L occurs intracellularly.

In another embodiment, cleavage of L occurs extracellularly.

In another embodiment, cleavage of L and/or L1 can occur by a ubiquitous intracellular enzyme.

In one preferred embodiment L and/or L1 may be a moiety that can be cleaved by ubiquitous enzymes, e.g., esterases that are present in the circulation or intracellular enzymes, such as for example proteases and phosphatases, or by pH-controlled hydrolysis. L and/or L1 may therefore form, optionally together with the connecting atom(s) A or oxygen, a carbonate, carbamate, urea, ester, amide, imine, disulfide, ether, acetal, ketal or phosphate group that can be cleaved in vivo.

In a more preferred embodiment A is —O—, and L and L1 are independently null or a group selected from: —NHCO—R9 (Xa); —NHCONH—R9 (Xb); —NHCOO—R9 (Xc); —NH—R9 (Xd);

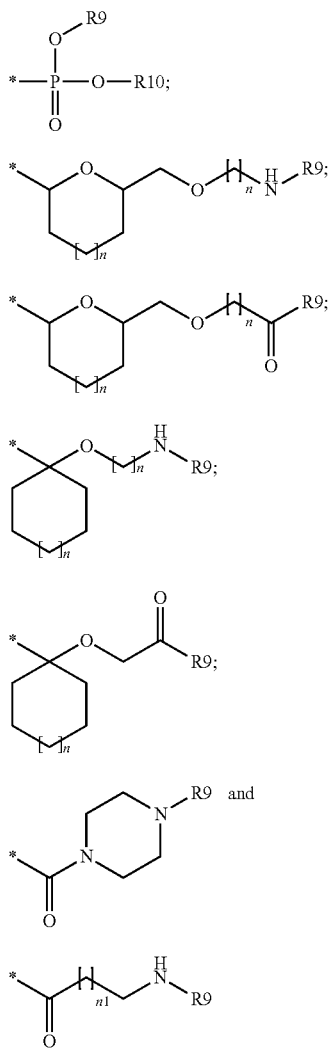

wherein:
R9 and R10 are, each independently, null, hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl;
n is an integer from 0 to 2 and
n1 is an integer from 0 to 4.

According to the present invention and unless otherwise provided, the above R9 and R10 groups may be optionally substituted, in any of their free positions, by one or more groups, for instance 1 to 3 groups, independently selected from: halogen, linear or branched $C_1$-$C_4$ alkyl, polyfluorinated alkyl, linear or branched $C_1$-$C_4$ alkoxy, polyfluorinated alkoxy, hydroxy, amino, linear or branched $C_1$-$C_4$ alkylamino, dialkylamino, $C_1$-$C_4$ alkylcarbonyl, $C_3$-$C_8$ cycloalkyl, cycloalkylalkyl, heterocyclyl, heterocyclylalkyl, aryl, arylalkyl, heteroaryl and heteroarylalkyl.

In another more preferred embodiment A is —N—, and L and L1 are independently null or a group selected from:

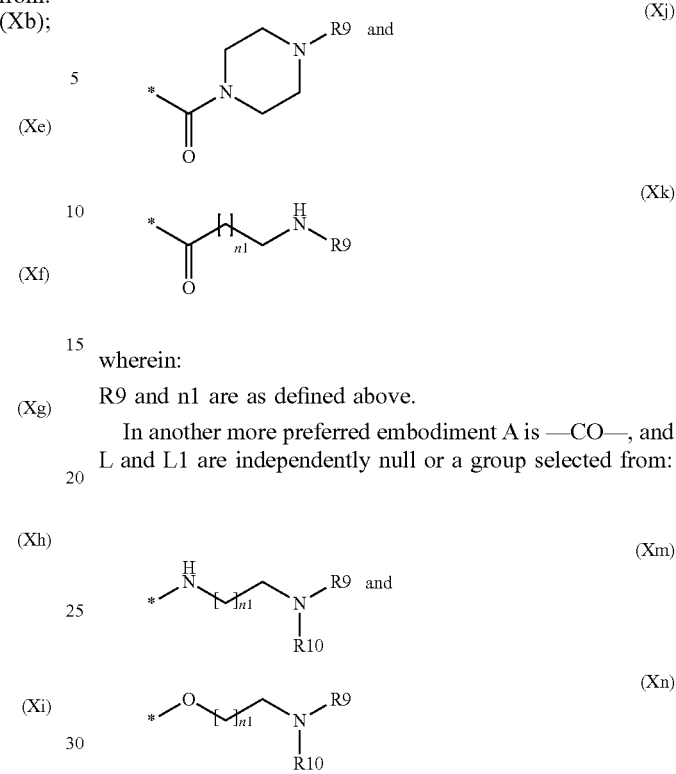

wherein:
R9 and n1 are as defined above.

In another more preferred embodiment A is —CO—, and L and L1 are independently null or a group selected from:

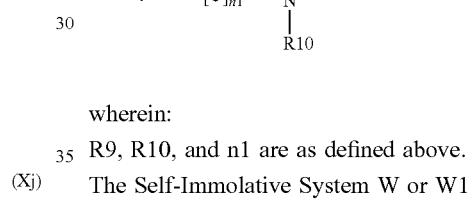

wherein:
R9, R10, and n1 are as defined above.

The Self-Immolative System W or W1

The W or W1 group, if present, is a self-immolative system that in a compound of formula (III) and (IV) tethers in a stable way from one side a moiety L or A (if L is null), to a moiety Z or RM (if Z is null); in a compound of formula (II) tethers in a stable way from one side a moiety L1 or oxygen (if L1 is null), to Z1 or additionally to RM1 (if Z1 is null) in compound of formula (IV). The L-W, A-W, L1-W1 or O—W1 bond can become labile upon activation by a chemical, photochemical, physical, biological or enzymatic process upon being brought in or under certain condition, as described above, leading optionally to the release of the corresponding moieties:

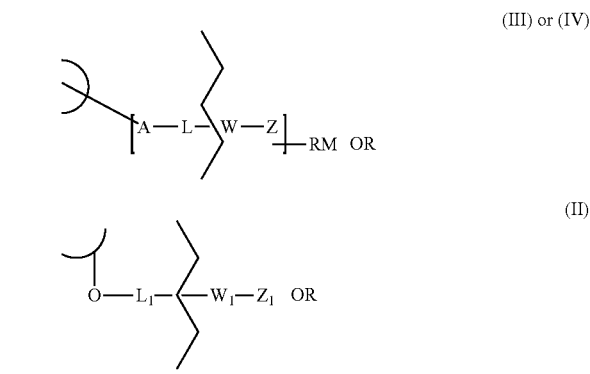

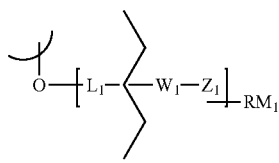

(IV)

It is noted that in compound of formula (IV), two self-immolative systems can be present. In this case the two systems may or may not be the same and may or may not require the same conditions for cleavage.

A self-immolative system may be incorporated in a compound of formula (II), (III) or (IV) for example to improve solubility or to improve space between the alkylating moiety and the reactive moiety; in addition said self-immolative system can modulate the reactivity of RM or RM1 versus nucleophfiles.

Self-immolative systems are known to the person skilled in the art see for example those described in WO2002/083180 and WO2004/043493; or those described in Tranoy-Opalinsi, A. et al, Anticancer Agents in Medicinal Chemistry, 2008, 8, 618-637. Other examples of self-immolative systems include, but are not limited to, optionally substituted 4-aminobutyric acid amides, appropriately substituted bicydo[2.2.1] and bicyclo[2.2.2] ring systems or 2-aminophenylpropionic acid amides [see WO 2005/079398, WO 2005/105154 and WO 2006/012527; Greenwald, R. B., et al, Adv. Drug Delivery Rev. 2003, 55, 217-250; Kingsbury, W. D.; et al, J. Med. Chem. 1984, 27, 1447-1451].

In one preferred embodiment W or W1 may form together with the connecting atom(s) L, L1, A, Z, Z1, RM, RM1 or oxygen, a carbonate, carbamate, urea, ester, amide, ether or thioamide linkage group that can be optionally cleaved upon activation.

In preferred embodiment, W and W1 are independently null or a self-immolative system, comprising one or more self-immolative groups independently selected from:

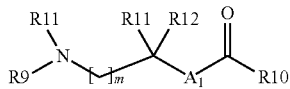

(XIa)

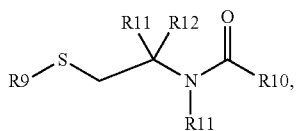

(XIb)

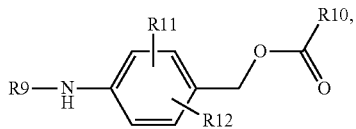

(XIc)

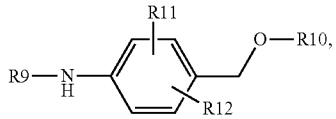

(XId)

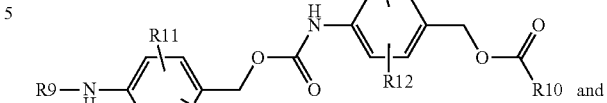

(XIe)

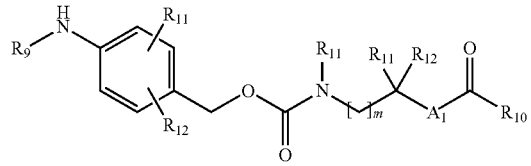

(XIj)

wherein
one of R9 and R10 is null and the other is as defined above;
R11 and R12 are, each independently, hydrogen, halogen, methyl, ethyl or linear or branched $C_1$-$C_4$ hydroxymethyl;
m is an integer from 0 to 3; and
$A_1$ is $CH_2$, $CH_2N$—R12 or N—R12, wherein R12 is as defined above.

In another more preferred embodiment, W and W1 are independently null or a group selected from:

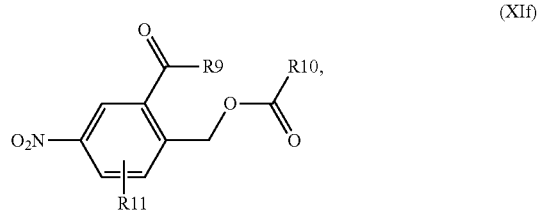

(XIf)

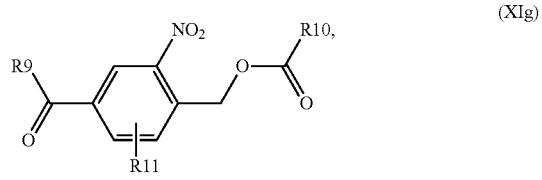

(XIg)

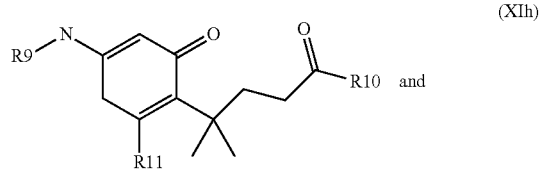

(XIh)

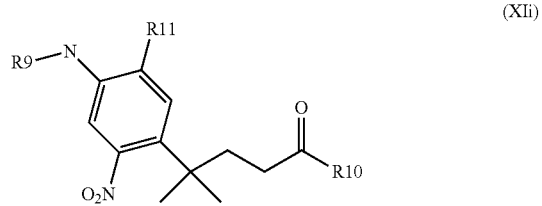

(XIi)

wherein one of R9 and R10 is null and the other is as defined above; and
R11 is as defined above.

The Z or Z1 Linker

The Z or Z1 linker, if present, can be peptidic ($Z_a$), non-peptidic ($Z_b$) or hybrid, wherein said hybrid linker is peptidic and non-peptidic ($Z_c$); in a compound of formula (II), (III) or (IV) said Z or Z1 linker can be cleaved from W or W1, respectively, by a chemical, photochemical, physical biological or enzymatic process upon being brought in or under certain conditions, as described above:

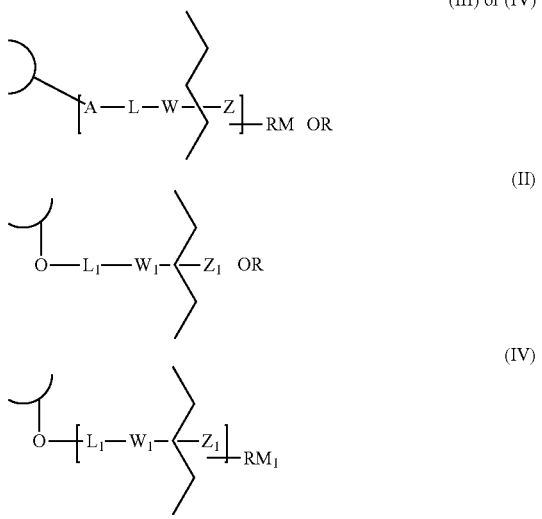

The Z or Z1 linker may be linear or branched.

The linkage between Z or Z1 and its left hand side moiety or between Z or Z1 and, optionally, RM or RM1, may be an amide, a carbonate, a disulfide or a carbamate linkage.

In one embodiment both of Z and Z1 are null; in another embodiment one of Z or Z1 is null.

In another embodiment Z, Z1 is a peptidic linker $Z_a$ that can be cleaved by a proteolytic enzyme, plasmin, a cathepsin, β-glucuronidase, a galactosidase, prostate-specific antigen (PSA), urokinase-type plasminogen activator (u-PA) or a member of the family of matrix metalloproteinases.

In another embodiment Z, Z1 is a non-peptidic linker $Z_b$ that may contain one or more non-peptidic water-soluble moieties. In this case the linker contributes to the water solubility of a compound of formula (II), (III) or (IV).

In another embodiment $Z_b$ is a non-peptidic linker that may contain one or more non-peptidic moieties that reduce(s) aggregation of a compound of formula (II), (III) or (IV), which may or may not be a moiety/moieties that also increase(s) the water solubility of a compound of formula (II), (III) or (IV).

For example, non-peptidic water-soluble $Z_b$ linkers may contain an oligoethylene glycol or polyethylene glycol moiety or a derivative thereof.

In another embodiment Z, Z1 is a hybrid linker $Z_c$ that can contains both, peptidic and non peptidic residues of general formula $Z_a$—$Z_b$ wherein $Z_a$ and $Z_b$ are independently a peptidic linker or a non-peptidic linker. Hybrid linkers may contribute to solubility of compound of formula (II), (III) or (IV) and/or be a substrate that can be cleaved by proteolytic enzyme, for example by a member of the family of matrix metalloproteinases.

In a preferred embodiment, $Z_a$ is a single amino acid, a dipeptide, a tripeptide, a tetrapeptide, or an oligopeptide moiety comprising natural L-amino acids, unnatural D-amino acids, synthetic amino acids, or any combination thereof, wherein one of the C-terminal or the N-terminal amino acid residue is linked to W, L or A or to W1, L1, or oxygen and, the other terminal amino acid ends with a COOH or NH2 group or is optionally linked to RM or RM1.

In a more preferred embodiment $Z_a$ is a dipeptide or a tripeptide, linked via its C-terminus to W or W1, or to L when W is null, or to L1 when W1 is null, or to A when W and L are both null, or to 0 when W1 and L1 are both null.

In another more preferred embodiment, the C-terminal amino acid residue of the dipeptide or of the tripeptide is selected from glycine, alanine, arginine and citrulline; and the N-terminal amino acid residue is selected from any natural or unnatural amino acid; preferably, in case of the tripeptide, the middle amino acid residue is selected from alanine, valine, leucine, isoleucine, methionine, phenylalanine and proline.

In another more preferred embodiment $Z_a$ comprises a pentapeptide, wherein the C-terminal amino acid is selected from any natural or unnatural amino acid and the N-terminal amino acid residue is 6-aminohexanoic acid.

In a preferred embodiment $Z_b$ may contain an oligoethylene glycol or polyethylene glycol moiety or a derivative thereof.

In a more preferred embodiment $Z_b$ is a group selected from:

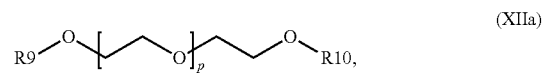 (XIIa)

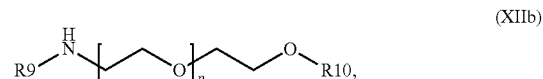 (XIIb)

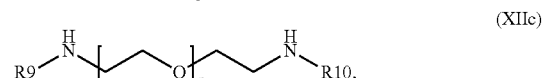 (XIIc)

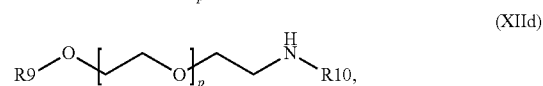 (XIId)

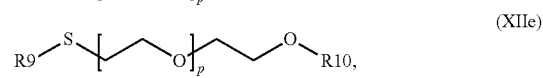 (XIIe)

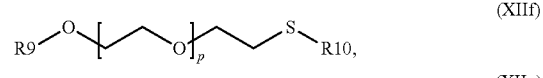 (XIIf)

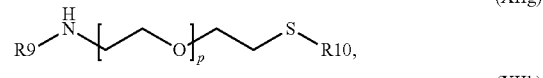 (XIIg)

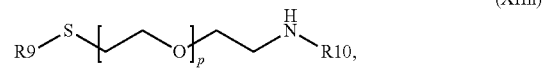 (XIIh)

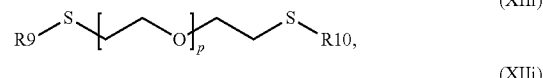 (XIIi)

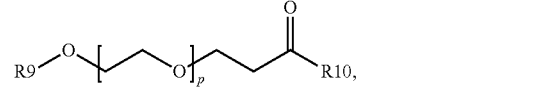 (XIIj)

 (XIIk)

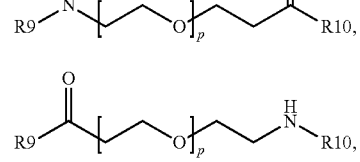 (XIIm)

-continued

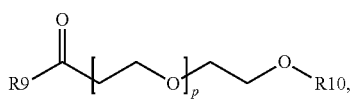
(XIIn)

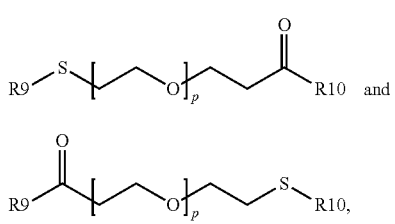
(XIIo)

and (XIIp)

wherein
one of R9 and R10 is null and the other is are as defined above; and
p is an integer from 1 to 20;

In a preferred embodiment $Z_c$ is a hybrid moiety comprising
a peptidic moiety $Z_a$, wherein $Z_a$ is a single amino acid, a tripeptide or a tetrapeptide, comprising natural L amino acids and unnatural D amino acids; and
a non-peptidic moiety $Z_b$ comprising an oligoethylene glycol or polyethylene glycol moiety or a derivative thereof.

The Reactive Moiety RM or RM1

The RM or RM1 moiety, if present, is an electrophilic group that can react with nucleophiles, i.e. molecules that bear a nucleophilic group, under relatively mild conditions and without the need of prior functionalization of the reactive moiety, said reaction between the reactive moiety and said nucleophile will only require the application of some heat, pressure, a catalyst, acid, and/or base.

Therefore, when one of RM or RM1 moiety is present, a compound of formula (III) o (IV) conjugates with different types of nucleophiles.

When both RM and RM1 moiety are null, a compound of formula (III) or (IV) conjugates with different types of electrophiles, i.e. molecules that bear an electrophilic group, through one or more of the nucleophilic groups that are present on the A, L, L1, W, W1, Z and Z1 moiety(ies).

In a compound of formula (III) the RM moiety can be connected to one or more of the A, L, W or Z groups; in a compound of formula (IV), RM can be connected either to one or more of the A, L, W or Z groups and/or to one ore more of the L1, W1, Z1 groups or to the oxygen atom:

(III) or (IV)

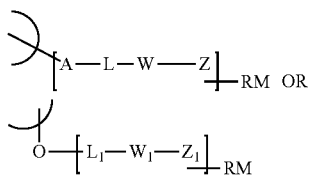

Examples of reactive moieties include, but are not limited to, carbamoyl halide, acyl halide, active ester, anhydride, α-haloacetyl, α-haloacetamide, maleimide, isocyanate, isothiocyanate, disulfide, thiol, hydrazine, hydrazide, sulfonyl chloride, aldehyde, methyl ketone, vinyl sulfone, halomethyl, and methyl sulfonate.

In one preferred embodiment of the invention, when the nucleophilic group of the nucleophile is NH, $NH_2$ or OH, RM and RM1 are independently null or a group selected from

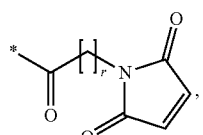
(XIIIa)

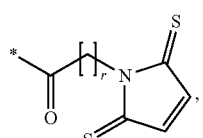
(XIIIb)

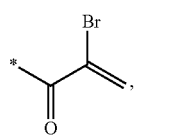
(XIIIc)

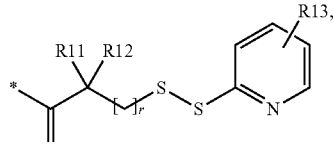
(XIIId)

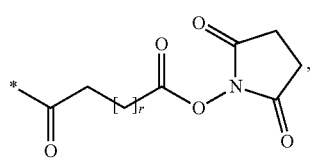
(XIIIe)

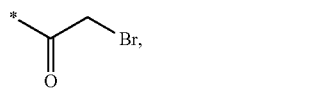
(XIIIf)

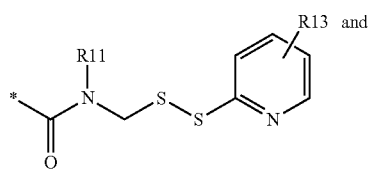
(XIIIg)

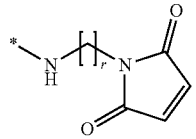
(XIIIm)

wherein R13 is $C_1$-$C_3$ alkyl or an electron-withdrawing group comprising $NO_2$ and CN group;
r is an integer from 0 to 7; and
R11 and R12 are as defined above.

In another preferred embodiment of the invention, when the nucleophilic group of the nucleophile is COOH, RM and RM1 are independently null or a group selected from

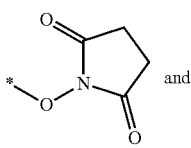
(XIIIh) and

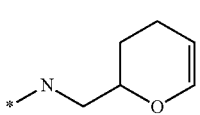
(XIIIi)

In another preferred embodiment of the invention, when the nucleophilic group of the nucleophile is SH, RM and RM1 are independently null or a group selected from

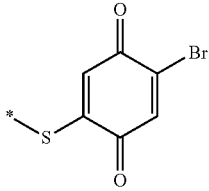
(XIIIj) and

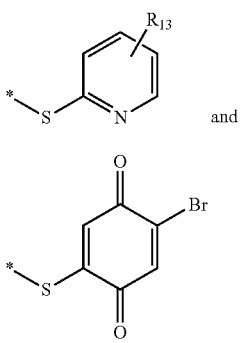
(XIIIk)

wherein R13 is as defined above.

In a most preferred embodiment at least one of RM and RM1 is not null.

Preferably, the present invention provides compounds of formula (I) or (II) as defined above, characterized in that R1 and R2 taken together form a group (D), wherein R5 is linear or branched $C_1$-$C_4$ alkyl.

More preferably, the present invention provides compounds of formula (II) as defined above, characterized in that R6 is halide and L1 is hydrogen or a conditionally-cleavable moiety of formula (Xj)

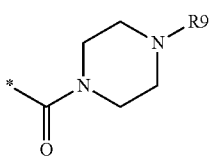
(Xj)

wherein R9 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl.

Preferably, the present invention provides compounds of formula (III) or (IV) as defined above, characterized in that R1 and R2 taken together form a group (D), wherein R5 is linear or branched $C_1$-$C_4$ alky.

More preferably, the present invention provides compounds of formula (IV) as defined above, characterized in that R6 is halide; and A' is null and L1 is L, wherein L is as defined above.

More preferably, the present invention provides compounds of formula (III) or (IV) as defined above, characterized in that L and L1 are independently null or a conditionally-cleavable moiety selected from NHCO—R9 (Xa); —NHCONH—R9 (Xb); —NHCOO—R9 (Xc); —NH—R9 (Xd);

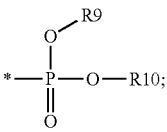
(Xe)

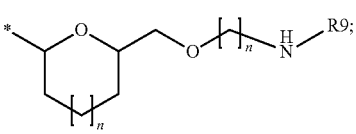
(Xf)

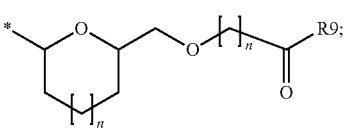
(Xg)

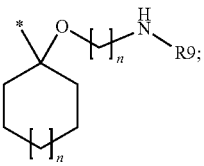
(Xh)

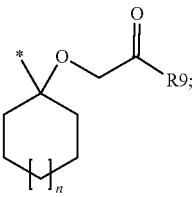
(Xi)

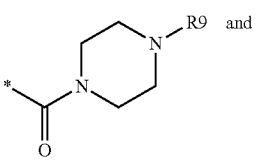
(Xj) and

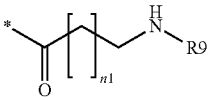
(Xk)

wherein:

R9 and R10 are, each independently, null, hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl;

n is an integer from 0 to 2 and n1 is an integer from 0 to 4.

More preferably, the present invention provides compounds of formula (III) or (IV) as defined above, characterized in that W and W1 are independently a self-immolative system comprising one or more self-immolative groups independently selected from:

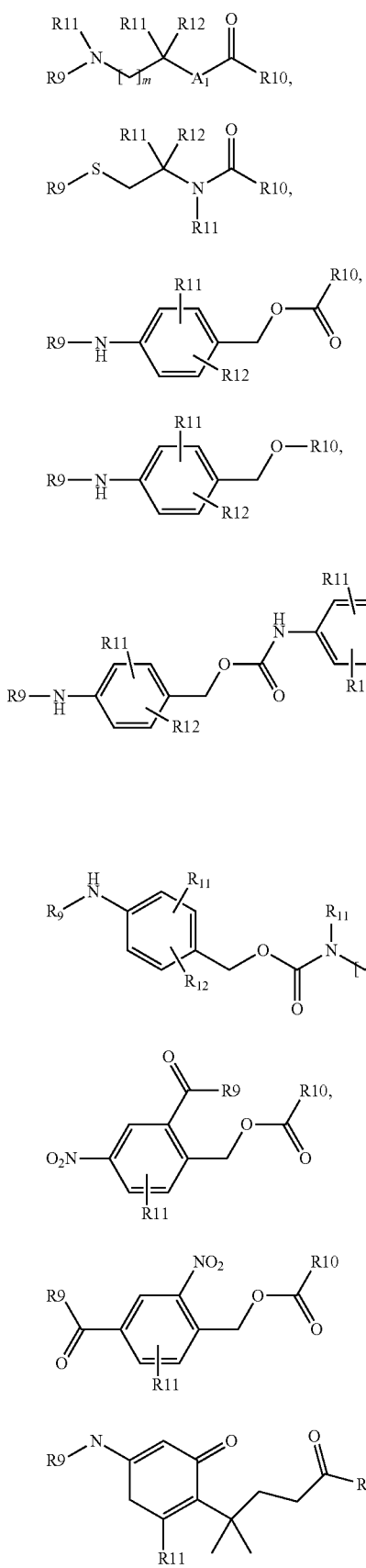

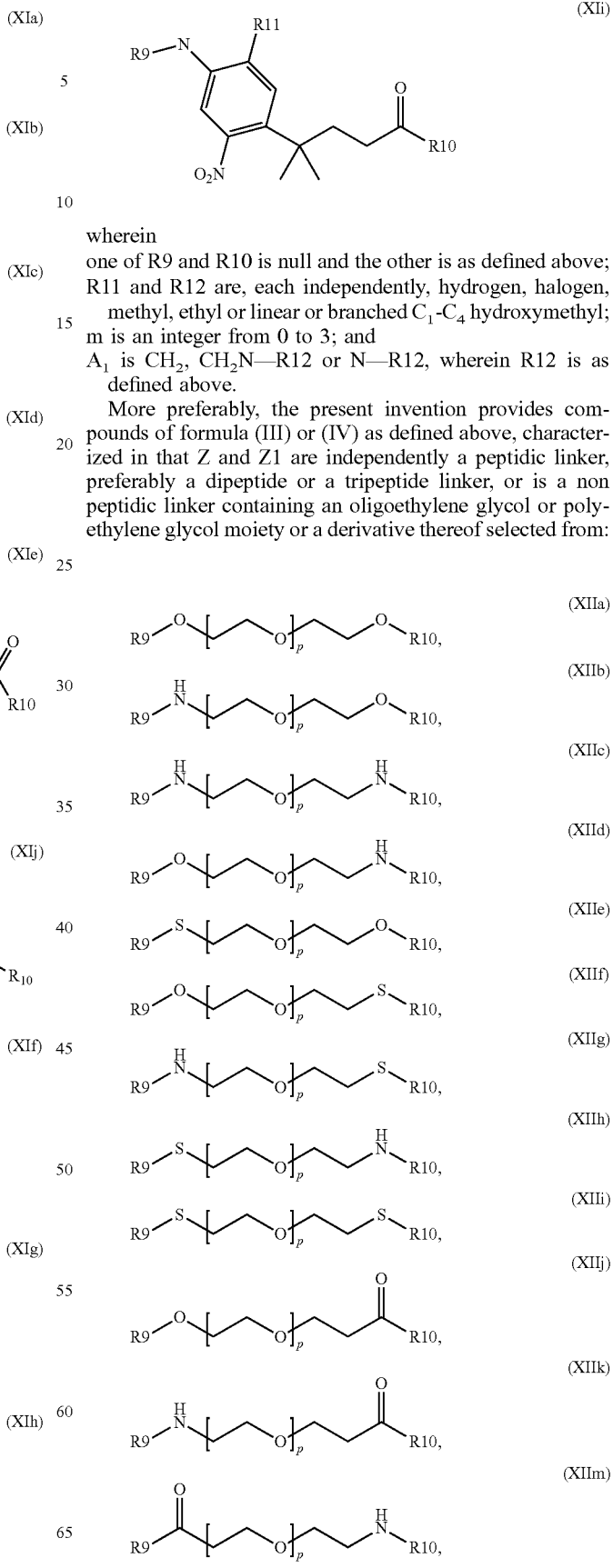

wherein
one of R9 and R10 is null and the other is as defined above;
R11 and R12 are, each independently, hydrogen, halogen, methyl, ethyl or linear or branched $C_1$-$C_4$ hydroxymethyl;
m is an integer from 0 to 3; and
$A_1$ is $CH_2$, $CH_2N$—R12 or N—R12, wherein R12 is as defined above.

More preferably, the present invention provides compounds of formula (III) or (IV) as defined above, characterized in that Z and Z1 are independently a peptidic linker, preferably a dipeptide or a tripeptide linker, or is a non peptidic linker containing an oligoethylene glycol or polyethylene glycol moiety or a derivative thereof selected from:

-continued

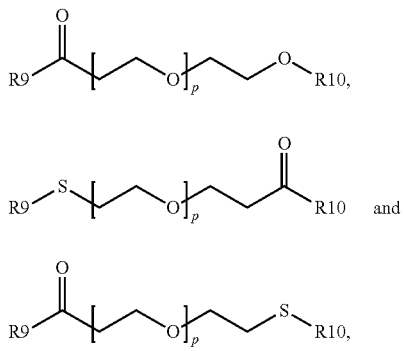

(XIIn)

(XIIo)

(XIIp)

wherein
one of R9 and R10 is null and the other is are as defined above; and
p is an integer from 1 to 20.

More preferably, the present invention provides compounds of formula (III) or (IV) as defined above, characterized in that RM and RM1 are independently a reactive moiety selected from

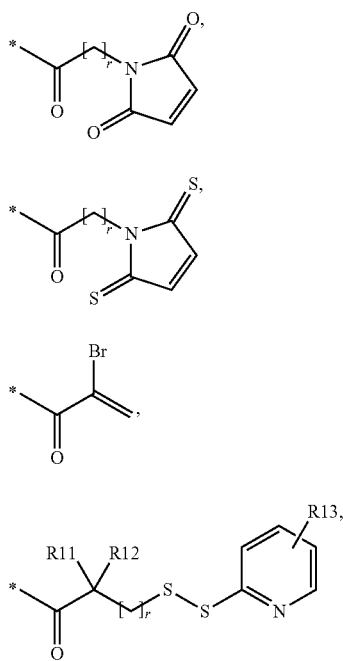

(XIIIa)

(XIIIb)

(XIIIc)

(XIIId)

(XIIIe)

(XIIIf)

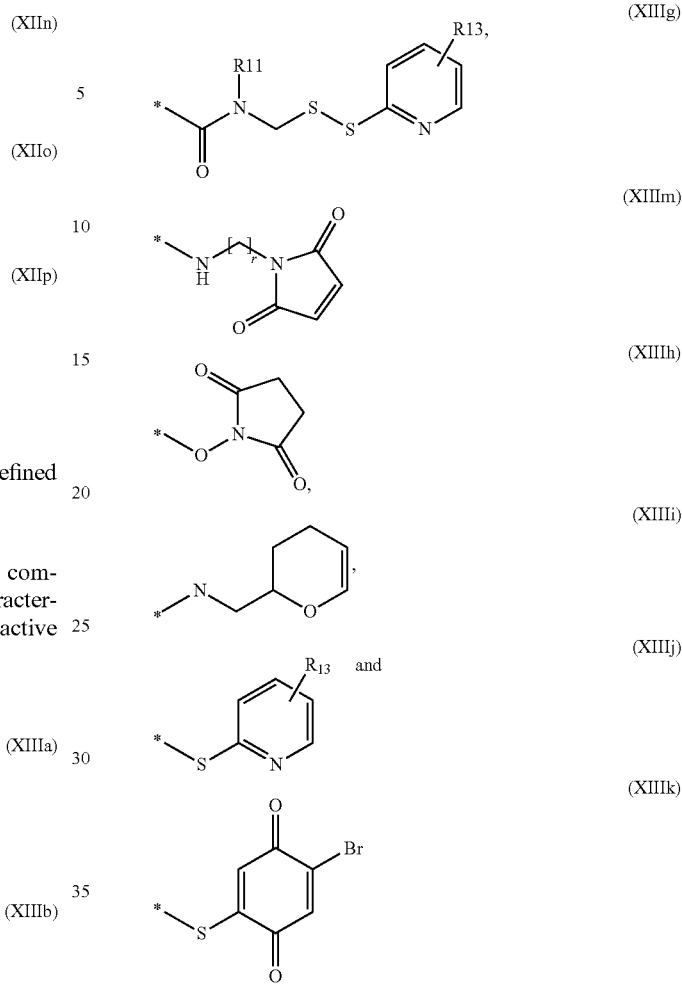

(XIIIg)

(XIIIm)

(XIIIh)

(XIIIi)

(XIIIj)

(XIIIk)

wherein R13 is $C_1$-$C_3$ alkyl or an electron-withdrawing group comprising $NO_2$ and CN group;
r is an integer from 0 to 7; and
R11 and R12 are as defined above.

Specific, not limiting, preferred compounds (compd.) of the present invention, optionally in the form of a pharmaceutically acceptable salt, are the following:

1) N-(6-{[(8S)-8-(chloromethyl)-4-hydroxy-1-methyl-7,8-dihydro-6H-thieno[3,2-e]indol-6-yl]carbony}-1H-indol-3-yl)-1H-indole-6-carboxamide, 2) N-{[(8R)-8-(chloromethyl)-4-hydroxy-1-methyl-7,8-dihydro-6H-thieno[3,2e]indol-6-yl]carbonyl}-1-methyl-1H-pyrrol-3-yl)-1-methyl-4-{[(1-methyl-4-nitro-1H-pyrrol-2-yl)carbonyl]amino}1H-pyrrole-2-carboxamide, 3) (2E)-1-[(8R)-8-(chloromethyl)-4-hydroxy-1-methy-7,8-dihydro-6H-thieno[3,2-e]indol-6-yl]-3-(1H-pyrrolo[2,3-b]pyridin-3-yl)prop-2-en-1-one, 4) (2E)-1-[(8S)-8-(chloromethyl)-4-hydroxy-1-methyl-7,8 dihydro-6H-thieno[3,2-e]indol-6-yl]3-1H-pyrrolo[2,3-b]pyridin-3-yl)prop-2-en-1-one, 5) N-(6-{[(3bR,4aS)-3-methyl-oxo-4a,5-dihydro-4H-cyclopropa[c]thieno[3,2-e]indol-6(8H)-yl]carbonyl}-1H-indol-3-yl)-1H-indole-6-carboxamide, 6) 1-methyl-N-(1-methyl-5-{[(3bS,4aR)-3-methy-oxo-4a,5-dihydro-4H-cyclopropa[c]thieno[3,2-e]indol-6(8H)-yl]carbonyl}-1H-pyrrol-yl)-4-{[(1-methyl-4-nitro-1H-pyrrol-2-yl)carbonyl]amino}-1H-pyrrole-2-carboxamide, 7) (3bS,4aR)-3-methyl-6-[(2E)-3-(1H-pyrrolo[2,3b]prop-2-enoyl]-4,4a,5,6-tetrahydro-8H-cyclopropa[c]thieno[3,2-e]indol-8-one,
8) (3bR,4aS)-3-methyl-6-[(2E)-3-(1H-pyrrolo[2,3-b]pyridin-3-yl)prop-2-enoyl]-4,4a,5,6-tetrahydro-8H-cyclopropa[c]thieno[3,2-e]indol-8-one,
9) (3bS,4aR)—N-(5-{[5-({5-[(3-amino-3-oxopropyl)carbamoyl]-1-methyl-1H-pyrrol-3-yl}carbamoyl)-1-methyl-1 H-pyrrol-3-yl]carbamoyl}-1-methyl-1H-pyrrol-3-yl)-3-methyl-8-oxo-4a,5-dihydro-4H-cyclopropa[c]thieno[3,2-e]indole-6(8H)-carboxamide,
10) (8R)—N-(5-{[5-({5-[(3-amino-3-oxopropyl)carbamoyl]-1-methyl-1H-pyrrol-3-yl)carbamoyl}-1-methyl-1H-pyrrol-3-yl]carbamoyl}-1-methyl-1H-pyrrol-3-yl)-8-(chloromethyl)-4-hydroxy-1-methyl-7,8-dihydro-6H-thieno[3,2-e]indole-6-carboxamide,
11) (8S)—N-(5-{[5-({5-[(3-amino-3-oxopropyl)carbamoyl]-1-methyl-1H-pyrrol-3-yl)carbamoyl}-1-methyl-1H-pyrrol-3-yl]carbamoyl}-1-methyl-1H-pyrrol-3-yl)-8-(chloromethyl)-4-hydroxy-1-methyl-7,8-dihydro-6H-thieno[3,2-e]indole-6 carboxamide,
12) (3bR,4aS)—N-(5-{[5-({5-[(3-amino-3-oxopropyl)carbamoyl]-1-methyl-1H-pyrrol-3-yl}carbamoyl)-1-methyl-1 H-pyrrol-3-yl]carbamoyl}1-methyl-1H-pyrrol-3-yl)-3-methyl-8-oxo-4a,5-dihydro-4H-cyclopropa[c]thieno[3,2-e]indole-6(8H)-carboxamide,
13) N-(3-{(1E)-3-[(8S)-8-(chloromethyl)-4-hydroxy-1-methyl-7,8-dihydro-6H-thieno[3,2-e]indol-6-yl]-3-oxoprop-1-en-1-yl}-1H-pyrrolo[2,3-b]pyridin-5-yl)-1H-indole-2-carboxamide,
14) N-(3-{(1E)-3-[(8R)-8-(chloromethyl)-4-hydroxy-1 methyl-7,8-hydro-6H-thieno[3,2-e]indol-6-yl]-3-oxoprop-1-en-1-yl}-1H-pyrrolo[2,3-b]pyridin-5-yl)-1H-indole-2-carboxamide,
15) N-(3-{(1E)-3-[(3bR,4aS)-3-methyl-8-oxo-4a,5-dihydro-4H-cyclopropa[c]thieno[3,2-e]indol-6(8H)-yl]3-oxoprop-1-en-1-yl}-1H-pyrrolo[2,3-b]pyridin-5-yl)-1H-indole-2-carboxamide,
16) N-(3-{(1E)-3-[(3bR,4aS)-3-methyl-oxo-4a,5-dihydro-4H-cyclopropa[c]thieno[3,2-e]idol-6(8H)-yl]-3-oxoprop-1-en-1-yl}-1H-pyrrolo[2,3-b]pyridin-5-yl)-1H-indole-2-carboxamide,
17) N-(2-{[(8S)-8-(chloromethyl)-4-hydroxy-1-methyl-7,8-dihydro-6H-thieno[3,2-e]indol-6-yl]carbonyl}-1H-indol-5-yl)-5-[2-(pyrrolidin-1-yl)ethoxy]-1H-indole-2-carboxamide,
18) tert-buty {2-[(2-{[(8S)-8-chloromethyl)-4-hydroxy-1-methyl-7,8-dihydro-6H-thieno[3,2-e]indol-6-yl]carbonyl}-1H-indol-5-yl)carbamoyl]-1H-indol-5-yl}carbamate,
19) 5-amino-N-(2-{[8S)-8-(chloromethyl)-4-hydroxy-1-methyl-5a,7,8,8a-tetrahydro-6H-thieno[3,2-e]indol-6-yl]carbonyl}-1H-indol-5-yl)-1H-indole-2-carboxamide,
20) tert-butyl {2-[(2-{[(3bR,4aS)-3-methyl-8-oxo-4a,5-dihydro-4H-cyclopropa[c]thieno[3,2-e]indol-6(8H)-yl]carbonyl}-1H-indol-5-yl)carbamoyl]-1H-indo-5-yl}carbamate,
21) 5-amino-N-(2-{[(3bR,4aS)-3-methyl-8-oxo-4a,5-dihydro-4H-cyclopropa[c]thieno[3,2-e]indol-6(8H)-yl]carbonyl}-1H-indol-5-yl)-1H-indole-2-carboxamide,
22) (8S)-6-({5-[({5-[(tert-butoxycarbonyl)amino]-1H-indol-2-yl}carbonyl)amino]-1H-indol-2-yl}carbonyl)-8-(chloromethyl)-1-methyl-7,8-dihydro-6H-thieno[3,2-e]indol-4-yl 4-methylpiperazine-1-carboxylate,
23) (8S)-6-[(5-{[(5-amino-1H-indol-2-yl)carbonyl]amino}-1H-indol-2-yl)carbonyl]-8-(chloromethyl)-1-methyl-7,8-dihydro-6H-thieno[3,2-e]indol-4-yl 4-methylpiperazine-1-carboxylate hydrochloride,
24) (8S)-8-chloromethyl)-6-({5-[(1H-indol-2-yl}carbonyl)amino]-1H-indol-2-yl)carbonyl)-1-methyl-7,8-dihydro-6H-thieno[3,2-e]indol-4-yl piperazine-1-carboxylate,
25) tert-butyl {2-[(2-{[(3bS,4aR)-3-methyl-8-oxo-4a,5-dihydro-4H-cyclopropa[c]thieno[3,2-e]indo-6(8H)-yl]carbonyl}1H-indol-5-yl)carbamoyl]-1H-indol-5-yl}carbamate,
26) 5-amino-N-2-{[(3bS,4aR)-3-methyl-8-oxo-4a,5-dihydro-4H-cyclopropa[c]thieno[3,2-e]indol-6(8H)-yl]carbonyl}-1H-indol-5-yl)-1H-indole-2-carboxamide,
27) (8R)-6-({5-[({5-[(tert-butoxycarbonyl)amino]-1H-indol-2-yl}carbonyl)amino]-1H-indol-2-yl}carbonyl)-8-(chloromethyl)-1-methyl-7,8-dihydro-6H-thieno[3,2-e]indol-4-yl 4-methylpiperazine-1-carboxylate,
28) (8R)-6-(5-{[(5-amino-1H-indol-2-yl)carbonyl]amino}-1H-indol-2-yl)carbonyl]-8-(chloromethyl)-1-methyl-7,8-dihydro-6H-thieno[3,2-e]indol-4-yl 4-methylpiperazine-1-carboxylate hydrochloride,
29) N-(2-{[(3bR,4aS)-3-methyl-8-oxo-4a,5-dihydro-4H-cyclopropa[c]thieno[3,2-e]indol-6(8H)-yl]carbonyl}-1 H-indol-5-yl)-5-nitro-1H-indole-2-carboxamide,
30) N-(2-{[(3bS,4aR)-3-methyl-8-oxo-4a,5-dihydro-4H-cyclopropa[c]thieno[3,2-e]indol-6(8H)-yl]carbonyl}1H-indol-5-yl)-5-nitro-1H-indole-2-carboxamide,
31) (8S)-8-(chloromethyl)-1-methyl-6-[(5-{[(5-nitro-1H-indol-2-yl)carbonyl]amino}-1H-indol-2-yl)carbonyl]-7,8-dihydro-6H-thieno[3,2-e]indol-4-yl 4-methylpiperazine-1-carboxylate,
32 (8R)-8-(chloromethyl)-1-methyl-6-[(5-{[(5-nitro-1H-indol-2-yl)carbonyl]amino}-1H-indol-2-yl)carbonyl]-7,8-dihydro-6H-thieno[3,2-e]indol-4y 4-methylpiperazine-1-carboxylate,
33) (8S)-8-chloromethyl)-6-[(5-{[(5-hydroxy-1H-indol-2-yl)carbonyl]amino}-1H-indol-2-yl)carbonyl]-1-methyl-7,8-dihydro 6H-thieno[3,2-e]indol-4-yl 4-methylpiperazine-1-carboxylate,
34) (8R)-8-(chloromethyl)-6-[(5-{[(5-hydroxy-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate,
35) N-[6-(2,5-dioxo-2,5-dihydro-1H-pyrrol-1-yl)hexanoyl]-L-valyl-N~5~-carbamoyl-N-[4-({[{3-[({[(8S)-8-(chloromethyl)-1-methy-6-({5-[({5-[2-{pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide,
36) N-[6-(2,5-dioxo-2,5-dihydro-1H-pyrrol-1-yl)hexanoyl]-L-valyl-N~5~-carbamoyl-N-[4-({[{3-[({[(8R)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide,
37) [(8S)-8-(chloromethyl)-4-hydroxy-1-methyl-7,8-dihydro-6H-thieno[3,2-e]indol-6-yl]{5-[2-(pyrrolidin-1-yl)ethoxyl]-1H-indol-2-yl}methanone,
38) [(8R)-8-(chloromethyl)-4-hydroxy-1-methyl-7,8-dihydro-6H-thieno[3,2-e]indol-6-yl]{5-[2-(pyrrolidin-1-yl)ethoxy]-1H-indol-2-yl}methanone,
39) N-[6-(2,5-dioxo-2,5-dihydro-1H-pyrrol-1-yl)hexanoyl]-L-valyl-N⁵-carbamoyl-N-[4-({[{3-[({[(8S)-8-(chloromethyl)--methyl-6-({5-[2-{pyrrolidin-1-yl}ethoxy]-1H-indol-2-yl}carbonyl)-7,8-dihydro-6H-thieno[3,2-e]indol-4-yl]oxy}carbonyl)(methyl)amino]-2,2-dimethylpropyl}(methy)carbamoyl]ox})meth)phenyl]-L-ornithinamide,
40) N-[6-(2,5-dioxo-2,5-dihydro-1H-pyrrol-1-yl)hexanoyl]-L-valyl-N⁵-carbamoyl-N-[4-({[{3-[({[(8R)-8-(chloromethyl)-1-methyl-6-({5-[2-(pyrrolidin-1-yl)ethoxy]-1H-indol-2-yl}carbonyl)-7,8-dihydro-6H-thieno[3,2-e]indo-4-yl]oxy}carbonyl)methyl)amino]-2,2-dimethylpropyl}methyl)carbamoyl]oxy}methyl)phenyl]-L-ornithinamide,
41) N-[6-(2,5-dioxo-2,5-dihydro-1H-pyrrol-1-yl)hexanoyl]-L-valyl-N⁵-carbamoyl-N-[4-({[(3-{[({(8S)-8-(chloromethyl)-1-methyl-6-[(2E)-3-{5-[2-pyrrolidin-1-yl)ethoxy]-1H-indol-2-yl}prop-2-enoyl]-7,8-dihydro-6H-thieno[3,2-e]indol-4-yl}oxy)carbonyl](methyl)amino}-2,2-dimethylpropyl)methyl)carbamoyl]oxy}methyl)phenyl]-L-ornithinamide,
42) N-[6-(2,5-dioxo-2,5-dihydro-1H-pyrrol-1-yl)hexanoyl]-L-valyl-N⁵-carbamoyl-N-[4-({[(3-{[({(8R-8-(chloromethyl)-1-methyl-6-[(2E)-3-{5-[2-(pyrrolidin-1-yl)ethoxy]-1H-indol-2 yl}prop-2-enoyl]-7,8-dihydro-6H-thieno[3,2-e]indol-4-yl}oxy)carbonyl](methyl)amino}-2,2-dimethylpropyl)(methyl)carbamoyl]oxy}methyl)phenyl]-L-ornithinamide,
43) (2E)-1-[(8S)-8-(chloromethyl)-4-hydroxy-1-methyl-7,8-dihydro-6H-thieno[3,2-e]indol-6-yl]-3-(1H-indol-3-yl)prop-2-en-1-one,
44) N-(2-{[(8R)-8-(chloromethyl)-4-hydroxy-1-methyl-7,8-dihydro-6H-thieno[3,2-e]indol-6-yl]carbonyl}-1-methyl-1H-indo-5-yl)-1-methyl-1H-indole-2-carboxamide,
45) 1-methyl-N-(1-methy-2-{[(3bS,4aR)meth-8-oxo-4a,5-dihydro-4H-cyclopropa[c]thieno[3,2-e]indol-6(8H)-yl]carbonyl}1H-indol-5-yl)-1H-indole-2-carboxamide,
46) N-[6-(2,5-dioxo-2,5-dihydro-1H-pyrrol-1-yl)hexanoyl]-L-phenylalanyl-L-leucyl-N-[4-({[{3-[({[(8S)-8-(chloromethyl)-1-methy-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]glycinamide,
47) N-[6-(2,5-dioxo-2,5-dihydro-1H-pyrrol-1-yl)hexanoyl]-L-phenylalanyl-L-leucyl-N-[4-({[{3-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)methyl)amino]-2,2-dimethylpropyl}(methyl)carbamoyl]oxy}methyl)phenyl]glycinamide,
48) N-[6-(2,5-dioxo-2,5-dihydro-1H-pyrrol-1-yl)hexanoyl]-L-phenylalanyl-L-leucyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]glycinamide,
49) N-[6-(2,5-dioxo-2,5-dihydro-1H-pyrrol-1-yl)hexanoyl]-L-phenylalanyl-L-leucyl-N-[4-({[{2-[({[(8S)-8-(chloromethyl)-1-methyl-({5-[2-(pyrrolidin-1-yl)ethoxy]-1H-indol-2-yl}carbonyl)-7,8-dihydro-6H-thieno[3,2-e]indol-4-yl]oxy}carbonyl)(methy)amino]ethyl}(methyl)carbamoyl]oxy}methy)phenyl]glycinamide,
50) L-valyl-N⁵-carbamoyl-N-[4-({[{2-[({[(8S)-8-(chloromethyl)-1-methyl-6-({5-[({5-[2-pyrrolidin-1-yl)ethoxy]-1 H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-omithinamide,
51) L-valyl-N⁵-carbamoyl-N-[4-({[{2-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)methyl)amino]ethyl}(methyl)carbamoyl]oxy}methyl)phenyl]-L-ornithinamide,
52) N-[6-(2,5-dioxo-2,5-dihydro-1H-pyrrol-1-yl)hexanoyl]-L-valyl-N⁵-carbamoyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-omithinamide,
53) N-[19-(2,5-dioxo-2,5-dihydro-1H-pyrrol-1-yl)-17-oxo-4,7,10,13-tetraoxa-16-azanonadecan-1-oyl]-L-valyl-N⁵-carbamoyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-omithinamide and
54) N-[6-(2,5-dioxo-2,5-dihydro-1H-pyrrol-1-yl)hexanoyl]-L-valyl-N⁵-carbamoyl-N-[4-({[{2-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methy)amino]ethyl}(methyl)carbamoyl]oxy}methyl)phenyl]-L-ornithinamide.

For a reference to any specific compound of the formula (I), (II), (III) or (IV) of the invention, optionally in the form of a pharmaceutically acceptable salt, see the experimental section and claims.

The present invention also provides a process for the preparation of a compound of formula (I), (II), (III) or (IV) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

All those with ordinary skills in the art will appreciate that any transformation performed according to said methods may require standard modifications such as, for instance, protection of interfering groups, change to other suitable reagents known in the art, or make routine modifications of reaction conditions.

The present invention provides a process for the preparation of a compound of formula (I) or (III) as defined above, characterized in that the process comprises the following step:

a) converting a compound of formula (II) or (IV)

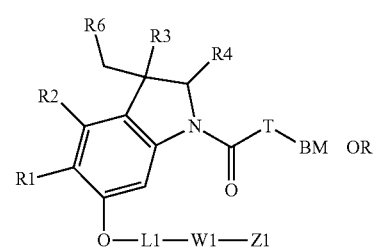
(II)

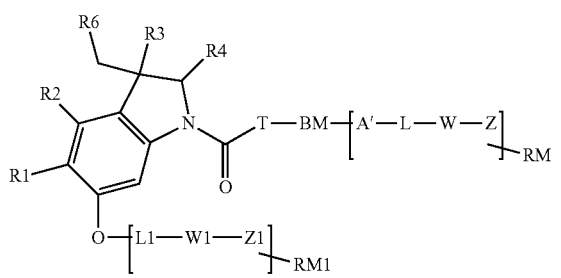
(IV)

wherein
L$_1$ is hydrogen, W1, Z1 and RM1 are null, and
R1, R2, R3, R4, R6, T, BM, A', L W, Z and RM are as defined above, to give a compound of formula (I) or (III), respectively as defined above, and the pharmaceutically acceptable salts thereof.

Accordingly, the preparation of a compound of formula (I) or (III) is depicted in Scheme 1 below:

Scheme 1

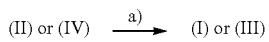

According to step a) the reaction is performed by well known procedures reported in the art (see for example Boger, D. L.; *J. Am. Chem. Soc.* 1996, 118, 2301-2302). An example, that is not intended to limit the method, is the use of basic conditions such as e.g. the use of TEA, NaHCO$_3$ or DBU. The reaction is performed in DCM or DMF or a mixture of them, at a temperature ranging from 20° C. to reflux and for a time ranging from 30 minutes to about 24 hours.

The present invention also provides a process for the preparation of a compound of formula (II) as defined above, i.e. a compound of formula (II)' wherein L1 is hydrogen and a compound of formula (II)" wherein L1 is not hydrogen, characterized in that the process comprises the following steps:
b) reacting a compound of formula (XVI)

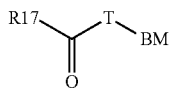
(XVI)

wherein R17 is halogen, OH, or an activating moiety of the carboxylic group, e.g. activated esters, T is as defined above and BM is a binding moiety of formula (V) as defined above, with a compound of fsrmula (XVII)

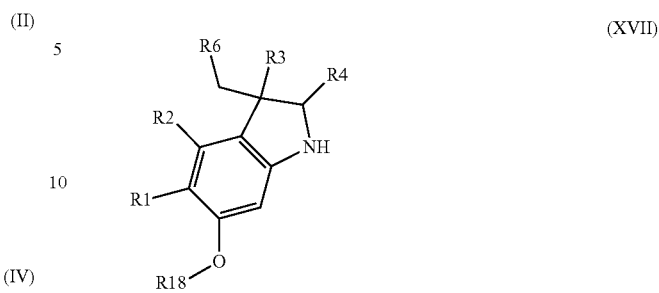
(XVII)

wherein R18 is hydrogen or a protecting group and R1, R2, R3, R4 and R6 are as defined above;
optionally
c) removing the protection if present and reacting the resultant compound of formula (II)'

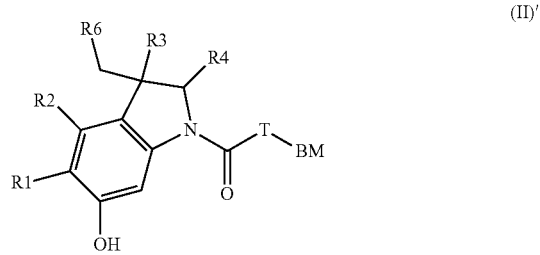
(II)' wherein R1, R2, R3, R4, R6, T and BM are as defined above, with a compound of formula (XVIII)

R19-L1-W1-Z1 (XVIII)

wherein R19 is null, hydrogen, an activating moiety of the NH group, preferably tosyl, or R17, wherein R17 is as defined above, and
L1, W1 and Z1 are as defined above and at least one of them is not null,
to give a compound of formula (II)"

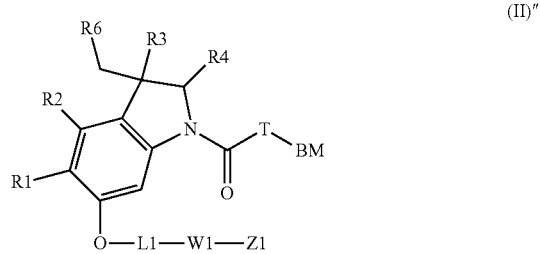
(II)"

wherein L1 is as defined above except hydrogen, at least one of L1, W1 and Z1 is not null,
and R1, R2, R3, R4, R6, T and BM are as defined above, and the pharmaceutically acceptable salts thereof.

Accordingly, the preparation of a compound of formula (II) is depicted in Scheme 2 below:

Scheme 2

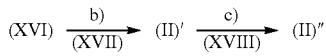

The present invention also provides a process for the preparation of a compound of formula (IV) as defined above, i.e. a compound of formula (IV)' wherein A' is A and L1 is hydrogen and a compound of formula (IV)" wherein A' is A and L1 is not hydrogen, characterized in that the process comprises the following steps:

d) reacting a compound of formula (XIX)

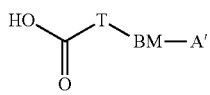
(XIX)

wherein A' is A, wherein A is as defined above,
T is as defined above, and
BM is a binding moiety of formula (V)' as defined above,
with a compound of formula (XX)

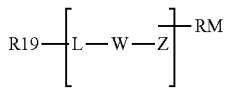
(XX)

wherein R19 is as defined above, and
L, W, Z and RM are as defined above and at least one of them is not null;

e) reacting the resultant compound of formula (XXI)

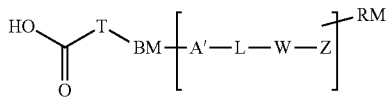
(XXI)

wherein A' is A, wherein A is as defined above, and
T, BM, L, W, Z and RM are as defined above,
with a compound of formula (XVII)

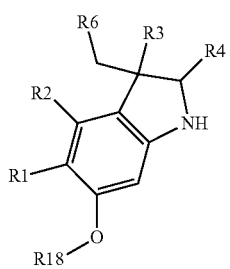
(XVII)

as defined above;

optionally
f) reacting the resultant compound of formula (IV)'

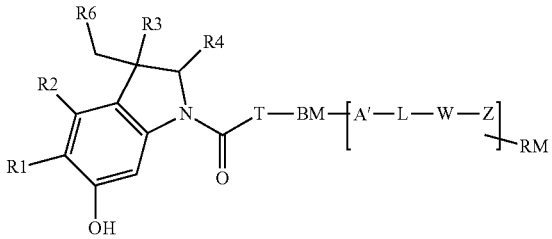
(IV)' wherein A' is A, wherein A is as defined above,
L, W, Z and RM are as defined above, and at least one of them is not null,
and R1, R2, R3, R4, R6, T and BM are as defined above,
with a compound of formula (XX)'

R19—[-L1-W1-Z1-]—$^{RM1}$  (XX)

wherein R19 is as defined above, L1 is as defined above except hydrogen, and W1, Z1 and RM1 are as defined above, and at least one of them is not null, to give a compound of formula (IV)"

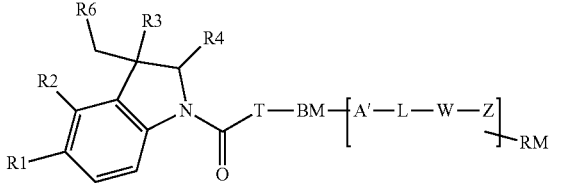
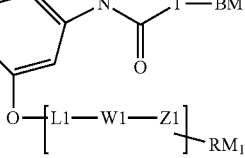
(IV)"

wherein L1 is as defined above except hydrogen,
W1, Z1 and RM1 are as defined above, and at least one of them is not null
A' is A, wherein A is as defined above,
L, W, Z and RM are as defined above, and
R1, R2, R3, R4, R6, T and BM are as defined above,
and the pharmaceutically acceptable salts thereof.

The present invention also provides a process for the preparation of a compound of formula (IV) as defined above, i.e. a compound of formula (IV)' as defined above, and a compound of formula (IVa)" wherein A' is A, wherein A is a saturated group selected from OH, NH$_2$ and COOH, and L1 is not hydrogen, characterized in that the process comprises the following steps:

d') reacting a compound of formula (XIX) with a compound of formula (XVII) as defined above;

e') reacting the resultant compound of formula (XV)

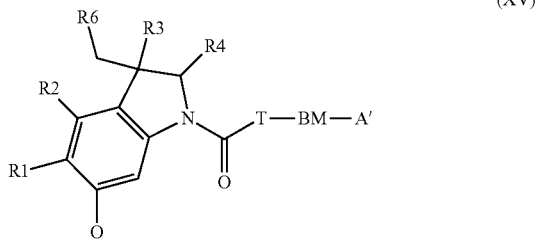

(XV)

wherein A' is A, wherein A is a saturated group selected from OH, NH$_2$ and COOH
and
R1, R2, R3, R4, R6, T and BM are as defined above,
with the compound of formula (XX) as defined above;
optionally
   f) reacting the resultant compound of formula (IV)'

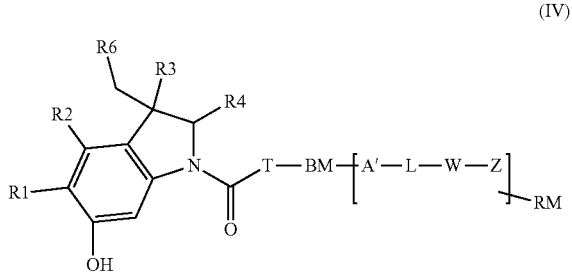

(IV)' wherein A' is A, wherein A is as defined above, and
R1, R2, R3, R4, R6, T, BM, L, W, Z and RM are as defined above
with a compound of formula (XX)' defined above so to yield a compound of formula (IV)" as defined above, and the pharmaceutically acceptable salts.
or
e") reacting the compound of formula (XV) as defined above, with the compound of formula (XX)' as defined above;
optionally
   f") reacting the resultant compound of formula (IVa)"

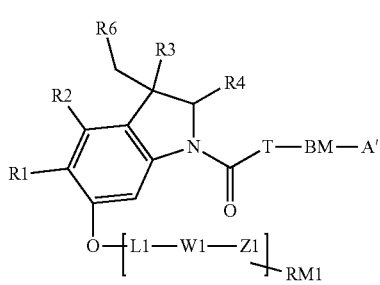

(IVa)"

wherein L1 is as defined above except hydrogen, L1, W1, Z1 and RM1 are as defined above and at least one of them is not null,
A' is A, wherein A is a saturated group selected from OH, NH$_2$ and COOH and R1, R2, R3, R4, R6, T and BM are as defined above, with the compound of formula (XX) as defined above, to give a compound of formula (IV)" as defined above, and the pharmaceutically acceptable salts.

Accordingly, the preparation of a compound of formula (IV), i.e. a compound of formula (IV)', (IV)" or (IVa)" as defined above, is depicted in Scheme 3 below:

Scheme 3

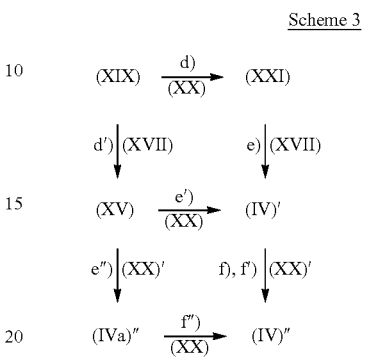

According to step c), d), f) e'), f'), e") and f") the coupling is performed in a organic solvent, preferably DMF, in presence of a condensing agent such as for example DCC, EDC (for general coupling reagents see e.g. Amino Acids, Peptides and Proteins in Organic Chemistry: Building Blocks, Catalysis and Coupling Chemistry, Volume 3; Andrew B. Hughes, Ayman El-Faham, Fernando Albericio). See also specific chemical conditions reported in the experimental part below.

According to b), e), d') the coupling reaction is preferably carried out at a temperature ranging from 20° C. to reflux, in presence optionally of a base, and for a time ranging from 30 minutes to about 24 hours.

Compounds of formula (XVII) and (XIX) are known or can be prepared by methods known to the expert in the art or as reported in GB2344818 cited above or J. Med. Chem. 2003, (46) page 634-637.

Compounds of formula (XVI), (XVIII), (XX) and (XX)' are known or can be prepared by methods known to the expert in the art or as reported in Anticancer Agents in Med Chem 2008, (8) page 618-637 or in WO2010(009124.

The present invention also provides a process for the preparation of a compound of formula (IV) as defined above, i.e. a compound of formula (IV)'" wherein A' is null and L1 is not hydrogen, characterized in that the process comprises the following step:
e'") reacting a compound of formula (II)'

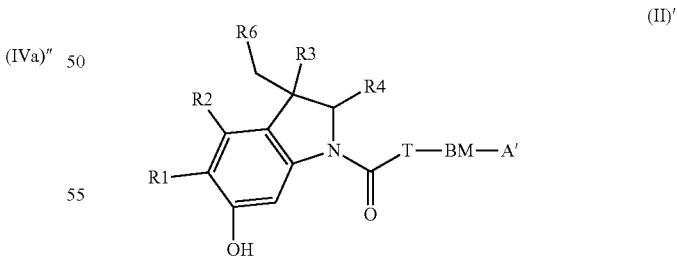

(II)' wherein A' is null,
R$_1$, R$_2$, R$_3$, R$_4$, R$_6$ and T are as defined above and
BM is a binding moiety of formula (V) as defined above,
with a compound of formula (XX)'

R19—[L1-W1-Z1—]$^{RM_1}$    (XX)' wherein L1 is as defined above but not hydrogen and R19, W1, Z1 and RM1 are as defined above, to give a compound of formula (IV)'"

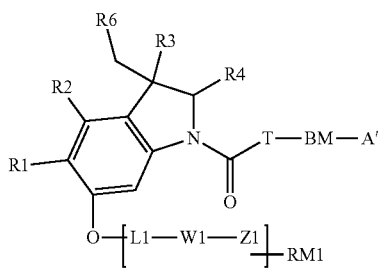

(IV)″ wherein A' is null,

L1 is as defined above except hydrogen,

R1, R2, R3, R4, R6, T and BM are as defined above, and

W1, Z1 and RM1 are as defined above and at least one of them is not null, and the pharmaceutically acceptable salts thereof.

Accordingly, the preparation of a compound of formula (IV), wherein A' is null, is depicted in Scheme 4 below.

Scheme 4

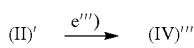

According to step e''') the coupling is performed as described under e'') above.

From all of the above, it is clear to the skilled person that when preparing the compounds of formula (I), (II), (III) and (IV) according to any one of the aforementioned process variants, optional functional groups within the starting materials or the intermediates thereof that could give rise to unwanted side reactions need to be properly protected according to conventional techniques. Likewise, the conversion of these latter into the free deprotected compounds may be carried out according to known procedures.

As it will be readily appreciated, if the compounds of formula (I), (II), (III) and (IV) prepared according to the process described above are obtained as mixture of isomers, their separation using conventional techniques into the single isomers of formula (I), (II), (III) and (IV) is within the scope of the present invention.

Preferably a compound of formula (II) wherein L1 is as defined above except hydrogen or a compound of formula (IV) wherein RM and/or RM1 are not null, and R1, R2, R3, R4, R6, T, BM, A', L, W, Z, L1, W1 and Z1 are as defined above, is reacted g) with a compound of formula (XXII)

R17-RM    (XXII)

wherein R17 is as defined above and RM is as defined above but not null, to give the corresponding compound of formula (IV) wherein RM is as defined above but not null, then optionally h) with a compound of formula (XXII)'

R17-RM1    (XXII)' wherein R17 is as defined above, and RM1 is as defined above but not null, to give the corresponding compound of formula (IV) wherein RM1 is as defined above but not null.

It is important to underline that the steps described under g) and h) may optionally occurs in reverse order, i.e. step h) first and then step g).

According to step g) and h) the coupling is performed as described under b) above.

Compounds of formula (XXII) and (XXII)' are commercially available or are known compounds or can be prepared by methods known to the expert in the art or as reported in Anticancer Agents in Med Chem 2008, (8) page 618-637 or in WO2010009124.

Preferably a compound of formula (XIX), wherein A' is —OH and T and BM are as defined above, is reacted i) with a compound of formula (XX)

wherein R19 is null,

L is a group of formula (Xf') or (Xg')

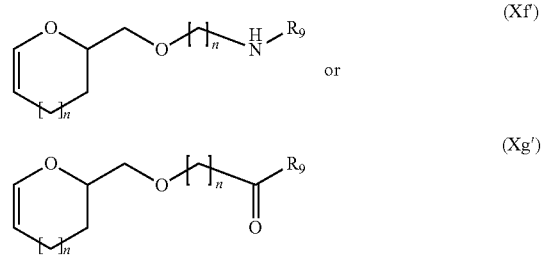

wherein R9 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and W, Z and RM are null or R9 is null and at least one of W, Z or RM is not null, to give a compound of formula (XI)

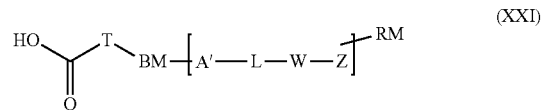

wherein A' is —O—, L is a group of formula (Xf) or (Xg), T, W, Z and RM are as defined above and BM is a group of formula (V)';

or j) with a compound of formula (XX)

Wherein R19 is null,

L is a group of formula (Xh') or (Xi')

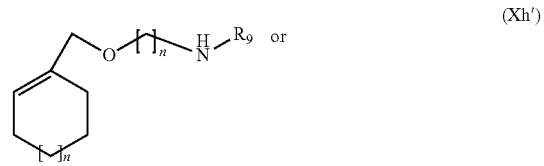

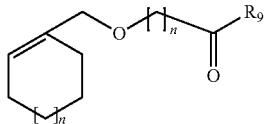

(Xi′)

wherein R9 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and
W, Z and RM are null
or
R9 is null and
at least one of W, Z or RM is not null,
to give a compound of formula (XXI)

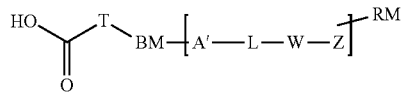

(XXI)

wherein A' is —O—, L is a group of formula (Xh) or (Xi) and T, BM, L, W, Z and RM are as defined above; or
k) with a compound of formula (XX)

(XX)

wherein R19 is an activating NH group preferably tosyl,
L is a group of formula —NHCOR$_9$(Xa), —NHCONH—R$_9$(Xb), —NHCOO—R$_9$(Xc), or —NH—R$_9$ (Xd);
wherein R9 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and
W, Z and RM are null
or
R9 is null and
at least one of W, Z or RM is not null,
to give a compound of formula (XXI)

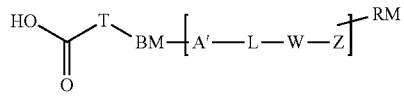

(XXI)

wherein A' is —O—, L is a group of formula (Xa) to (Xd) and T, BM, W, Z and RM are as defined above;
or
l) with a compound of formula of formula (XX)

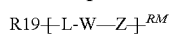

(XX)

wherein R19 is R17 wherein R17 is —OH,
L is a group of formula (Xe)

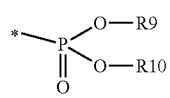

(Xe)

wherein
R9 and R10 are, each independently, hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and
W, Z and RM are null
or
one of R9 or R10 is null and
at least one of W, Z or RM is not null,
to give a compound of formula (XXI)

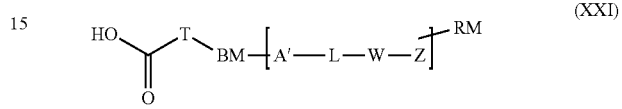

(XXI)

wherein A' is —O—, L is a group of formula (Xe) and T, BM, W, Z and RM are as defined above.

According to step i) and j) the reaction is carried in an organic solvent, preferably DCM or DMF, in presence of PTSA at a temperature ranging from 20° C. to reflux and for a time ranging from 30 minutes to about 24 hours. Removal of the protecting group is performed using known procedure reported in the literature (see e.g. Protective Groups in Organic Synthesis; Theodora W. Greeen, Peter G. M. Wuts).

According to step k) the reaction is performed in a organic solvent, preferably ether, dioxane or a mixture of them with LiHMDS at a temperature ranging from −10° C. to 50° C. and for a time ranging from 30 minutes to about 24 hours. Removal of the protecting group is performed using known procedure reported in the literature (see e.g. Protective Groups in Organic Synthesis; Theodora W. Greeen, Peter G. M. Wuts).

According to step l) the reaction is performed in an organic solvent, preferably DCM, THF, $CH_3CN$ or $CCl_4$, optionally in presence of a base, preferably DIPEA, at a temperature ranging from −10° C. to 50° C. and for a time ranging from 30 minutes to about 24 hours.

Preferably a compound of formula (XIX) wherein A' is —OH or —$NH_2$, and T and BM are as defined above, is reacted
m) with a compound of formula (XX)

(XX)

wherein R19 is R17 wherein R17 is an activating moiety of the carboxylic group, preferably pyrrolidin-2,5-dione-1yl,
L is a group of formula (Xj) or (Xk)

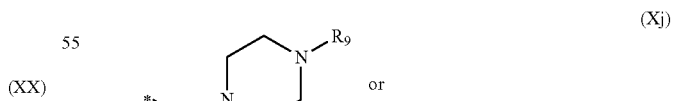

(Xj)

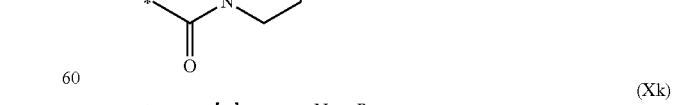

(Xk)

wherein R9 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and W, Z and RM are null or R9 is null and at least one of W, Z or RM is not null, to give a compound of formula (XXI)

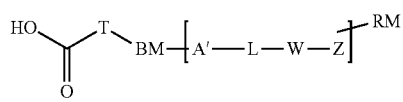
(XXI)

wherein A' is —O— or —NH, L is a group of formula (Xj) or (Xk) and T, BM, W, Z and RM are as defined above.

According to step m) the coupling reaction is performed in a organic solvent, preferably DCM, in basic conditions, e.g. TEA, DMAP. The reaction is carried out at a temperature ranging from 0° C. to reflux and for a time ranging from 30 minutes to about 24 hours.

Preferably a compound of formula (XIX) wherein A' is —COOH, and T and BM are as defined above, is reacted n) with a compound of formula (XX)

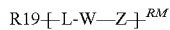
(XX)

wherein R19 is hydrogen,

L is a group of formula (Xm) or (Xn)

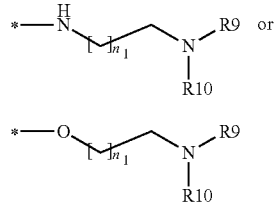
(Xm)

(Xn)

wherein

R9 and R10 are, each independently, hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and W, Z and RM are null or one of R9 or R10 is null and at least one of W, Z or RM is not null, to give a compound of formula (XXI)

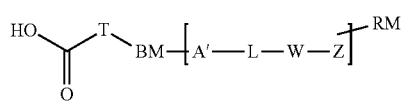
(XXI)

wherein A' is —CO—, L is a group of formula (Xm) or (Xn) and T, BM, W, Z and RM are as defined above; or o) with a compound of formula (XX)

wherein L is null,

W is a group of formula (XIa) to (XIe), (XIh) to (XIj)

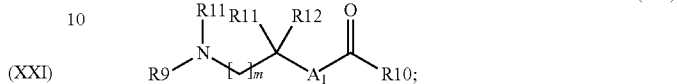
(XIa)

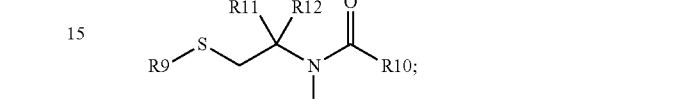
(XIb)

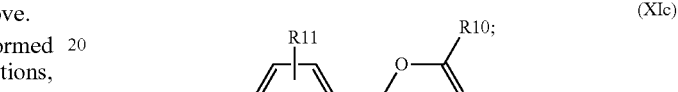
(XIc)

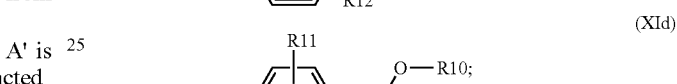
(XId)

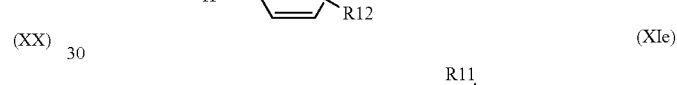
(XIe)

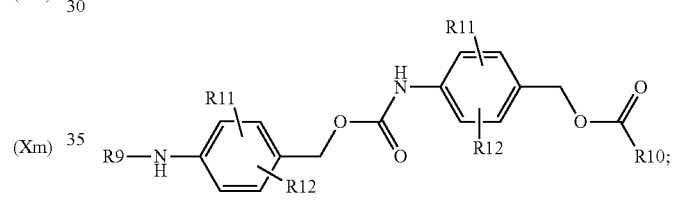
(XIf)

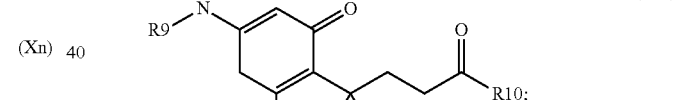
(XIh)

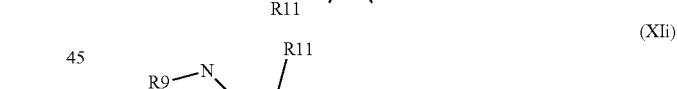
(XIi)

or

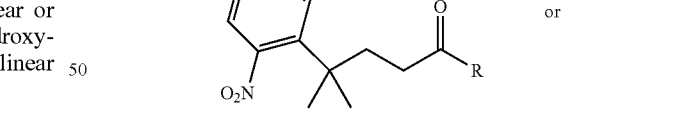

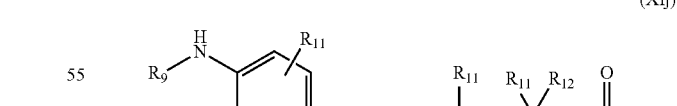
(XIj)

wherein R9 is hydrogen,

R10 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and W, Z and RM are null or R10 is null and at least one of W, Z or RM is not null, R11 and R12 are as defined above, $A_1$ is —CH—, —CH$_2$N(R12)- or —NR12-, wherein R12 is as defined above, to give a compound of formula (XXI)

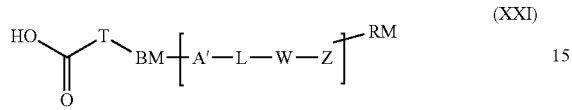
(XXI)

wherein A' is —CO—, L is null, W is a group of formula (XIa) to (XIe), (XIh) and (XIj), T, BM, W, Z and RM are as defined above.

According to step n) the reaction is performed in a organic solvent, preferably DCM, in basic conditions e.g. TEA and optionally in presence of a condensing agent such as for example DCC, EDC, at a temperature ranging from 0° C. to reflux and for a time ranging from 30 minutes to about 24 hours.

According to step o) the coupling reaction is performed using conditions well known in the literature (see e.g. Scott, C. J. et al. *J. Med. Chem.* 2005, 48, 1344-1358; Amino Acids, Peptides and Proteins in Organic Chemistry: Building Blocks, Catalysis and Coupling Chemistry, Volume 3; Andrew B. Hughes, Ayman El-Faham, Fernando Albericio).

Preferably a compound of formula (XIX) wherein A' is —OH or —NH$_2$, and T and BM as defined above, is reacted p) with a compound of formula (XX)

(XX)

wherein R19 is null,

L is null,

W is a group of formula (XIa) to (XIj)

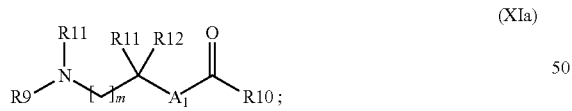
(XIa)

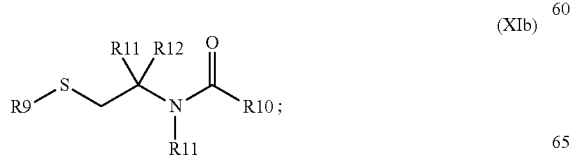
(XIb)

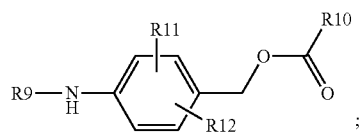
(XIc)

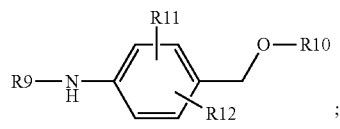
(XId)

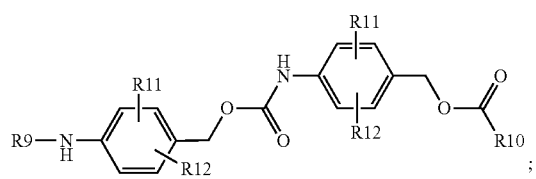
(XIe)

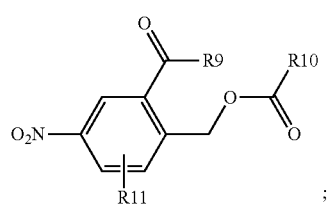
(XIf)

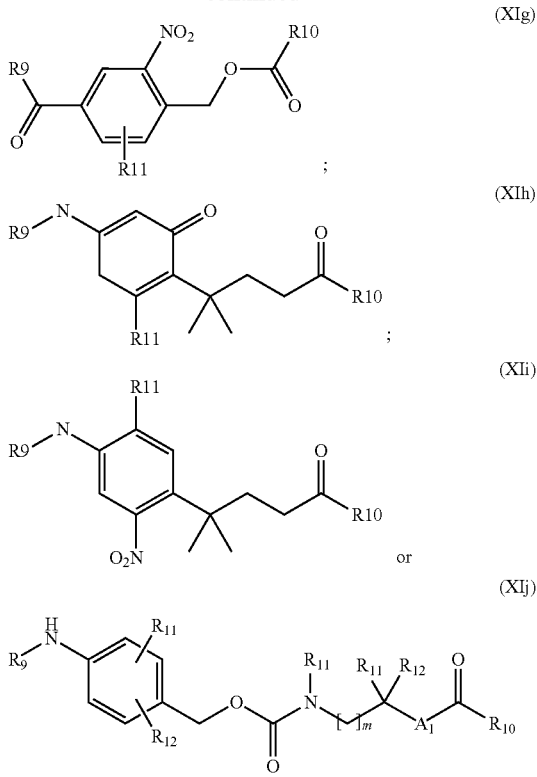

wherein R10 is —OH,
R9 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and
W, Z and RM are null
or
R9 is null and
at least one of W, Z or RM is not null,
R11, R12, m and $A_1$ are as defined above,
to give compound of formula (XXI)

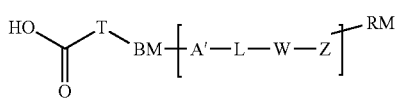

wherein A' is —O— or —NH—, L is null, W is a group of formula (XIa) to (XIi), T, BM, W, Z and RM are as defined above.

According to step p) the coupling reaction is performed as described under o) above.

Steps i) to m) and p) can also be used to convert compounds of formula (IV)' to compounds of formula (IV)" by reaction with compounds of formula (XX)' (step f) or to convert compounds of formula (XV) to compounds of formula (IV)''' by reaction with compounds of formula (XX)' (step e") or to convert compounds of formula (II)' to compounds of formula (II)" by reaction with compounds of formula (XVIII) (step c) or to convert compounds of formula (XV) to compounds of formula (IV)' by reaction with compounds of formula (XX) (step e') or to convert compounds of formula (IV)''' to compounds of formula (IV)" by reaction with compounds of formula (XX) (step f").

Pharmacology

The compounds of the present invention are useful as antitumor agents.

A mammal, e.g. a human or animal, may therefore be treated by a method comprising administering thereto a pharmaceutically effective amount of a compound of formula (I), (II), (III) or (IV).

The condition of the human or animal may be ameliorated or improved in this way.

The evaluation of the cytotoxicity of the compounds of formula (I), (II), (III), or (IV) is assessed as described below.

In Vitro Cell Proliferation Assay

A2780 human ovarian and MCF7 human breast cancer cells (1250 cells/well) were seeded in white 384 well-plates in complete medium (RPMI1640 or EMEM plus 10% Fetal bovine serum) and treated with compounds dissolved in 0.1% DMSO, 24 h after seeding. The cells were incubated at 37° C. and 5% $CO_2$ and after 72 h the plates were processed using CellTiter-Glo assay (Promega) following the manufacturer's instruction.

CellTiter-Glo is a homogenous method based on the quantification of the ATP present, an indicator of metabolitically active cells. ATP is quantified using a system based on luciferase and D-luciferin resulting into light generation. The luminescent signal is proportional to the number of cells present in culture.

Briefly, 25 μL/well of reagent solution are added to each well and after 5 minutes shaking microplates are read by a luminometer. The luminescent signal is proportional to the number of cells present in culture.

Representative compounds of the invention of formula (I) or (II) were tested in the specific in vitro cell proliferation assay described above.

All the tested compounds have an $IC_{50}$ value<0.5 μM (<500 nM) in A2780 human ovarian cancer cells.

In particular, Compd. 7, 9, 23, 6, 1 and 5 have $IC_{50}$ value<50 nM; Compd. 22, 17 and 20 have an $IC_{50}$ value<0.1 nM; Compd. 18, 8 and 37 have an $IC_{50}$ value<0.01 nM.

As can be appreciated by the skilled person, all these representative compounds are thus particularly advantageous in antitumor therapy.

Furthermore the functionalized compounds of formula (III) or (IV) of the present invention are suitable to be conjugated.

The ability of the functionalized derivatives of formula (III) or (IV) to be conjugated has been assessed by conjugating them with a nucleophilic group such as the SH group of the cysteine aminoacid.

Preparation of a Conjugate 2 nmol of cysteine (MW 121 Da) have been reacted with 2 nmol of a functionalized compound of formula (IV), i.e. Compd. 54 (MW 1221 Da).

The reaction was incubated for 1 h at 21° C. in presence of Borate buffer 50 mM pH8, DTPA 2 mM, NaCl 50 mM, obtaining conjugate A1 (m/z=1343 (MH+)) then was analyzed by HPLC ESI-MS using a reversed phase HPLC method (PLRP-S column 1000 A 8 uM 150×2.1 mm) on a 1100 Agilent HPLC instrument coupled with an Agilent 1946 single quadrupole mass spectrometry detector with an orthogonal ESI source.

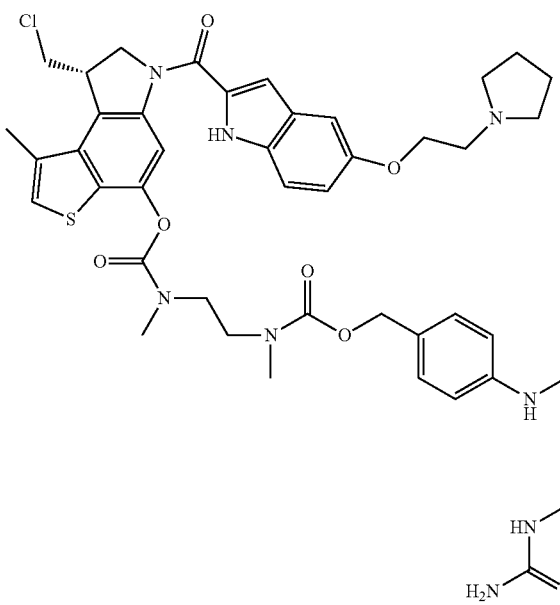
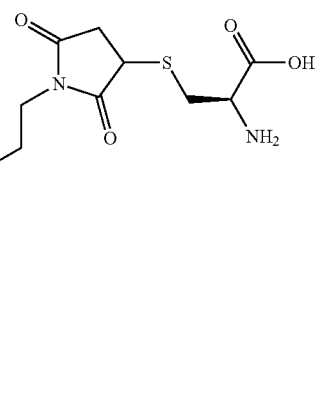

Conjugate A1
ESI MS: m/z = 1343 (MH+)

RELEASE OF A DRUG MOIETY FROM A CONJUGATE

Figure 1:
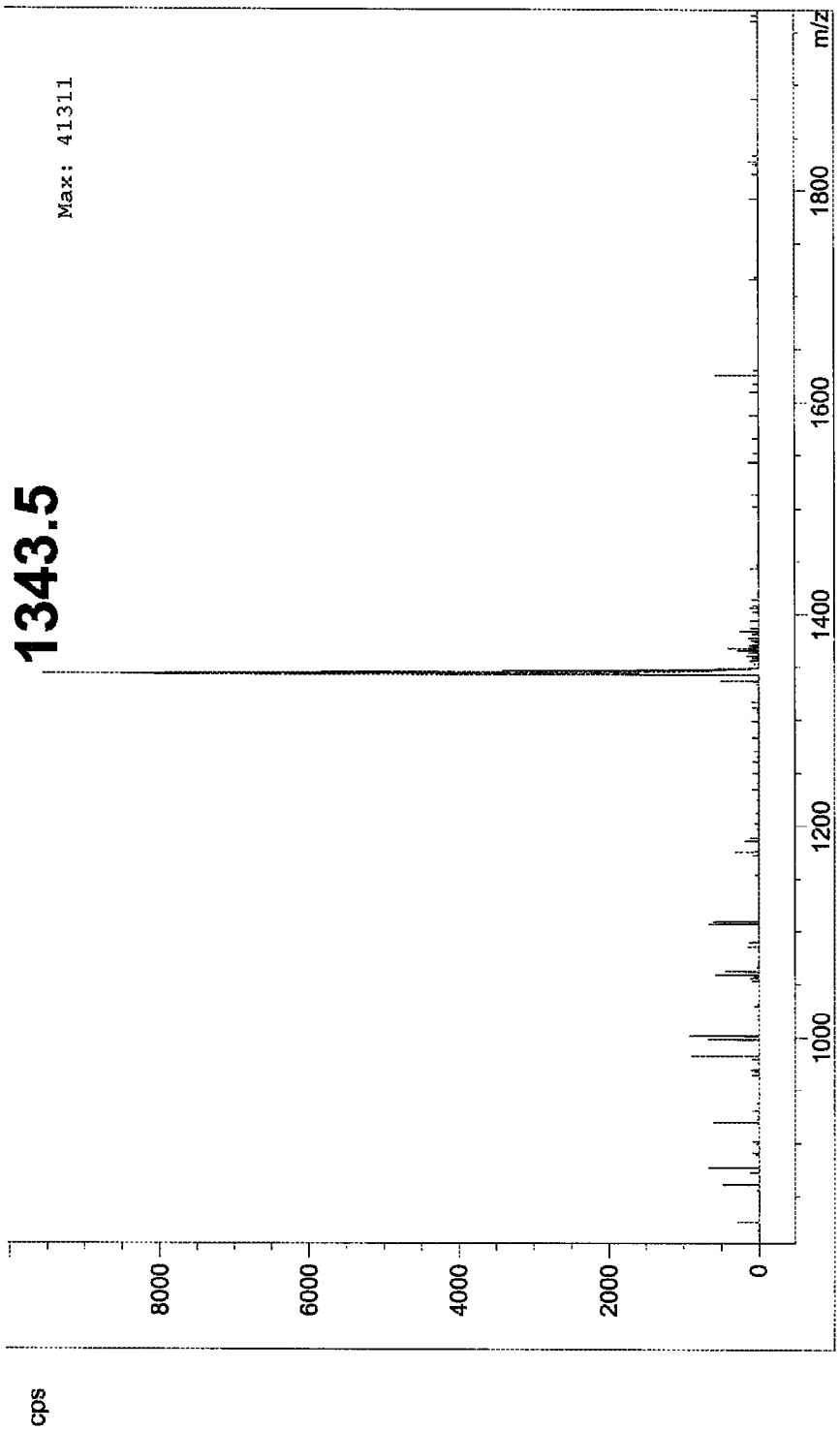
FIG. 1 shows the mass spectrum of the conjugate A1 and reports the molecular weight (m/z) on the x axis while intensity expressed as counts per second (cps) is reported on the y axis.
Figure 2:
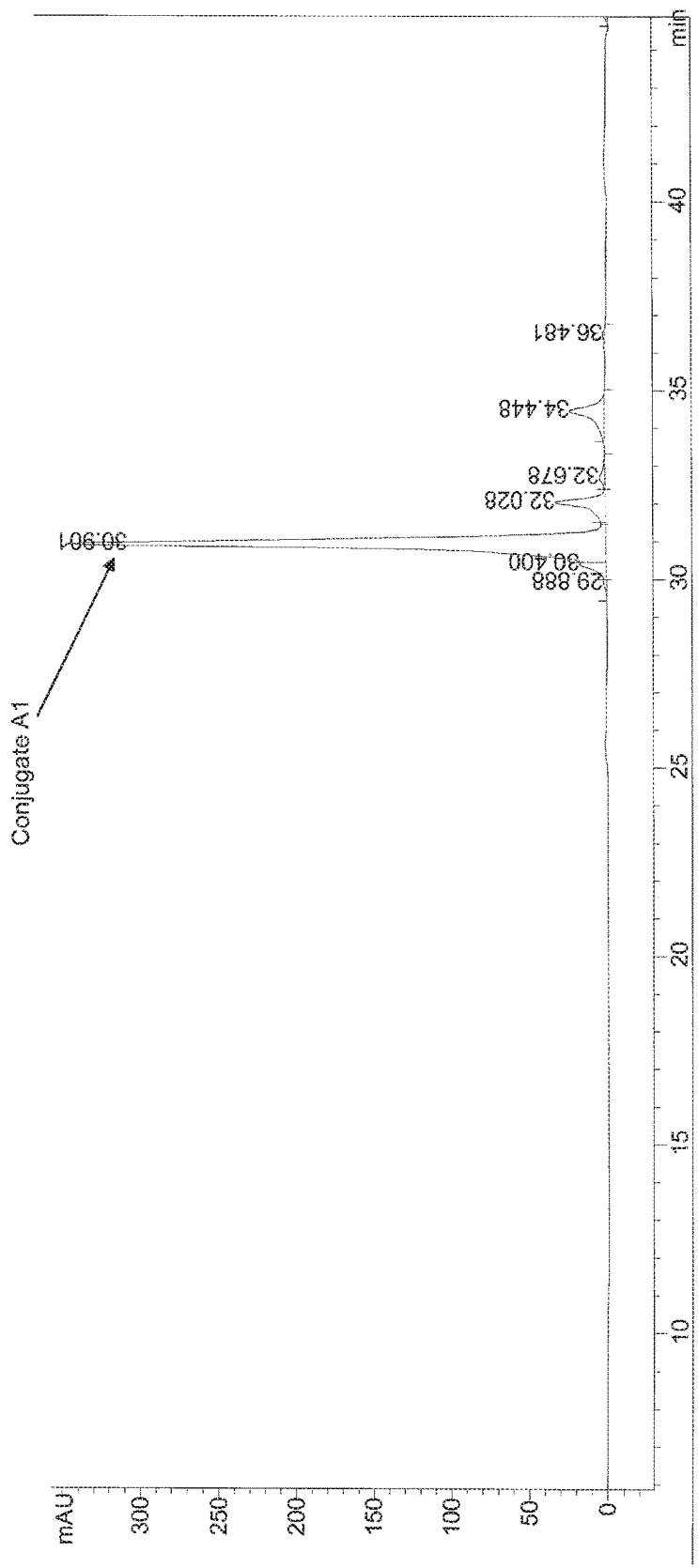
FIG. 2 shows the HPLC profile of the conjugate A1 and reports the time (min) on the x axis while UV absorbance (mAU) is reported on the y axis.
Figure 3:
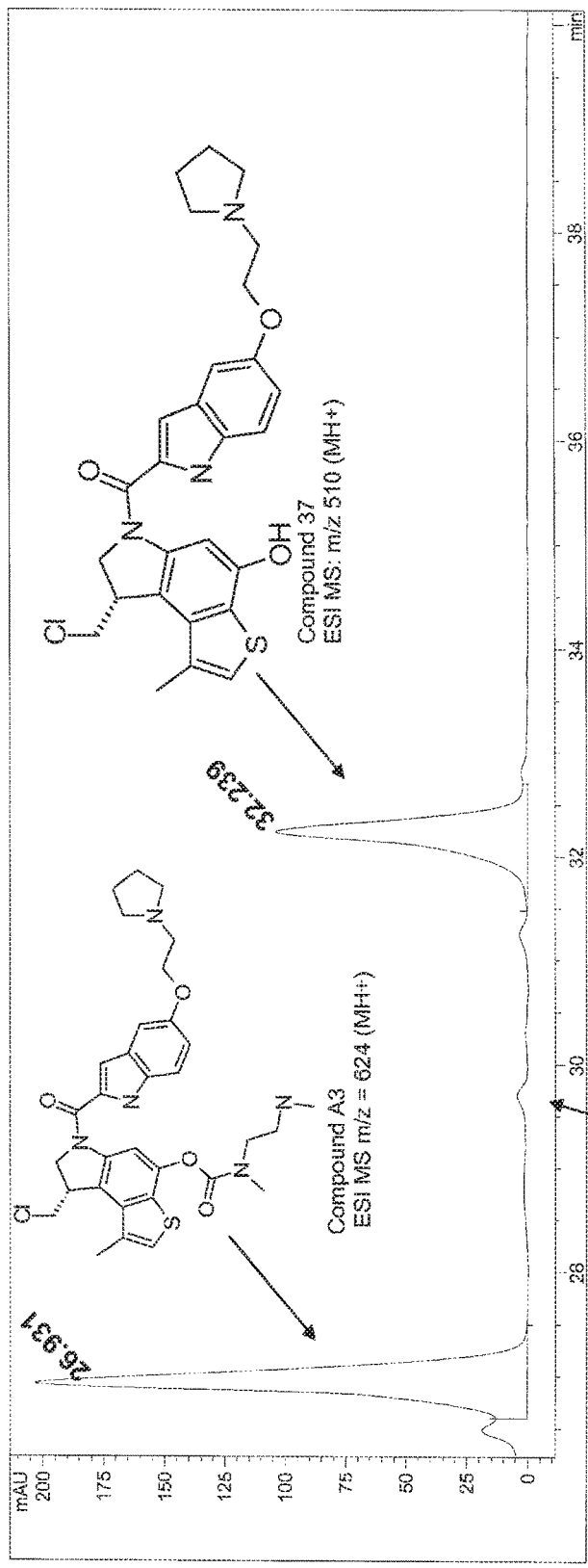
FIG. 3 shows the HPLC profile after 2 h treatment of conjugate A1 with cathepsin and reports the time (min) on the x axis while UV absorbance (mAU) is reported on the y axis.
Figure 4A:
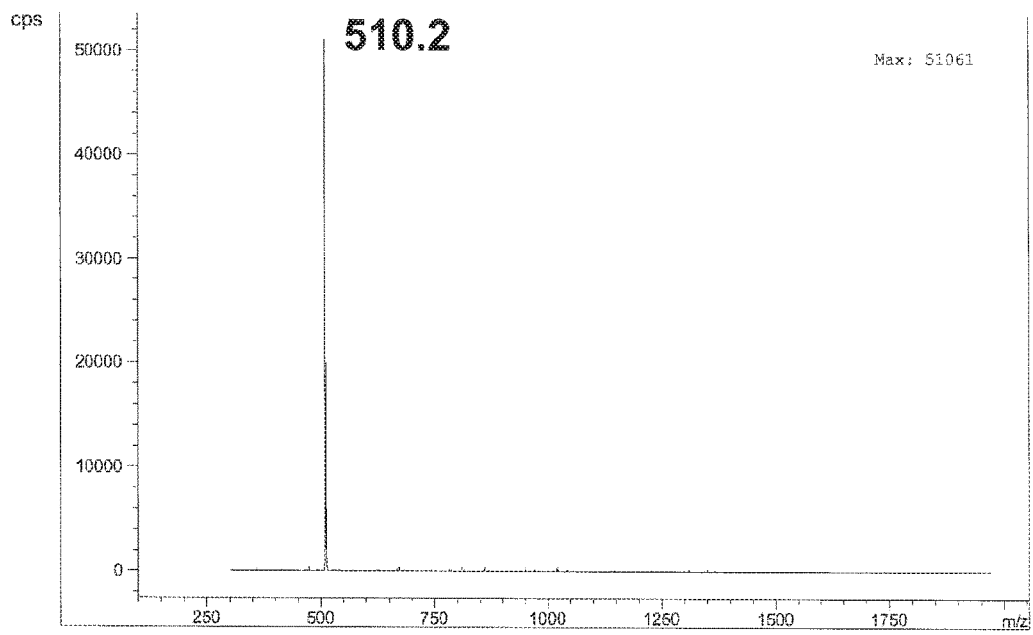
FIG. 4a shows the mass spectrum of the released Compd. 37 and reports the molecular weight (m/z) on the x axis while intensity expressed as counts per second (cps) is reported on the y axis.
Figure 4B:
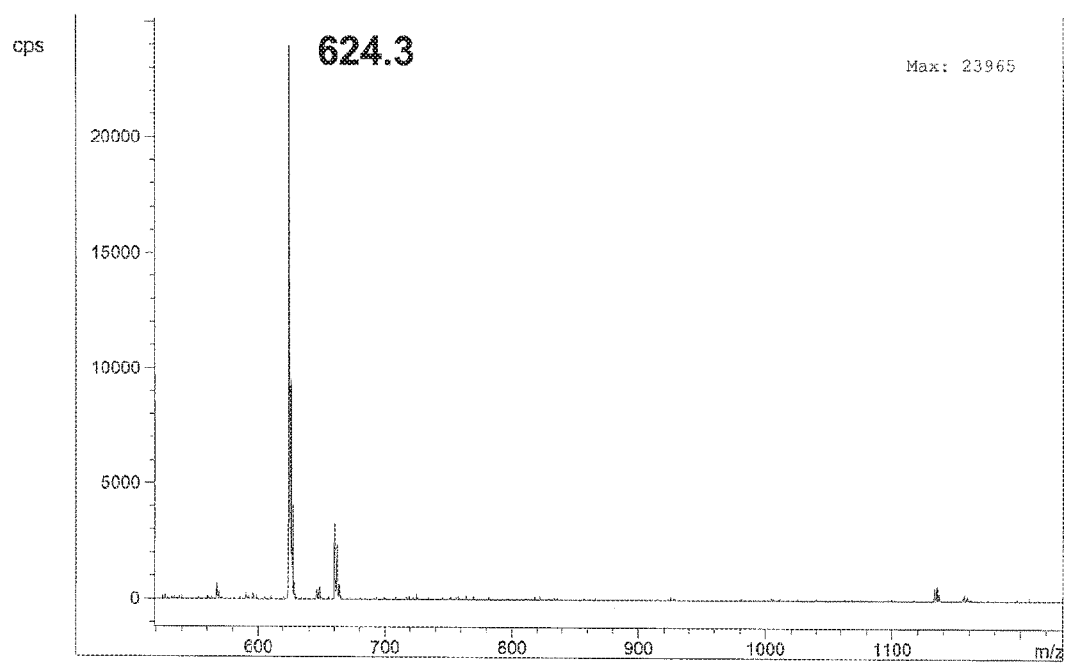
FIG. 4b shows the mass spectrum of the released Compound A3, a precursor of 37, and reports the molecular weight (m/z) on the x axis while intensity expressed as counts per second (cps) is reported on the y axis.

As an example, that is not intended to limit the scope of the invention, the release of a compound of formula (II) from the conjugate was performed in presence of cathepsin as reported below.

The conjugate A1 was incubated with 0.2 unit of cathepsin B in sodium acetate buffer pH 5.5 and 1 mM Cys for 2 hours at 40° C.

Disappearance of the conjugate A1 and release of the corresponding compound of formula (II), i.e. compd. 37, as well as of its precursor A3, confirms the breaking of the Z peptidic linker of the conjugate.

Complete release of the compound of formula (II) from the conjugate has been observed by HPLC ESI-MS analysis.

The compounds of the present invention can be administered either as single agents or, alternatively, in combination with known anticancer treatments such as radiation therapy or chemotherapy regimen, in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, rasraf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I), (II), (III) or (IV) may be used sequentially with known anticancer agents when a combination formulation is inappropriate.

The compounds of formula (I), (II), (III) or (IV) of the present invention, suitable for administration to a mammal, e.g., to humans, can be administered by the usual routes and the dosage level depends upon the age, the weight, the conditions of the patient and the administration route.

For example, a suitable dosage adopted for oral administration of a compound of formula (I) may range from about 1 to about 300 mg per dose, from 1 to 5 times daily. The compounds of the invention can be administered in a variety of dosage forms, e.g., orally, in the form of tablets, capsules, sugar or film coated tablets, liquid solutions or suspensions; rectally in the form of suppositories; parenterally, e.g., subcutaneously, intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain, as a carrier, sterile water or preferably they may be in the form of sterile, aqueous, isotonic, saline solutions or they may contain propylene glycol as a carrier. The suppositories may contain, together with the active compound, a pharmaceutically acceptable carrier, e.g. cocoa butter, polyethylene glycol, a polyoxyethylene sorbitan fatty acid ester surfactant or lecithin.

With the aim at better illustrating the present invention, without posing any limitation to it, the following examples are now given.

EXAMPLES

The synthetic preparation of some compounds of formula (I) of the invention is described in the following examples. The compounds of the present invention, as prepared according to the following examples, were also characterized by $^1$H-NMR and/or by Exact mass data ESI(+).

$^1$H-NMR spectra were recorded at a constant temperature of 25° C. on a Varian INOVA 500 spectrometer (operating at 499.8 MHz for $^1$H, 125.8 for $^{13}$C and 50.6 MHz for $^{15}$N) and equipped with 5 mm $^1$H{$^{13}$C, $^{15}$N} z axis PFG Indirect Detection Cold-Probe or alternatively with 5 mm $^1$H {$^{13}$C-$^{15}$N} z axis PFG Triple Resonanace Probe.

Chemical shifts were referenced with respect to the residual solvents signals. Data are reported as follows: chemical shift (δ), multiplicity (s=singlet, d=doublet, t=triplet, q=quartet, br. s=broad singlet, td=triplet of doublet, dd=doublet of doublets, ddd=doublet of doublets of doublets, m=multiplet), coupling constants (Hz), and number of protons.

Exact mass data ESI(+) were obtained on a Waters Q-Tof Ultima mass spectrometer directly connected with a Agilent 1100 micro-HPLC system as previously described (M. Colombo, F. Riccardi-Sirtori, V. Rizzo, *Rapid Commun. Mass Spectrom.* 2004, 18, 511-517).

In the examples below as well as throughout the application, the following abbreviations have the following meanings. If not defined, the terms have their generally accepted meanings.

| ABBREVIATIONS | |
|---|---|
| DCC | N,N'-dicyclohexylcarbodiimide |
| DBU | diazabicycloundecene |
| DCM | dichloromethane |
| DIPEA | N,N-diisopropyethylamine |
| DMAP | N,N-dimethylaminopyridine |
| DMF | N,N-dimethylformamide |
| DMSO | dimethyl sulfoxide |
| EDCl | N-ethyl-N',N'-diisopropyl carbodiimide hydrochloride |
| EDC | 1-ethyl-3-(3-dimethylaminopropyl)carbodiimide |
| Et$_2$O | diethyl ether |
| EtOAc | ethyl acetate |
| EtOH | ethanol |
| HCl | hydrochloric acid |
| HOBt | 1H-benzotriazol-1-ol |
| LiHMDS | lithium bia(trimethylsilyl)amide |
| MeOH | methanol |
| Na$_2$SO$_4$ | sodium sulfate |
| NaHCO$_3$ | sodium hydrogen carbonate |
| NaOH | sodium hydroxide |
| TEA | triethylamine |
| TFA | trifluoro acetic acid |
| THF | tetrahydrofurane |

Example 1

Step b, Step a

N-(6-{[(8S)-8-{chloromethyl}-4-hydroxy-1-methyl-7,8-dihydro-6H-thieno[3,2-e]indol-6-yl}carbonyl}-1H-indol-3-yl)-1H-indole-6-carboxamide [(II)] (compd. 1)

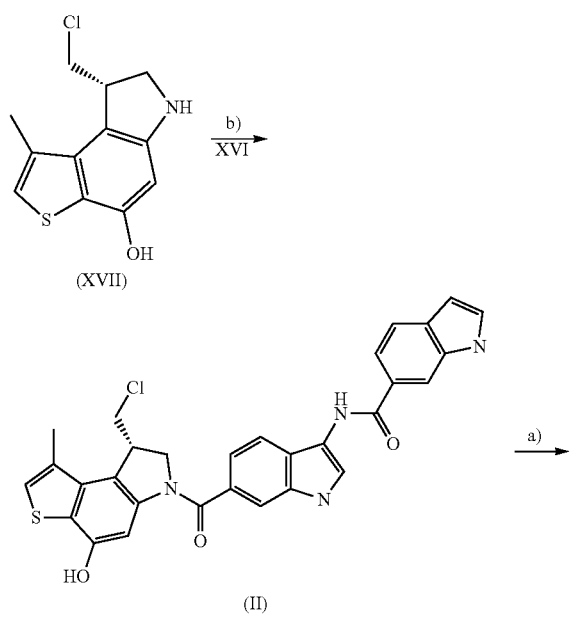

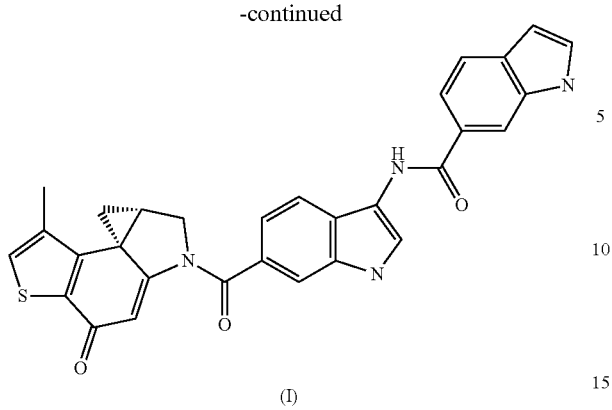

(I)

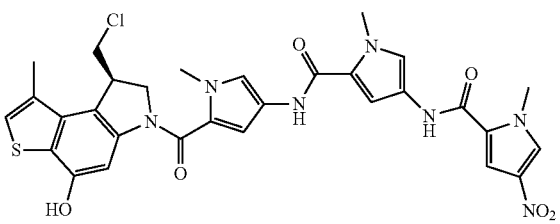 [SMILES: Cc1csc2c(O)cc3c(c12)[C@@H](CCl)CN3C(=O)c1cc(NC(=O)c2cc(NC(=O)c3cc([N+](=O)[O-])cn3C)cn2C)cn1C]

ESI MS: m/z 650 (MH+)

(2E)-1-[(8R)-8-(chloromethyl)-4-hydroxy-1-methyl-7,8-dihydro-6H-thieno[,2-e]indol-6-yl]-3-1H-pyrrolo[2,3-b]pyridin-3-yl)prop-2-en-1-one [(II)] (compd. 3)

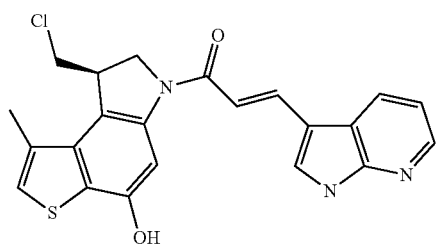 [SMILES: Cc1csc2c(O)cc3c(c12)[C@@H](CCl)CN3C(=O)/C=C/c1c[nH]c2ncccc12]

ESI MS: m/z 424 (MH+)

Step b

A solution of (8S)-8-(chloromethyl)-1-methyl-7,8-dihydro-6H-thieno[3,2-e]indol-4-ol (XVII) prepared as reported in the GB2344818 (14.2 mg, 0.0563 mmol) was dissolved in dry DMF (1.5 mL), and treated with EDCI (43 mg, 4 eq.) and 3-[(1H-indol-6-ylcarbonyl)amino]-1H-indole-6-carboxylic acid (XVI) (27 mg, 1.5 eq.) The mixture was stirred for 16 h at room temperature and then was quenched by adding saturated aqueous NaCl. Isolation of the product was performed by extraction with EtOAc (×4) and subsequent washing of the combined organic layers with aqueous 2M HCl (×3), saturated aqueous $Na_2CO_3$ (×3) and saturated aqueous NaCl (×3). Organic layer was dried ($Na_2SO_4$), concentrated under vacuum. The crude residue was purified by flash chromatography (hexane-acetone 6:4) to afford the title compound (18.7 mg, 60%).

ESI MS: m/z 555 (MH+)

(2E)-1-[(8S)-8-(chloromethyl)-4-hydroxy-1-methyl-7,8 dihydro-6H-thieno[3,2-e]indol-6-yl]-3-1H-pyrrolo[2,3-b]pyridin-3-yl)prop-2-en-1-one [(II)] (compd. 4)

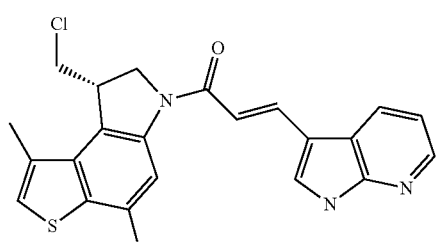

Analogously, by using the corresponding carboxylic acids, the following compounds have been prepared: N-(5-{[(8R)-8-(chloromethyl)-4-hydroxy-1-methyl-7,8-dihydro-6H-thieno[3,2-e]indol-6-yl]carbonyl}-1-methyl-1 H-pyrrol-3-yl)-1-methyl-4-{[(1-methyl-4-nitro-1H-pyrrol-2-yl)carbonyl]amino}1H-pyrrole-2-carboxamide [(II)](compd. 2)

ESI MS: m/z 424 (MH+)

N-(3-{(1E)-3-[(8S)-8-(chloromethyl)-4-hydroxy-1-methyl-7,8-dihydro-6H-thieno[3,2]indol-6-yl]-3-oxoprop-1-en-1-yl}1H-pyrrolo[2,3-b]pyridin-5-yl)-1H-indole-2-carboxamide [(II)] (compd. 13)

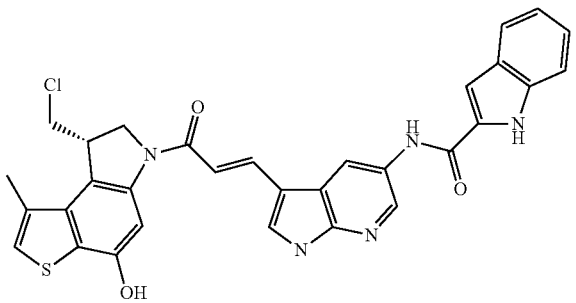 [SMILES: Cc1csc2c(O)cc3c(c12)[C@H](CCl)CN3C(=O)/C=C/c1c[nH]c2ncc(NC(=O)c3cc4ccccc4[nH]3)cc12]

ESI MS: m/z 582 (MH+)

N-(3-{(1E) 3-[(8R)-8-(chloromethyl)-4-hydroxy-1-methyl-7,8-dihydro-6H-thieno[3,2-e]indol-6-yl]-3-oxoprop-1-en-1-yl}1H-pyrrolo[2,3-b]pyridin-5-yl)-1H-indole-2-carboxamide [(II)] (compd. 14)

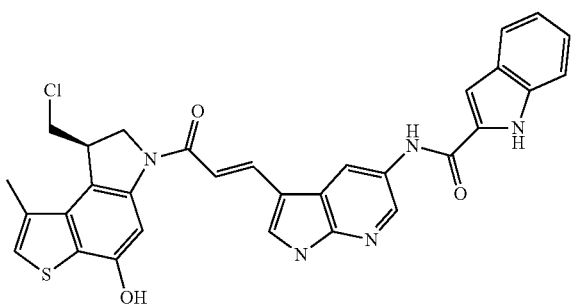 [SMILES: Cc1csc2c(O)cc3c(c12)[C@@H](CCl)CN3C(=O)/C=C/c1c[nH]c2ncc(NC(=O)c3cc4ccccc4[nH]3)cc12]

ESI MS: m/z 582 (MH+)

(2E)-1-[(8S)-8-(chloromethyl)-4-hydroxy-1-methyl-7,8-dihydro-6H-thieno[3,2-e]indol-6 yl]3-1H-indol-3-yl)prop-2-en-1-one [(II)] (compd. 43)

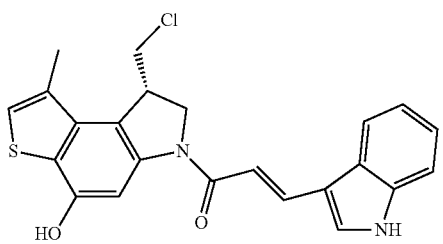 [SMILES: Cc1csc2c(O)cc3c(c12)[C@H](CCl)CN3C(=O)/C=C/c1c[nH]c2ccccc12]

ESI MS: m/z 423 (MH+)
$^1$H NMR (500 MHz, acetone-d6) δ ppm 2.60 (d, J=1.0 Hz, 3 H) 3.58 (m, 1 H) 3.88 (m, J=11.2, 1.9 Hz, 1 H) 4.2 (m, 1 H) 4.46 (t, J=9.5 Hz, 1 H) 4.63 (d, J=10.6 Hz, 1 H) 7.07 (d, J=15.4 Hz, 1 H) 7.24 (m, 1 H) 7.32 (m, 1 H) 7.53 (m, 1 H) 7.91 (m, 1 H) 8.02 (m, 2 H) 8.13 (br. s., 1 H) 9.26 (br. s., 1 H) 10.81 (br. s., 1 H)

N-(2-{[(8R)-8-(chloromethyl)-4-hydroxy-1-methyl-7,8-dihydro 6H-thieno[3,2-e]indol-6 yl]carbonyl}-1-methyl-1H-indo-5-yl)-1-methyl-1H-indole-2-carboxamide [(II)] (compd. 44)

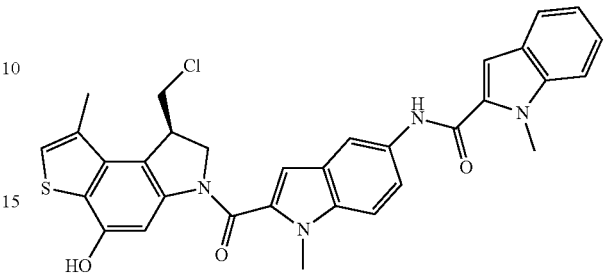

ESI MS: m/z 583 (MH+)

Step a

N-(6-{[(3bR,4aS)-3-methyl-8-oxo-4a,5-dihydro-4H-cyclopropa[c]thieno[3,2-e]indol-6(8H)-yl]carbonyl}-1H-indol-3-yl)-1H-indole-6-carboxamide [(I)] (compd. 5)

Compound 1 (25 mg, 0.045 mmol) was dissolved in DMF (2 mL), and treated with a solution of NaHCO$_3$ in water (1 mL, 15 mg NaHCO$_3$/mL). The reaction mixture was stirred for 2 h, EtOAc was added and the resulting organic layer was washed with brine (×4), dried (Na$_2$SO$_4$) and concentrated in vacuo. The crude residue was purified by flash chromatography (hexane-acetone 6:4) to afford compound 5 (19 mg, 82%).

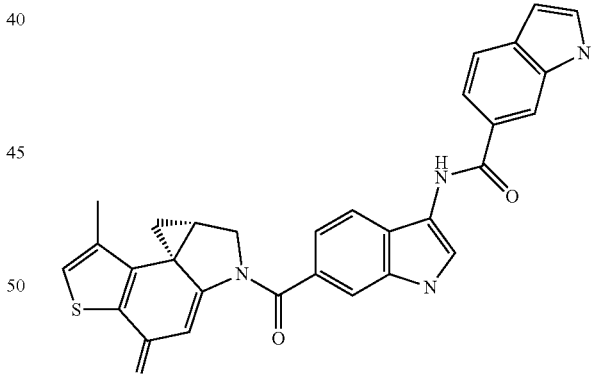

ESI MS: m/z 519 (MH+)
$^1$H NMR (500 MHz, acetone-d$_6$) δ ppm 1.75 (t, J=4.8 Hz, 1 H) 2.27 (s, 3 H) 2.32 (dd, J=7.6, 4.6 Hz, 1 H) 3.40 (dt, J=7.5, 4.9 Hz, 1 H) 4.13 (d, J=11.3 Hz, 1 H) 4.30 (dd, J=11.1, 4.7 Hz, 1 H) 5.78 (s, 1 H) 6.57 (br. s., 1 H) 7.32 (dd, J=8.4, 0.7 Hz, 1 H) 7.44 (s, 1 H) 7.52 (t, J=2.7 Hz, 1 H) 7.67 (d, J=8.2 Hz, 1 H) 7.79 (m, 2 H) 8.00 (d, J=8.2 Hz, 1 H) 8.22 (d, J=2.7 Hz, 2 H) 9.51 (s, 1 H) 10.45 (br. s, 1 H) 10.61 (br. s, 1 H)

Analogously, by using the corresponding carboxylic acids, the following compounds have been prepared:

1-methyl-N-(1-methyl-5-{[(3bS,4aR)-3-methyl-8-oxo-4a,5-dihydro-4H-cyclopropa[c]thieno[3,2-e]indol-6(8H)-yl]carbonyl}-1H-pyrrol-3-yl)-4-4{[(1-methyl-4-nitro-1H-pyrrol-2-yl)carbonyl]amino}-1H-pyrrole-2-carboxamide [(I)] (compd. 6)

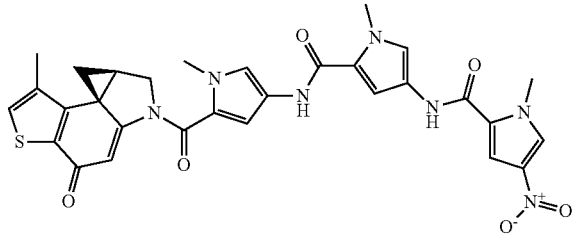 [SMILES: Cc1csc2c1[C@]13C[C@H]1CN(C(=O)c1cc(NC(=O)c4cc(NC(=O)c5cc([N+](=O)[O-])cn5C)cn4C)cn1C)C3=CC2=O]

ESI MS: m/z 614 (MH+)

$^1$H NMR (500 MHz, DMSO-$d_6$) δ ppm 1.52 (t, J=4.9 Hz, 1 H) 2.21 (s, 3 H) 2.28 (dd, J=7.6, 4.3 Hz, 1 H) 3.43 (dt, J=7.8, 5.2 Hz, 1 H) 3.76 (s, 3 H) 3.86 (s, 3 H) 3.96 (s, 3 H) 4.16 (d, J=10.7 Hz, 1 H) 4.29 (dd, J=10.6, 4.8 Hz, 1 H) 6.30 (s, 1 H) 6.77 (d, J=1.7 Hz, 1 H) 7.08 (d, J=1.8 Hz, 1 H) 7.25 (d, J=1.7 Hz, 1 H) 7.48 (d, J=1.7 Hz, 1 H) 7.58 (t, J=1.9 Hz, 2 H) 8.19 (d, J=1.8 Hz, 1 H) 10.00 (s, 1 H) 10.30 (s, 1 H)

(3bS,4aR)-3-methyl-6-[(2E)-3-(1H-pyrrolo[2,3-b]pyridin-3-yl)prop-2-enoyl]-4,4a,5,6-tetrahydro-8H-cyclopropa[c]thieno[3,2-e]indo-8-one [(I)] (compd. 7)

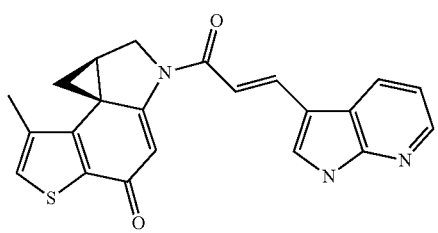 [SMILES: Cc1csc2c1[C@]13C[C@H]1CN(C(=O)/C=C/c1c[nH]c4ncccc14)C3=CC2=O]

ESI MS: m/z 388 (MH+)

$^1$H NMR (500 MHz, acetone-$d_6$) δ ppm 1.45 (t, J=4.8 Hz, 1 H) 2.19 (dd, J=7.6, 4.5 Hz, 1 H) 2.26 (d, J=0.7 Hz, 3 H) 3.44 (dt, J=7.7, 4.8 Hz, 1 H) 4.40 (dd, J=10.4, 4.8 Hz, 1 H) 4.51 (d, J=10.3 Hz, 1 H) 6.98 (d, J=15.4 Hz, 1 H) 7.08 (br. s., 1 H) 7.24 (dd, J=7.9, 4.7 Hz, 1 H) 7.44 (s, 1 H) 7.98 (d, J=15.4 Hz, 1 H) 8.09 (s, 1 H) 8.34 (dd, J=4.8, 1.5 Hz, 1 H) 8.41 (dd, J=7.8, 1.3 Hz, 1 H) 11.30 (s, 1 H)

(3bR,4aS)-3-methyl-6-[(2E)-3-(1H-pyrrolo[2,3-b]pyridin-3-yl)prop-2-enoyl]-4,4a,5,6-tetrahydro-8H-cyclopropa[c]thieno[3,2-e]indol-8-one [(I)] (compd. 8)

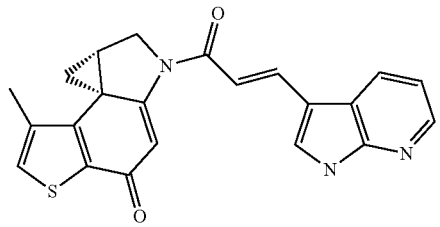 [SMILES: Cc1csc2c1[C@@]13C[C@@H]1CN(C(=O)/C=C/c1c[nH]c4ncccc14)C3=CC2=O]

ESI MS: m/z 388 (MH+)

$^1$H NMR (500 MHz, acetone-$d_6$) δ ppm 1.45 (t, J=4.9 Hz, 1 H) 2.16-2.21 (m, 1 H) 2.26 (s, 3 H) 3.44 (dt, J=7.7, 4.9 Hz, 1 H) 4.40 (dd, J=10.4, 5.1 Hz, 1 H) 4.51 (d, J=10.4 Hz, 1 H) 6.98 (d, J=15.4 Hz, 1 H) 7.08 (br. s., 1 H) 7.24 (dd, J=7.8, 4.5 Hz, 1 H) 7.44 (s, 1 H) 7.98 (d, J=15.4 Hz, 1 H) 8.09 (s, 1 H) 8.34 (dd, J=4.7, 1.1 Hz, 1 H) 8.41 (d, J=7.8 Hz, 1 H) 11.29 (br. s., 1 H)

N-(3-{(1E)-3-[(3bR,4aS)-3-methyl-8-oxo 4a,5-dihydro-4H-cyclopropa[c]thieno[3,2-e]indol-6(8H)-yl] 3-oxoprop-1-en-1-yl}-1H-pyrrolo[2,3-b]pyridin-5-yl)-1H-indole-2-carboxamide [(I)] (compd. 15)

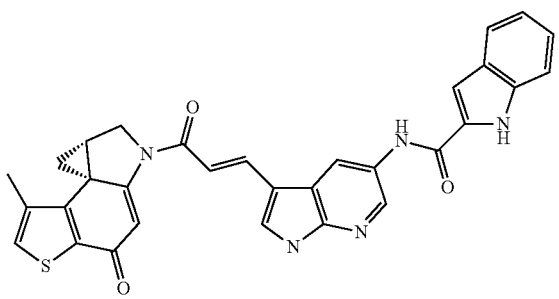 [SMILES: Cc1csc2c1[C@@]13C[C@@H]1CN(C(=O)/C=C/c1c[nH]c4ncc(NC(=O)c5cc6ccccc6[nH]5)cc14)C3=CC2=O]

ESI MS: m/z 546 (MH+)

N-(3-{(1E)-3-[(3bR,4aS)-3-methyl-8-oxo-4a,5-dihydro-4H-cyclopropa[c]thieno[3,2-e]indol-6(8H)-yl]-3-oxoprop-1-en-1-yl}-1H-pyrrolo[2,3-b]pyridin-5-yl)-1H-indole-2-carboxamide [(I)] (compd. 16)

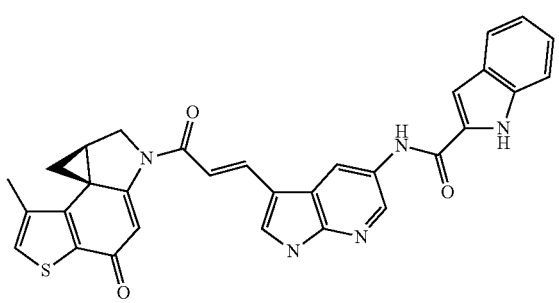 [SMILES: Cc1csc2c1[C@]13C[C@H]1CN(C(=O)/C=C/c1c[nH]c4ncc(NC(=O)c5cc6ccccc6[nH]5)cc14)C3=CC2=O]

ESI MS: m/z 546 (MH+)

¹H NMR (500 MHz, acetone-d6) δ ppm 1.58 (m, 1H) 2.24 (m, 1H) 2.27 (s, 3 H) 3.47 (dt, J=7.6, 4.9 Hz, 1 H) 4.39 (dd, J=10.2, 4.9 Hz, 1 H) 4.48 (m, 1 H) 6.96 (d, J=15.1 Hz, 1 H) 7.01 (s, 1 H) 7.12 (m, 2 H) 7.28 (m, 1 H) 7.40 (d, J=1.8 Hz, 1 H) 7.45 (s, 1 H) 7.61 (d, J=8.3 Hz, 1 H) 7.70 (d, J=8.1 Hz, 1 H) 7.98 (m, 1 H) 8.09 (d, J=2.8 Hz, 1 H) 8.76 (d, J=2.0 Hz, 1 H) 8.87 (d, J=2.0 Hz, 1 H) 9.76 (br. s., 1 H) 10.97 (br. s., 1 H) 11.32 (br. s., 1 H)

1-methyl-N-(1-methyl-2-{[(3bS,4aR)-3-methy-8-oxo-4a,5-dihydro-4H-cyclopropa[c]thieno[3,2-e]indol-6(8H)-yl]carbonyl}-1H-indol-5-yl)-1H-indole-2-carboxamide [(I)] (compd. 45)

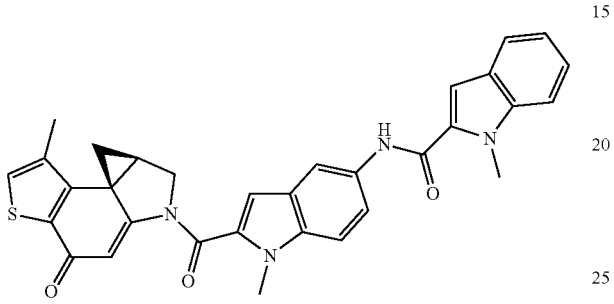

ESI MS: m/z 547 (MH+)

¹H NMR (500 MHz, acetone-d6) δ ppm 1.65 (t, J=4.9 Hz, 1 H) 2.27 (d, J=12.4 Hz, 1 H) 2.27 (d, J=0.7 Hz, 3 H) 3.43 (dt, J=7.6, 4.89 Hz, 1 H) 3.93 (s, 3 H) 4.12 (s, 3 H) 4.38 (d, J=11.1 Hz, 1 H) 4.51 (dd, J=10.8, 4.8 Hz, 1 H) 6.52 (s, 1 H) 7.08 (s, 1 H) 7.13 (m, 1 H) 7.26 (s, 1 H) 7.32 (td, J=7.7, 1.0 Hz, 1 H) 7.47 (d, J=1.0 Hz, 1 H) 7.54 (m, 2 H) 7.66 (d, J=7.8 Hz, 1 H) 7.71 (dd, J=9.1, 2.0 Hz, 1 H) 8.29 (d, J=2.0 Hz, 1 H) 9.54 (s, 1 H)

Example 2 tert-butyl {2-[(2-(2-{[(8S)-8-(chloromethyl)-4-hydroxy-1 methyl-7,8-dihydro-6H-thieno[32-e]indol-6-yl]carbonyl}-1 H-indol-5-yl)carbamoyl]-1H-indol-5-yl}carbamate [(II)] (compd. 18)

Step b, Deprotection, Step a

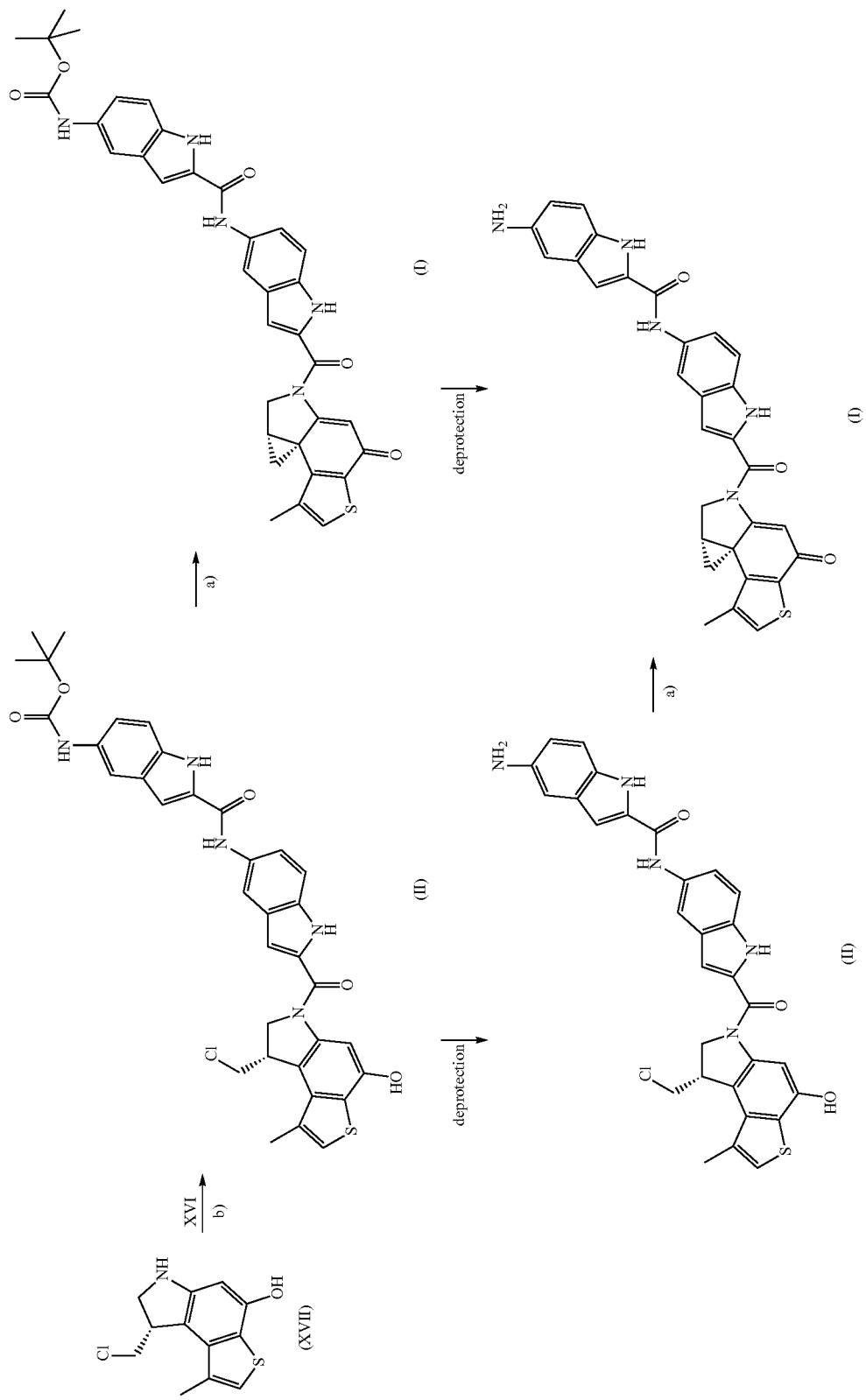

Step b

A solution of (8S)-8-(chloromethyl)-1-methyl-7,8-dihydro-6H-thieno[3,2-e]indol-4-ol ((XVII), 11.4 mg, 0.045 mmol), prepared as reported in GB2344818, was dissolved in dry DMF (1 mL), and treated with EDCI (35 mg, 4 eq.) and 5-[({5-[(tert-butoxycarbonyl)amino]-1H-indol-2-yl}carbonyl)amino]-1H-indole-2-carboxylic acid (XVI) (29 mg, 1.5 eq.) The mixture was stirred for 16 h at room temperature and then was quenched by adding saturated aqueous NaCl. Isolation of the product was performed by extraction with EtOAc (×4) and subsequent washing of the combined organic layers with aqueous 2M HCl (×3), saturated aqueous Na$_2$CO$_3$ (×3) and saturated aqueous NaCl (×3). Organic layer was dried (Na$_2$SO$_4$), concentrated under vacuum to give the title compd. 18, that is then purified by flash chromatography hexane-acetone 1:1).

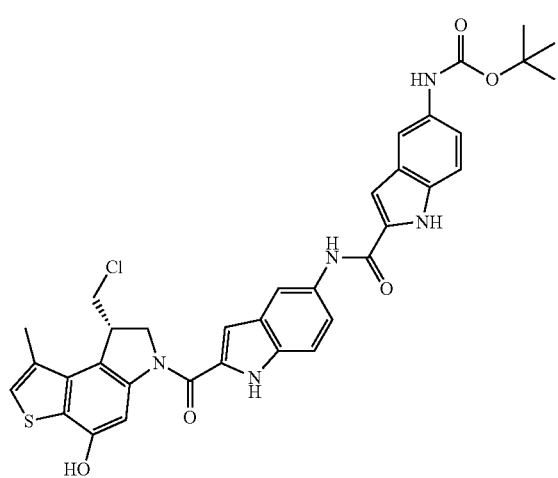 [SMILES: Cc1csc2c(O)cc3c(c12)[C@H](CCl)CN3C(=O)c1cc2cc(NC(=O)c3cc4cc(NC(=O)OC(C)(C)C)ccc4[nH]3)ccc2[nH]1]

ESI MS: m/z 670 (MH$^+$)
$^1$H NMR (500 MHz, acetone-d$_6$) δ ppm 1.50 (s, 9 H) 1.79 (dt, J=6.4, 3.3 Hz, 1 H) 2.61 (s, 2 H) 3.53-3.66 (m, 1 H) 3.89 (dd, J=11.4, 2.8 Hz, 1 H) 4.25 (m, 1 H) 4.73 (m, 1 H) 4.84 (d, J=10.6 Hz, 1 H) 7.21 (s, 1 H) 7.26 (s, 1 H) 7.34 (m, 2 H) 7.49 (d, J=8.8 Hz, 1 H) 7.56 (m, 1 H) 7.61 (m, 1 H) 7.96 (br. s., 2 H) 8.21 (br. s., 1 H) 8.34 (s, 1 H) 9.28 (s, 1 H) 9.52 (s, 1 H) 10.73 (br. s., 1 H) 10.80 (br. s., 1 H).

By deprotection, the following compound has been obtained:

5-amino-N-(2-{[(8S)-8-(chloromethyl)-4-hydroxy-1-methyl-5a,7,8,8a-tetrahydro-6H-thieno[3,2-e]indo-6-yl]carbonyl}-1H-indol-5-yl)-1H-indole-2-carboxamide [(II)] (compd. 19)

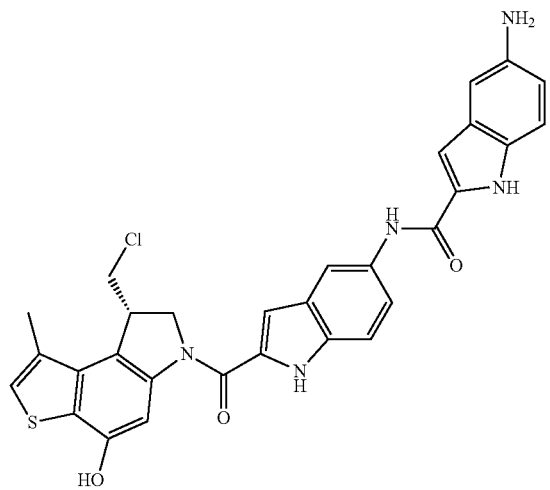 [SMILES: Cc1csc2c(O)cc3c(c12)[C@H](CCl)CN3C(=O)c1cc2cc(NC(=O)c3cc4cc(N)ccc4[nH]3)ccc2[nH]1]

A solution of compd. 18 (18 mg, 0.0268 mmol) in 3.5 M HCl-EtOAc (5 mL) was stirred for 30 minutes before removing the solvent under a steady stream of nitrogen and affording hydrochloride derivative of compd. 2 (15 mg, 89%).
ESI MS: m/z 570 (MH$^+$)
Step a tert-butyl {2-[(2-{[(3bR,4aS)-3-methyl-8-oxo-4a,5-dihydro-4H-cyclopropa[c]thieno[3,2-e]indol-6(8H)-yl]carbonyl}-1H-indol-5-yl)carbamoyl]-1H-indol-5-yl}carbamate [(I)] (compd. 20)

Compd. 18 (30 mg, 0.045 mmol) was dissolved in DMF (1 mL), and treated with aqueous NaHCO$_3$ (0.5 mL, 15 mg NaHCO$_3$/mL). The reaction mixture was stirred for 2 h, EtOAc was added and the resulting organic layer was washed with brine (×4), dried (Na$_2$SO$_4$) and concentrated in vacuo. The crude residue was purified by flash chromatography (hexane-acetone 6:4) to afford the final compd. 20 (9 mg, 31%).
ESI MS: m/z 634 (MH$^+$)
$^1$H NMR (500 MHz, acetone-d$_6$) δ ppm 1.41 (s, 9 H) 1.56 (t, J=4.8 Hz, 1 H) 2.22 (m, 1 H) 2.29 (d, J=0.9 Hz, 3 H) 3.52 (m, 1 H) 4.69 (m, 2 H) 7.06 (s, 1 H) 7.26 (d, J=1.5 Hz, 1 H) 7.28 (d, J=1.8 Hz, 1 H) 7.36 (dd, J=8.8, 1.8 Hz, 1 H) 7.48

(m, 1 H) 7.49 (d, J=8.8 Hz, 1 H) 7.58 (m, 1 H) 7.63 (m, 1 H) 7.96 (br. s., 1 H) 8.26 (br. s., 1 H) 8.35 (s, 1 H) 9.55 (s, 1 H) 10.77 (br. s., 1 H) 10.95 (br. s., 1 H)

By deprotection the following compound has been prepared:

5-amino-N-(2-{[(3bR,4aS)-3-methyl-8-oxo-4a,5-dihydro-4H-cyclopropa[c]thieno[3,2-e]indol-6(8H)-yl]carbonyl}-1H-indol-5-yl)-1H-indole-2-carboxamide [(I)] (compd. 21)

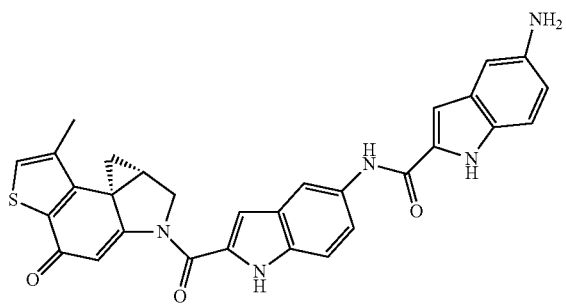 [SMILES: Cc1csc2c1[C@@]13C[C@@H]1CN(C(=O)c1cc4cc(NC(=O)c5cc6cc(N)ccc6[nH]5)ccc4[nH]1)C3=CC2=O]

ESI MS: m/z 534 (MH+)

By analogue procedure and using the suitable starting material the following compounds have been prepared:

tert-butyl {2-[(2-{[(3bS,4aR)-3-methyl-8-oxo-4a,5-dihydro-4H-cyclopropa[c]thieno[3,2-e]indol-6(8H)-yl]carbonyl}-1H-indol-5-yl)carbamoyl]-1H-indol-5-yl}carbamate [(I)] (compd. 25)

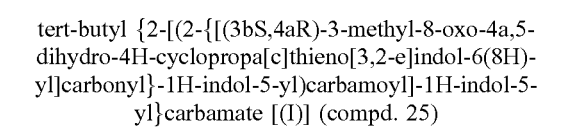

ESI MS: m/z 634 (MH+)

5-amino-N-(2-{[(3bS,4aR)-3-methy oxo-4a,5-dihydro-4H-cyclopropa[c]thieno[3,2-e]indol-6(8H)-yl]carbonyl}-1H-indol-5-yl)-1H-indole-2-carboxamide [(I)] (compd. 26)

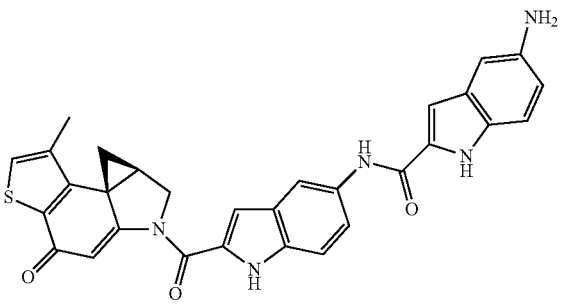 [SMILES: Cc1csc2c1[C@]13C[C@H]1CN(C(=O)c1cc4cc(NC(=O)c5cc6cc(N)ccc6[nH]5)ccc4[nH]1)C3=CC2=O]

ESI MS: m/z 534 (MH+)

N-(2-{[(3bR,4aS)-3-methyl-8-oxo-4a,5-dihydro-4H-cyclopropa[c]thieno[3,2-e]indol-6(8H)-yl]carbonyl}-1H-indol-5-yl)-5-nitro-1H-indole-2-carboxamide [(I)] (compd. 29)

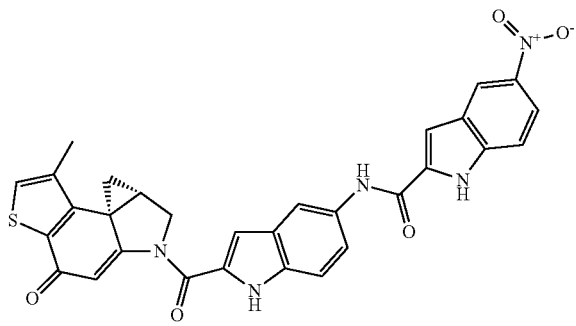 [SMILES: Cc1csc2c1[C@@]13C[C@@H]1CN(C(=O)c1cc4cc(NC(=O)c5cc6cc([N+](=O)[O-])ccc6[nH]5)ccc4[nH]1)C3=CC2=O]

ESI MS: m/z 564 (MH+)

N-(2-{[(3bS,4aR)-3-methyl-8-oxo-4a,5-dihydro-4H-cyclopropa[c]thieno[3,2-e]indol-6(8H)-yl]carbonyl}-1H-indol-5-yl)-5-nitro-1H-indole-2-carboxamide [(I)] (compd. 30)

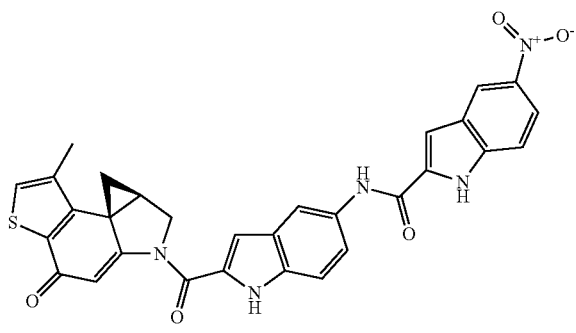 [SMILES: Cc1csc2c1[C@]13C[C@H]1CN(C(=O)c1cc4cc(NC(=O)c5cc6cc([N+](=O)[O-])ccc6[nH]5)ccc4[nH]1)C3=CC2=O]

ESI MS: m/z 564 (MH+)

Example 3

Step b, Deprotection, Step a

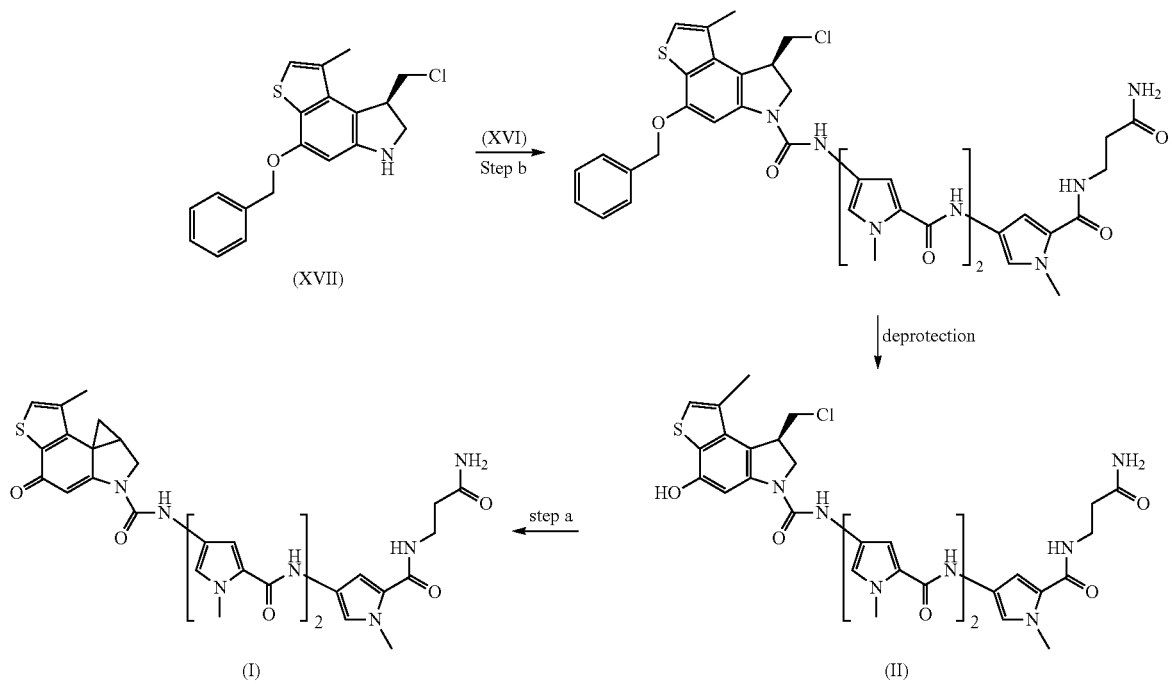

Step b

The Intermediate (8R)—N-(5-{[5-({5-[(3-amino-3-oxopropyl)carbamoyl]-1-methyl-1H-pyrrol-3-yl}carbamoyl)-1-methyl-1H-pyrrol-3-yl]carbamoyl}-1-methyl-1H-pyrrol-3-yl)-4-(benzyloxy)-8-(chloromethyl)-1-methyl-7,8-dihydro-6H-thieno[3,2-e]indole-carboxamide A solution of 4-amino-N-[5-({5-[(3-amino-3-oxopropyl)carbamoyl]-1-methyl-1H-pyrrol-3-yl}carbamoyl)-1-methyl-1H-pyrrol-3-yl]-1-methyl-1H-pyrrole-2-carboxamide, prepared as reported in *J.Med. Chem.* 2004, 47, 2611-2623, (155 mg, 0.341 mmol), triethylamine (0.048 mL, 0.341 mmol) and CDI (300 mg, 1.71 mmol) in dry DMF (5 mL) was stirred at room temperature for 1 h. After evaporation of the solvent, the residue was treated with THF and stirred overnight. The precipitate (comp XVI) was filtered and dried under vacuum at 50° C. and treated with (8R)-4-(benzyloxy)-8-(chloromethyl)-1-methyl-7,8-dihydro-6H-thieno[3,2-e]indole (comp (XVII) (15.5 mg, 0.045 mmol, prepared as reported in the GB2344818) in dry DMF (2 mL) in the presence of NaHCO₃ (4 mg, 0.047 mmol) and were stirred under nitrogen atmosphere at room temperature for 16 h. After evaporation of the solvent the residue was purified by flash chromatography (DCM-MeOH 95:5) to afford the intermediate (30 mg, 80%).

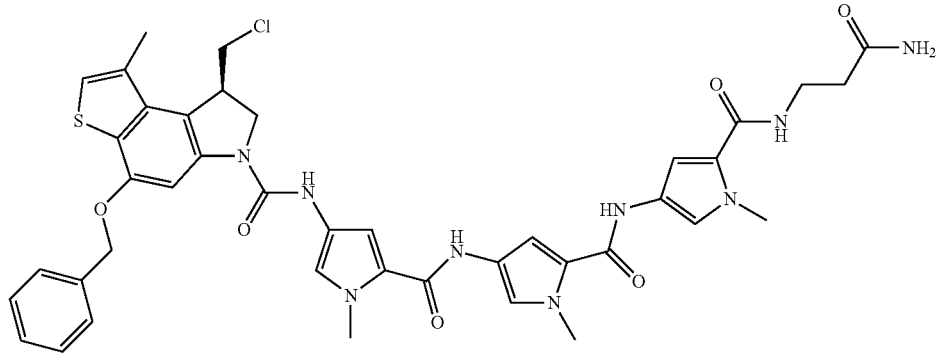 [SMILES: Cc1csc2c(OCc3ccccc3)cc3c(c12)[C@@H](CCl)CN3C(=O)Nc1cc(C(=O)Nc2cc(C(=O)Nc3cc(C(=O)NCCC(N)=O)n(C)c3)n(C)c2)n(C)c1]

ESI MS: m/z 824 (MH+)

$^1$H NMR (500 MHz, DMSO-d$_6$) δ ppm 2.31 (t, J=7.2 Hz, 2 H) 2.53 (s, 3 H) 3.53 (t, J=10.4 Hz, 1 H) 3.80 (s, 3 H) 3.85 (s, 3 H) 3.87 (s, 3 H) 4.12 (m, 1 H) 4.18 (m, 1 H) 4.32 (d, J=10.4 Hz, 1 H) 5.27 (s, 2 H) 6.83 (d, J=1.7 Hz, 1 H) 6.84 (m, 1 H) 7.05 (m, 2 H) 7.13 (d, J=1.5 Hz, 1 H) 7.20 (d, J=−1.5 Hz, 1 H) 7.25 (d, J=1.5 Hz, 1 H) 7.36 (m, 2 H) 7.41 (s, 1 H) 7.43 (m, 2 H) 7.50 (d, J=7.3 Hz, 2 H) 7.99 (m, 2 H) 8.77 (s, 1 H) 9.91 (s, 1 H) 9.93 (s, 1 H)

Analogously, by using the corresponding acyl derivative, the following compounds have been prepared:

(8S)—N-(5-{[5-({5-[(3-amino-3-oxopropyl)carbamoyl]-1-methyl-1H-pyrrol-3-yl)carbamoyl}-1-methyl-1H-pyrrol-3-yl]carbamoyl}-1-methyl-1H-pyrrol-yl)-4-(benzyloxy)-8-(chloromethyl)-1-methyl-7,8-dihydro-6H-thieno[3,2-e]indole-6-carboxamide

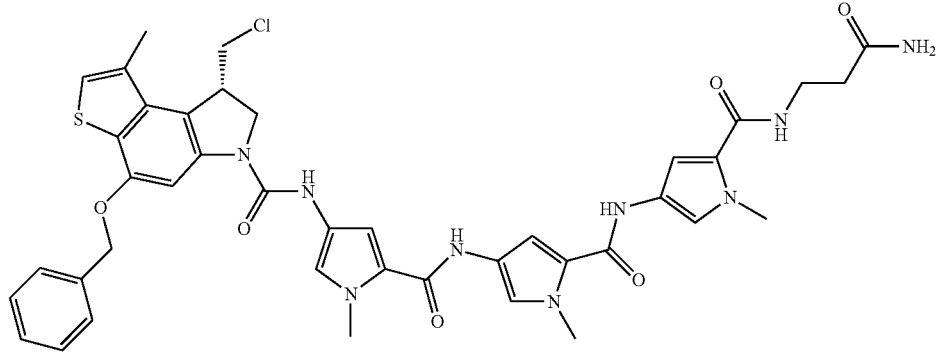 [SMILES: Cc1csc2c(OCc3ccccc3)cc3c(c12)[C@H](CCl)CN3C(=O)Nc1cc(C(=O)Nc2cc(C(=O)Nc3cc(C(=O)NCCC(N)=O)n(C)c3)n(C)c2)n(C)c1]

ESI MS: m/z 824 (MH+)

N-(2-{[(8S)-4-(benzyloxy)-8-(chloromethyl)-1-methy-7,8-dihydro-6H-thieno[3,2-e]indol-6-yl]carbonyl}-1H-indol-5-yl)-5-[2-(pyrrolidin-1-yl)ethoxy]-1H-indole-2-carboxamide

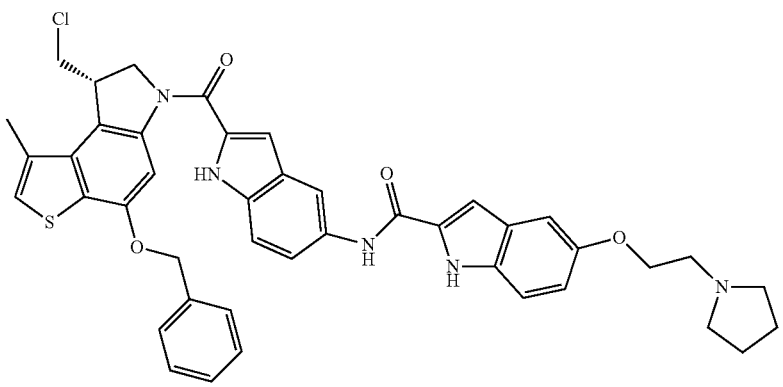 [SMILES: Cc1csc2c(OCc3ccccc3)cc3c(c12)[C@H](CCl)CN3C(=O)c1cc2cc(NC(=O)c3cc4cc(OCCN5CCCC5)ccc4[nH]3)ccc2[nH]1]

ESI MS: m/z 758 (MH+)
$^1$H NMR (500 MHz, acetone-d$_6$) δ ppm 1.74 (m, 4 H) 2.59 (m, 4 H) 2.63 (d, J=1.0 Hz, 3 H) 2.86 (m, 2H) 3.65 (dd, J=11.4, 9.6 Hz, 1 H) 3.93 (dd, J=11.4, 2.4 Hz, 1 H) 4.12 (t, J=6.1 Hz, 2 H) 4.29 (m, 1 H) 4.77 (m, 1 H) 4.87 (m, 1 H) 5.36 (m, 2 H) 6.94 (dd, J=8.8, 2.3 Hz, 1 H) 7.15 (d, J=2.3 Hz, 1 H) 7.25 (m, 2 H) 7.35 (m, 1 H) 7.38 (d, J=1.0 Hz, 1 H) 7.43 (m, 2 H) 7.49 (d, J=9.1 Hz, 1 H) 7.58 (m, 3 H) 7.63 (m, 1 H) 8.18 (br. s., 1 H) 8.37 (d, J=1.3 Hz, 1 H) 9.52 (s, 1 H) 10.77 (br. s., 1 H) 10.87 (br. s., 1 H)

[(8S)-4-(benzyloxy)-8-(chloromethyl)-1-methyl-7,8-dihydro-6H-thieno[3,2-e]indol-6-yl]{5-[2-(pyrrolidin-1-yl)ethoxy]-1H-indol-2-yl}methanone hydrochloride

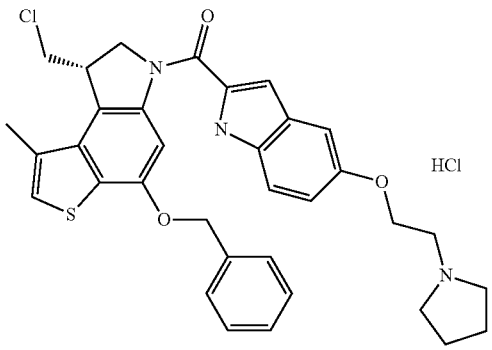 [SMILES: Cc1csc2c(OCc3ccccc3)cc3c(c12)[C@H](CCl)CN3C(=O)c1cc2cc(OCCN3CCCC3)ccc2[nH]1 ; Cl]

ESI MS: m/z 600 (MH+)
$^1$H NMR (500 MHz, acetone-$d_6$) δ ppm 2.06 (m, 4H) 2.62 (d, J=1.0 Hz, 3 H) 3.02-3.32 (m, 2 H) 3.56 (br. s., 2 H) 3.63 (dd, J=11.4, 9.6 Hz, 1 H) 3.91 (dd, J=11.4, 2.4 Hz, 1 H) 4.27 (m, 1 H) 4.57 (br. s., 2 H) 4.73 (dd, J=10.2, 8.2 Hz, 1 H) 4.84 (m, 1 H) 5.35 (m, 2 H) 7.05 (dd, J=8.8, 2.3 Hz, 1 H) 7.16 (d, J=1.7 Hz, 1 H) 7.31 (d, J=1.8 Hz, 1 H) 7.35 (m, 1 H) 7.38 (d, J=1.0 Hz, 1 H) 7.43 (m, 2 H) 7.52 (d, J=9.1 Hz, 1 H) 7.57 (d, J=7.6 Hz, 2 H) 8.16 (br. s., 1 H) 10.80 (br. s., 1 H) 13.38 (br. s., 1 H)

Deprotection (8R)—N-(5-{[5-({5-[(3-amino-3-oxopropyl)carbamoyl]-1-methyl-1H-pyrrol-3-yl}carbamoyl)-1-methyl-1H-pyrrol-3-yl]carbamoyl}-1-methyl-1H-pyrrol-3-yl)-8-(chloromethyl)-4-hydroxy-1-methyl-7,8-dihydro-6H-thieno[3,2-e]indole-6-carboxamide [(II)] (compd. 10)

A solution of the intermediate (15 mg, 0.0182 mmol), 25% aq. HCO$_2$NH$_4$ (0.15 mL) and 10% Pd—C (15 mg) in THF (3 mL) was stirred for 3 h under nitrogen atmosphere. The reaction mixture was filtered through Celite and concentrated to yield after chromatographic purification (DCM-MeOH 10:1) compound 10 (6.7 mg, 50%).

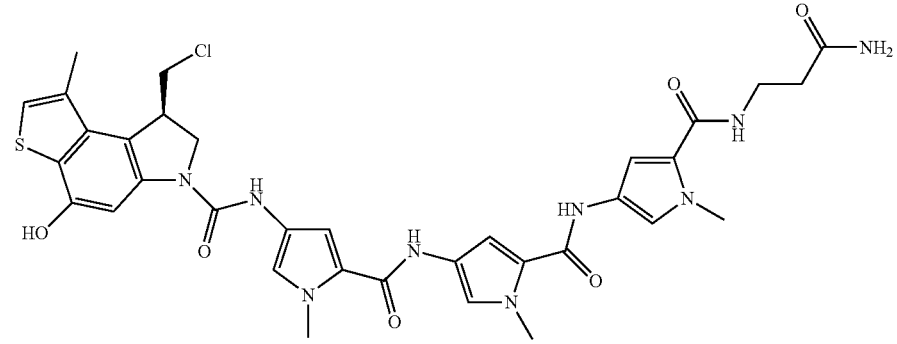 [SMILES: Cc1csc2c(O)cc3c(c12)[C@@H](CCl)CN3C(=O)Nc1cc(C(=O)Nc2cc(C(=O)Nc3cc(C(=O)NCCC(N)=O)n(C)c3)n(C)c2)n(C)c1]

ESI MS: m/z 734 (MH+)

Analogously the following compounds have been prepared:

(8S)—N-(5-{[5-{5-[(3-amino-3-oxopropyl)carbamoyl]-1-methyl-1H-pyrrol-3-yl}carbamoyl)-1-methyl-1H-pyrrol-3-yl]carbamoyl}-1-methyl-1H-pyrrol-3-yl)-8-(chloromethyl)-4-hydroxy-1-methyl-7,8-dihydro-6H-thieno[3,2-e]indole-6-carboxamide [(II)] (compd. 11)

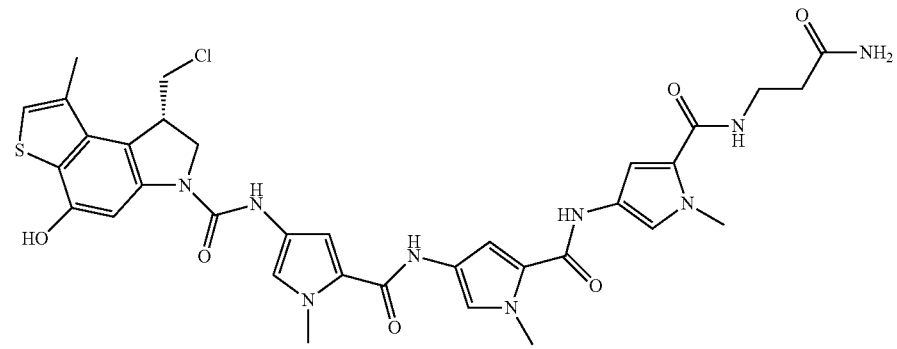 [SMILES: Cc1csc2c(O)cc3c(c12)[C@H](CCl)CN3C(=O)Nc1cc(C(=O)Nc2cc(C(=O)Nc3cc(C(=O)NCCC(N)=O)n(C)c3)n(C)c2)n(C)c1]

ESI MS: m/z 734 (MH+)

N-(2-{[(8S)-8-(chloromethyl)-4-hydroxy-1-methyl-7,8-dihydro-6H-thieno[3,2-e]indol-6-yl]carbonyl}-1H-indol-5-yl)-5-[2-(pyrrolidin-1-yl)ethoxy]-1H-indole-2-carboxamide [(II)] (compd. 17)

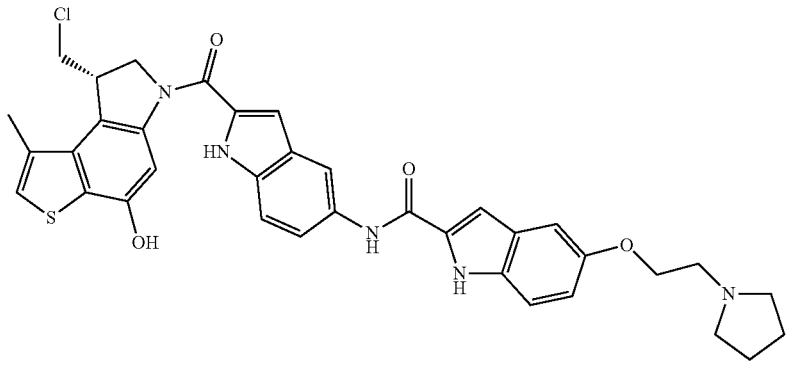 [SMILES: Cc1csc2c(O)cc3c(c12)[C@H](CCl)CN3C(=O)c1cc2cc(NC(=O)c3cc4cc(OCCN5CCCC5)ccc4[nH]3)ccc2[nH]1]

ESI MS: m/z 668 (MH+)

$^1$H NMR (500 MHz, acetone-d$_6$) δ ppm 2.19-2.25 (m, 4 H) 2.60 (s, 3 H) 3.39 (br. s., 2 H) 3.81 (m, 2 H) 3.88 (dd, J=11.1, 2.5 Hz, 1 H) 3.91-3.96 (br. s, 2 H) 4.24 (m, 1 H) 4.51 (m, 1 H) 4.72 (dd, J=10.8, 7.8 Hz, 1 H) 4.80-4.82 (d, J=10.8, 1 H) 7.01 (dd, J=8.9, 2.4 Hz, 1 H) 7.22 (s, 1 H) 7.26 (d, J=2.3 Hz, 1 H) 7.28 (s, 1 H) 7.33 (s, 1 H) 7.49 (d, J=8.9 Hz, 1 H) 7.55 (m, 1 H) 7.60 (m, 1 H) 7.90 (br. s., 1 H) 8.29 (d, J=1.8 Hz, 1 H)

[(8S)-8-(chloromethyl)-4-hydroxy-1-methyl-7,8-dihydro-6H-thieno[3,2-e]indol-6-yl]{5-[2-(pyrrolidin-1-yl)ethoxy]-1H-indol-2-yl}methanone hydrochloride [(II)] (compd. 37)

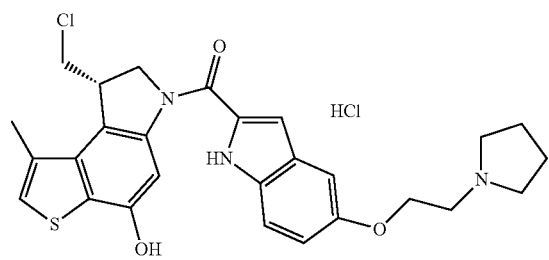 [SMILES: Cc1csc2c(O)cc3c(c12)[C@H](CCl)CN3C(=O)c1cc2cc(OCCN3CCCC3)ccc2[nH]1 ; Cl]

ESI MS: m/z 510 (MH+)

$^1$H NMR (500 MHz, acetone-d$_6$) δ ppm 2.10-2.29 (m, 4 H) 2.58 (d, J=1.3 Hz, 3 H) 3.33 (m, 2 H) 3.54 (dd, J=11.4, 10.1 Hz, 1 H) 3.80 (m, 2 H) 3.89 (m, 3 H) 4.20 (m, 1 H) 4.51 (m, 2 H) 4.68 (dd, J=10.2, 8.2 Hz, 1 H) 4.77 (m, 1 H) 7.04 (dd, J=8.9, 2.4 Hz, 1 H) 7.12 (s, 1 H) 7.29 (d, J=2.3 Hz, 1 H) 7.31 (d, J=0.5 Hz, 1 H) 7.49 (d, J=8.9 Hz, 1 H) 7.87 (br. s., 1 H)

[(8R)-8-(chloromethyl)-4-hydroxy-1-methyl-7,8-dihydro-6H-thieno[3,2-e]indol-6-yl]{5-[2-(pyrrolidin-1-yl)ethoxy]-1H-indol-2-yl})methanone hydrochloride [(II)] (compd. 38)

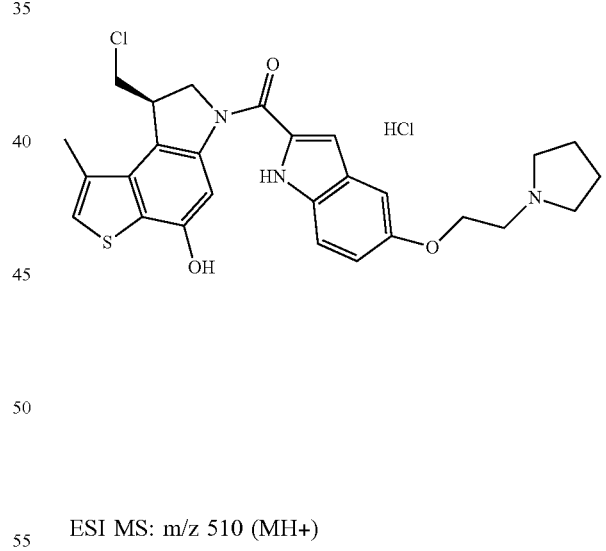

ESI MS: m/z 510 (MH+)

Step a

A solution of compound 10 (5 mg, 0.0068 mmol), in DMF (5 mL), was treated with a solution of NaHCO$_3$ in water (3 mL, 15 mg NaHCO$_3$/mL). The reaction mixture was stirred for 4 h, EtOAc was added and the resulting organic layer was washed with brine (×4), dried (Na$_2$SO$_4$) and concentrated in vacuo. The crude residue was purified by flash chromatography (DCM-MeOH 10:1) to afford the compound 9 (3.9 mg, 82%).

(3bS,4aR)-N-(5-{[5-({5-[(3-amino-3-oxopropyl)carbamoyl]-1-methyl-1H-pyrrol-3-yl}carbamoyl)-1-methyl-1H-pyrrol-3-yl]carbamoyl}-1-methyl-1H-pyrrol-3-yl)-3-methyl-8-oxo-4a,5-dihydro-4H-cyclopropa[c]thieno[3,2-e]indole-6(8H)-carboxamide [(I)] (compd. 9)

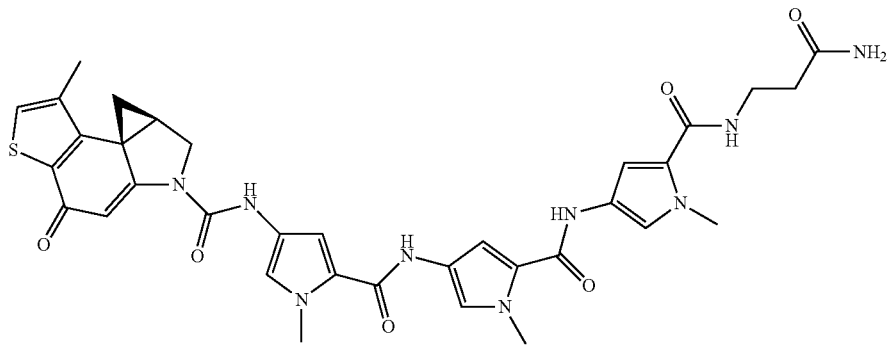 [SMILES: Cc1csc2c1[C@]13C[C@H]1CN(C(=O)Nc1cc(C(=O)Nc4cc(C(=O)Nc5cc(C(=O)NCCC(N)=O)n(C)c5)n(C)c4)n(C)c1)C3=CC2=O]

ESI MS: m/z 698 (MH+)
$^1$H NMR (500 MHz, dichloromethane-$d_2$) δ ppm 1.37 (m, 1H) 2.12 (dd, J=7.6, 4.6 Hz, 1 H) 2.18 (d, J=0.9 Hz, 3 H) 2.47 (t, J=6.6 Hz, 2 H) 3.26 (dt, J=7.6, 5.0 Hz, 1 H) 3.53 (1 , J=6.6 Hz, 2 H) 3.85 (s, 3 H) 3.88 (s, 6 H) 4.05 (d, J=10.4 Hz, 1 H) 4.14 (m, 1H) 6.64 (d, J=2.1 Hz, 1 H) 6.73 (s, 1 H) 6.82 (m, 2 H) 6.99 (d, J=1.8 Hz, 1 H) 7.17 (d, J=1.8 Hz, 1 H) 7.20 (d, J=1.8 Hz, 1 H) 7.29 (d, J=0.9 Hz, 1 H)

Analogously the following compounds have been prepared:

(3bR,4aS)—N-(5-{5-({5-[(3-amino-3-oxopropyl)carbamoyl-1-methyl-H-pyrrol-3-yl}carbamoyl)-1-methyl-1H-pyrrol-3-yl]carbamoyl}-1-methyl-1H-pyrrol-3-yl)-3-methyl-8-oxo-4a,5-dihydro-4H-cyclopropa[c]thieno[3,2-e]indole-6(8H)carboxamide [(I)] (compd. 12)

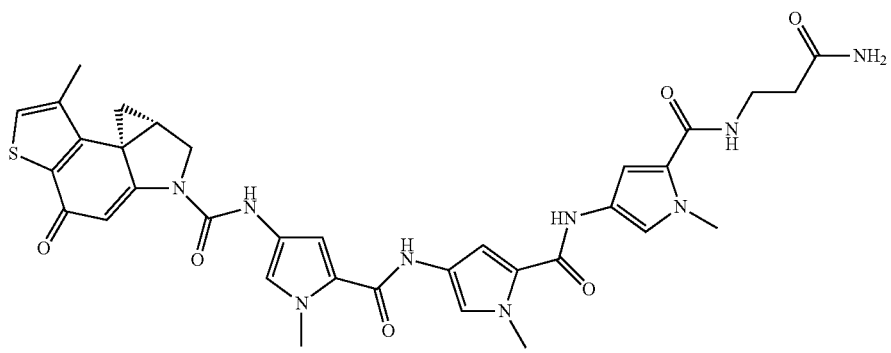 [SMILES: Cc1csc2c1[C@@]13C[C@@H]1CN(C(=O)Nc1cc(C(=O)Nc4cc(C(=O)Nc5cc(C(=O)NCCC(N)=O)n(C)c5)n(C)c4)n(C)c1)C3=CC2=O]

ESI MS: m/z 698 (MH+)

Example 4
Step c, Deprotection
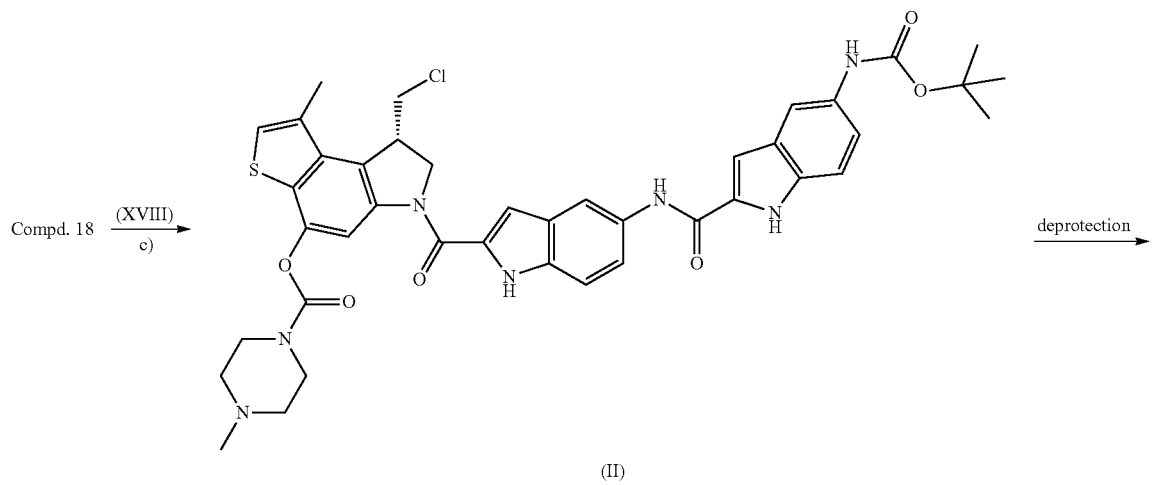
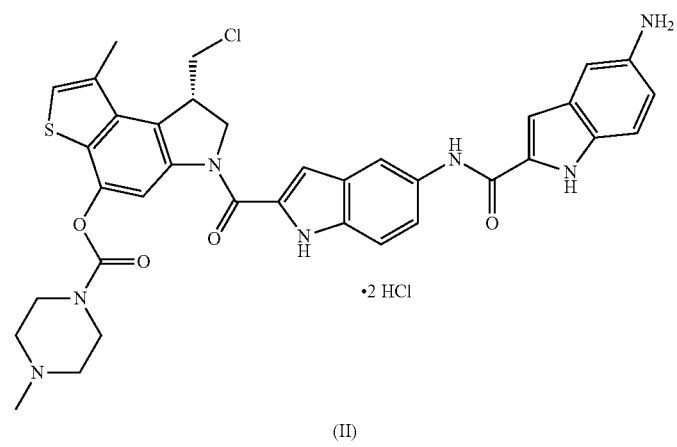

Step c (8S)-6-({5-[({5-[(tert-butoxycarbonyl)amino]-1H-indol-2-yl}carbonyl)amino]-1H-indol-2-yl}carbonyl)-8-(chloromethyl)-1-methyl-7,8-dihydro-6H-thieno[3,2-e]indol-4-yl 4-methylpiperazine-1-carboxylate [(II)](compd. 22)

To a solution of tert-butyl {2[(2-[(8S)-8-(chloromethyl)-4-hydroxy-1-methyl-7,8-dihydro-6H-thieno[3,2-e]indol-6-yl]carbonyl}-1H-indol-5-yl)carbamoyl]-1H-indol-5-yl)carbamate, (compd. 18) (42 mg, 0.064 mmol) in dry DCM (6 mL) 4-methylpiperazine-1-carbonyl chloride hydrochloride (XIII) (39 mg, 0.193 mmol) and N,N-dimethylaminopyridine (27 mg, 0.212 mmol) were added. The reaction mixture was stirred at room temperature under nitrogen atmosphere for 16 h. The solvent was evaporated and the residue was dissolved in EtOAc, the resulting organic layer was washed with brine (×3), dried (Na$_2$SO$_4$) and concentrated in vacuo. The crude residue was purified by flash chromatography (DCM-MeOH 95:5) to afford the compd. 22 (30 mg, 59%).

ESI MS: m/z 796 (MH$^+$)

$^1$H NMR (500 MHz, acetone-d$_6$) δ ppm 2.22 (s, 3 H) 2.65 (d, J=0.9 Hz, 3 H) 2.39-2.91 (m, 4H) 3.72 (dd, J=11.6, 9.5 Hz, 1 H) 3.96 (dd, J=11.6, 3.1 Hz, 1 H) 3.49-4.14 (m, 4H) 4.37 (m, 1 H) 4.79-4.85 (m, 1 H) 4.87-4.93 (m, 1 H) 7.27 (d, J=1.5 Hz, 1 H) 7.28 (s, 1 H) 7.34-7.38 (m, 1 H) 7.41 (s, 1 H) 7.50 (d, J=8.8 Hz, 1 H) 7.56 (d, J=8.5 Hz, 1 H) 7.62-7.65 (m, 1 H) 7.96 (br. s., 1 H) 8.38 (s, 1 H) 9.60 (s, 1 H) 10.86 (br. s., 1 H) 10.90 (br. s., 1 H)

By analogous procedure the following products have been prepared:

(8R)-6-[5-{[(5-[(tert-butoxycarbonyl)amino]-1H-indol-2-yl)carbonyl]amino}-1H-indo-2-yl)carbonyl]-8-(chloromethyl)-1-methy-7,8-dihydro-6H-thieno[3,2-e]indo-4-yl 4-methylpiperazine-1-carboxylate [(II)](compd. 27)

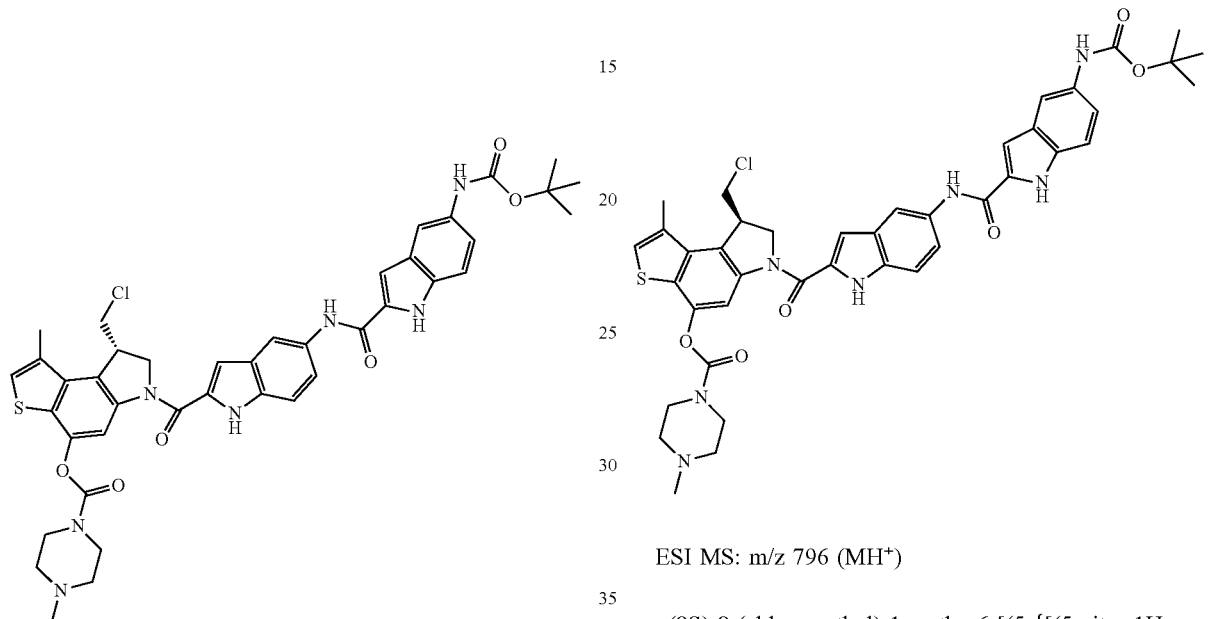

ESI MS: m/z 796 (MH$^+$)

(8S)-8-(chloromethyl)-1-methy-6-[(5-{[(5-nitro-1H-idol-2-yl)carbonyl]amino}-1H-indol-2-yl)carbonyl]-7,8-dihydro-6H-thieno[3,2-e]indol-4-yl-4-methylpiperazine-1-piperazine-1-carboxylate [(II)] (compd. 31)

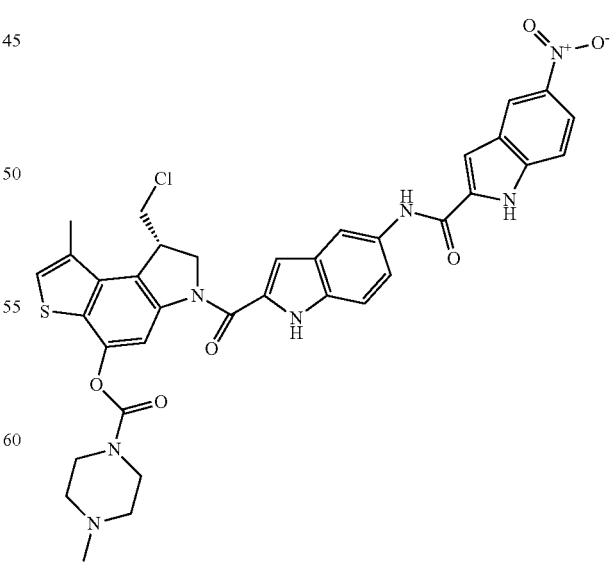

ESI MS: m/z 726 (MH$^+$)

(8R) 8-(chloromethyl)-1-methyl-6-[(5-{[(5-nitro-1H-indol-2-yl)carbonyl]amino}-1H-indo-2-yl)carbonyl]-7,8-dihydro-6H-thieno[3,2-e]indol-4-yl 4-methylpiperazine-1-carboxylate [(II)] (compd. 32)

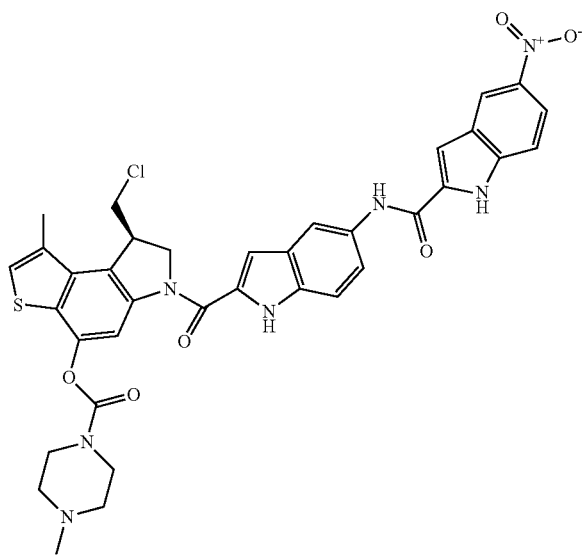 [SMILES: Cc1csc2c(OC(=O)N3CCN(C)CC3)cc3c(c12)[C@@H](CCl)CN3C(=O)c1cc2cc(NC(=O)c3cc4cc([N+](=O)[O-])ccc4[nH]3)ccc2[nH]1]

ESI MS: m/z 726 (MH+)

Deprotection (8S)-6-[(5-{[(5-amino-1H-indol-2-yl)carbonyl]amino}-1H-indo-2-yl)carbonyl]-8-(chloromethyl)-1-methyl-7,8-dihydro-6H-thieno[3,2-e]indol-4-yl 4-methylpiperazine-1-carboxylate hydrochloride [(II)] (compd. 23)

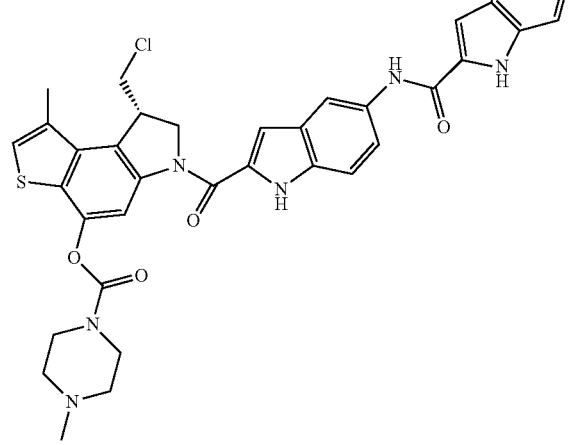

A solution of compd. 22 (22 mg, 0.0276 mmol) in 3.5 M HCl-EtOAc (5 mL) was stirred for 30 minutes before removing the solvent under a steady stream of nitrogen and affording the desired product as hydrochloride salt (18 mg, 89%).

ESI MS: m/z 696 (MH+)

¹H NMR (500 MHz, DMSO-d$_6$) δ ppm 2.59 (s, 3 H) 2.76 (br. s, 3H) 3.05-3.42 (m, 4H) 3.75 (dd, J=10.8, 7.9 Hz, 1 H) 3.95-4.01 (m, 1 H) 3.58-4.08 (m, 4H) 4.32-4.40 (m, 1 H) 4.67 (d, J=11.1 Hz, 1 H) 4.75-4.83 (m, 1 H) 6.92 (br. s., 1 H) 7.21 (br. s., 1 H) 7.23 (s, 1 H) 7.30 (br. s., 1 H) 7.37 (d, J=8.4 Hz, 1 H) 7.49-7.52 (m, 1 H) 7.55 (s, 1 H) 7.57-7.60 (m, 1 H) 8.16 (s, 1 H) 8.24 (s, 1 H) 10.15 (br. s., 1 H) 11.67 (br. s., 1H) 11.70 (s, 1 H)

By analogous procedure the following products have been prepared:

(8R)-6-[(5-{[(5-amino-1H-indol-2-yl)carbonyl]amino}-1H-indol-2-yl)carbonyl]-8-(chloromethyl)-1-methyl-7,8-dihydro-6H-thieno[3,2-e]indol-4-yl 4-methylpiperazine-1-carboxylate hydrochloride [(II)] (compd. 28)

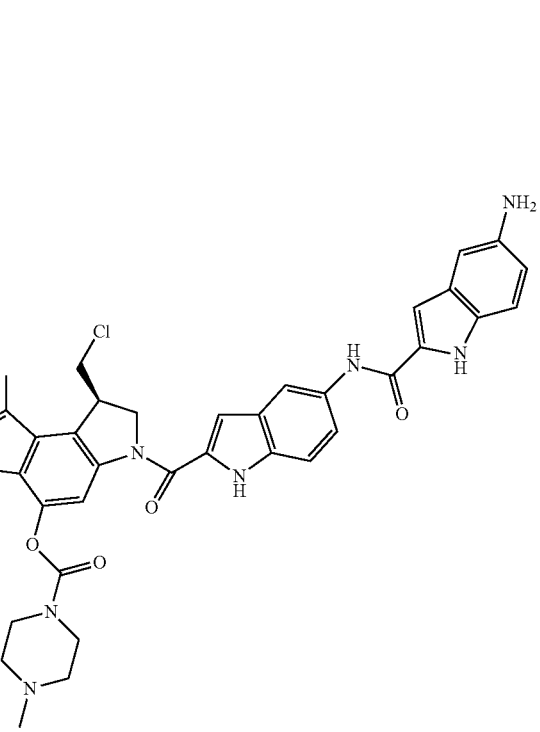

ESI MS: m/z 697 (MH+)

89
(8S)-8-(chloromethyl)-6-[(5-{[(5-hydroxy-1H-indol-2-yl)carbonyl]amino}-1H-indol-2-yl)carbonyl]-1-ethyl-7,8-dihydro-6H-thieno[3,2-e]indol-4-yl 4-methylpiperazine-1-carboxylate [II)] (compd. 33)
90
(8R)-8-(chloromethyl)-6-[(5-{[(5-hydroxy-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate [(II)] (compd. 34)
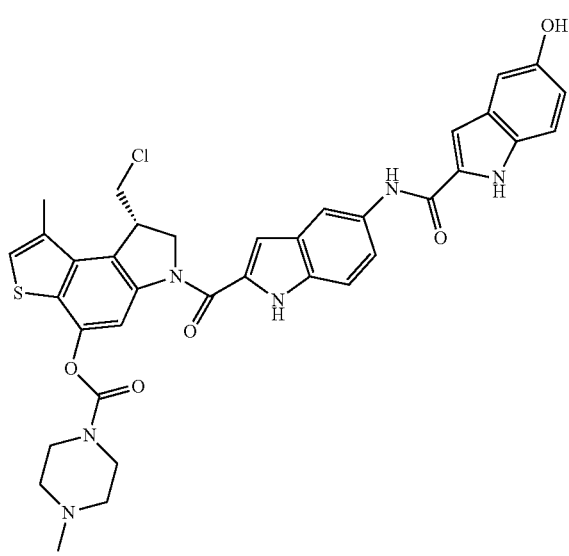 [SMILES: Cc1csc2c(OC(=O)N3CCN(C)CC3)cc3c(c12)[C@H](CCl)CN3C(=O)c1cc2cc(NC(=O)c3cc4cc(O)ccc4[nH]3)ccc2[nH]1]
ESI MS: m/z 697 (MH⁺)
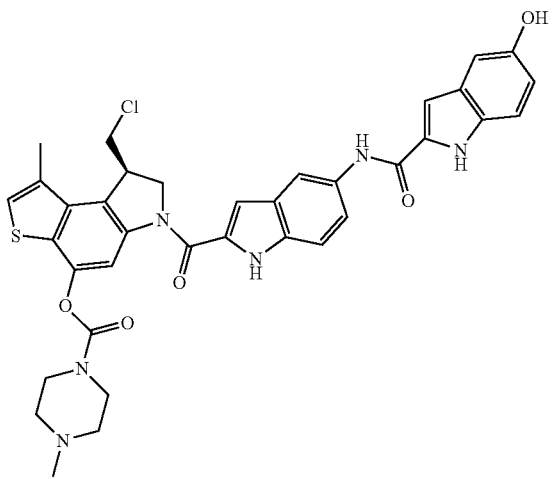 [SMILES: Cc1csc2c(OC(=O)N3CCN(C)CC3)cc3c(c12)[C@@H](CCl)CN3C(=O)c1cc2cc(NC(=O)c3cc4cc(O)ccc4[nH]3)ccc2[nH]1]
ESI MS: m/z 697 (MH⁺)
Example 5
Step c, Deprotection
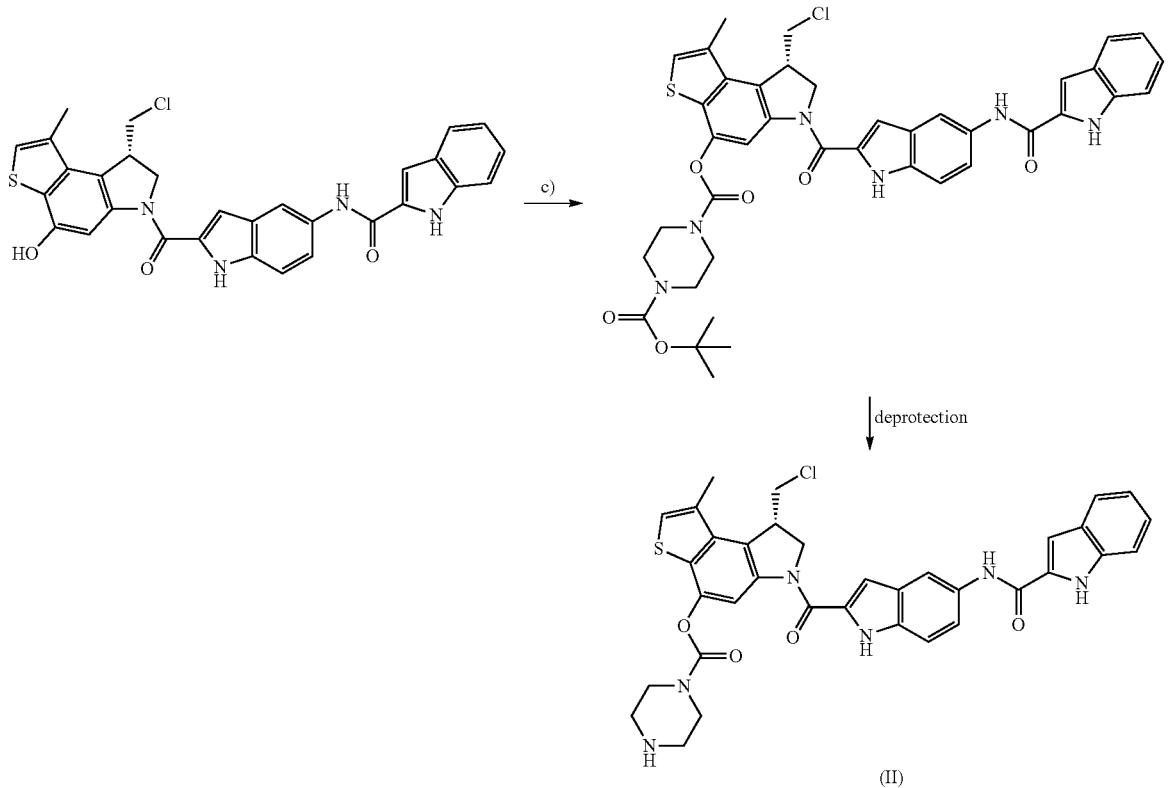 [SMILES: Cc1csc2c(O)cc3c(c12)[C@H](CCl)CN3C(=O)c1cc2cc(NC(=O)c3cc4ccccc4[nH]3)ccc2[nH]1 ; Cc1csc2c(OC(=O)N3CCN(C(=O)OC(C)(C)C)CC3)cc3c(c12)[C@H](CCl)CN3C(=O)c1cc2cc(NC(=O)c3cc4ccccc4[nH]3)ccc2[nH]1 ; Cc1csc2c(OC(=O)N3CCNCC3)cc3c(c12)[C@H](CCl)CN3C(=O)c1cc2cc(NC(=O)c3cc4ccccc4[nH]3)ccc2[nH]1 ; "(II)"]

Step c

Preparation of tert-butyl (8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl piperazine-1,4-dicarboxylate [(II)]

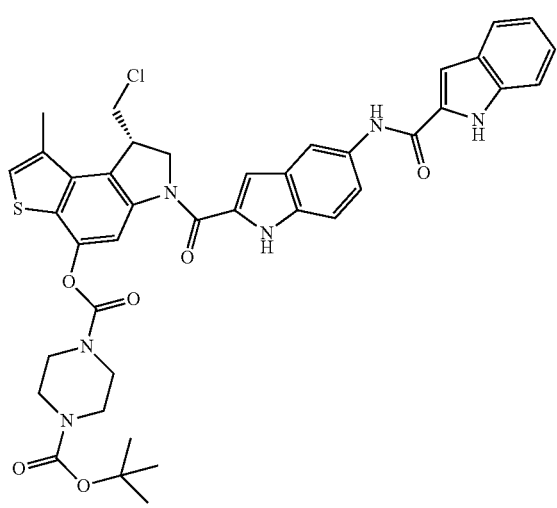 [SMILES: Cc1csc2c(OC(=O)N3CCN(C(=O)OC(C)(C)C)CC3)cc3c(c12)[C@H](CCl)CN3C(=O)c1cc2cc(NC(=O)c3cc4ccccc4[nH]3)ccc2[nH]1]

N-(2-{[(8S)-8-chloromethyl)-4-hydroxy-1-methyl-7,8-dihydro-6H-thieno[3,2-e]indol-6-yl]carbonyl}-1H-indol-5-yl)-1H-indole-2-carboxamide (111 mg, 0.2 mmol), prepared as reported in GB2344818, was dissolved in dry DCM (15 mL) and to this solution tert-butyl 4-(chlorocarbonyl)piperazine-1-carboxylate (100 mg, 0.4 mmol) and N,N-dimethylaminopyridine (55 mg, 0.45 mmol) were added. The reaction mixture was stirred at room temperature under nitrogen atmosphere for 16 h. The solvent was evaporated and the residue was dissolved in EtOAc, the resulting organic layer was washed with brine (×4), dried (Na$_2$SO$_4$) and concentrated in vacuo. The crude residue was purified by flash chromatography (hexane-acetone 7:3) to afford the title compound (30 mg, 19%).

ESI MS: m/z 767 (MH$^+$)

$^1$H NMR (500 MHz, acetone-d$_6$) δ ppm 1.48 (s, 9 H) 2.65 (d, J=1.01 Hz, 3 H) 3.55 (br. s., 4 H) 3.60 (br. s., 2 H) 3.73 (dd. J=11.36, 9.59 Hz, 1 H) 3.79 (br. s., 2 H) 3.97 (dd, J=11.36, 2.78 Hz, 1 H) 4.33-4.42 (m, 1 H) 4.80-4.86 (m, 1 H) 4.89-4.94 (m, 1 H) 7.10 (t, J=7.19 Hz, 1 H) 7.23-7.27 (m, 1 H) 7.28 (s, 1 H) 7.34 (d, J=1.51 Hz, 1 H) 7.42 (s, 1 H) 7.53-7.57 (m, 1 H) 7.60 (d, J=8.08 Hz, 1 H) 7.61-7.65 (m, 1 H) 7.67 (d, J=8.08 Hz, 1 H) 8.29 (s, 1 H) 8.38 (d, J=1.26 Hz, 1 H) 9.56 (s, 1 H) 10.89 (br. s., 2 H).

Deprotection (8S)-8-(chloromethyl)-6-({5-[(1H-indo-2-yl}carbonyl)amino]-1H-indo-2-ylcarbonyl)-1-methyl-7,8-dihydro-6H-thieno[3,2-e]indol-4-yl piperazine-1-carboxylate [(II)] (compd. 24)

A solution of the intermediate (25 mg, 0.0326 mmol) in 3.5 M HCl-EtOAc (5 mL) was stirred for 2 h. After evaporation of the solvent under a steady stream of nitrogen, the residue was dried in vacuo to afford the compd. 9 (11 mg, 48%).

ESI MS: m/z 667 (MH$^+$)

Example 6

Step e'''

N-[6-(2,5-dioxo-2,5-dihydro-1H-pyrrol-1-yl)hexanoyl]-L-valyl-N~5~-carbamoyl-N-[4-({[{3-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide [(IV)] (compd. 35)

Step e'''

To a solution of N-(2-{[(8S)-8-(chloromethyl)-4-hydroxy-1-methyl-7,8-dihydro-6H-thieno[3,2-e]indol-6-yl]carbonyl}-1H-indol-5-yl)-5-[2-(pyrrolidin-1-yl)ethoxy]-1H-indole-2-carboxamide (Compd 17) (5 mg, 0.0071 mmol) in DCM (1 ml) and THF (0.5 mL) were added 4-nitrophenyl chloroformate (3.1 mg, 0.0156 mmol) and triethylamine (2.2 mL, 0.0156 mmol). The resulting mixture was stirred at room temperature for 6 hours. N-[6-(2,5-dioxo-2,5-dihydro-1H-pyrrol-1-yl)hexanoyl]-L-valyl-N$^5$-carbamoyl-N-{4-[({[2,2-dimethyl-3-(methylamino)propyl] (methyl)carbamoyl}oxy)methyl]phenyl}-L-omithinamide (XX)' (16 mg, 0.018 mmol) and triethylamine (3 mL, 0.021 mmol) were added. The mixture thus obtained was stirred at room temperature overnight, diluted with DCM and washed with

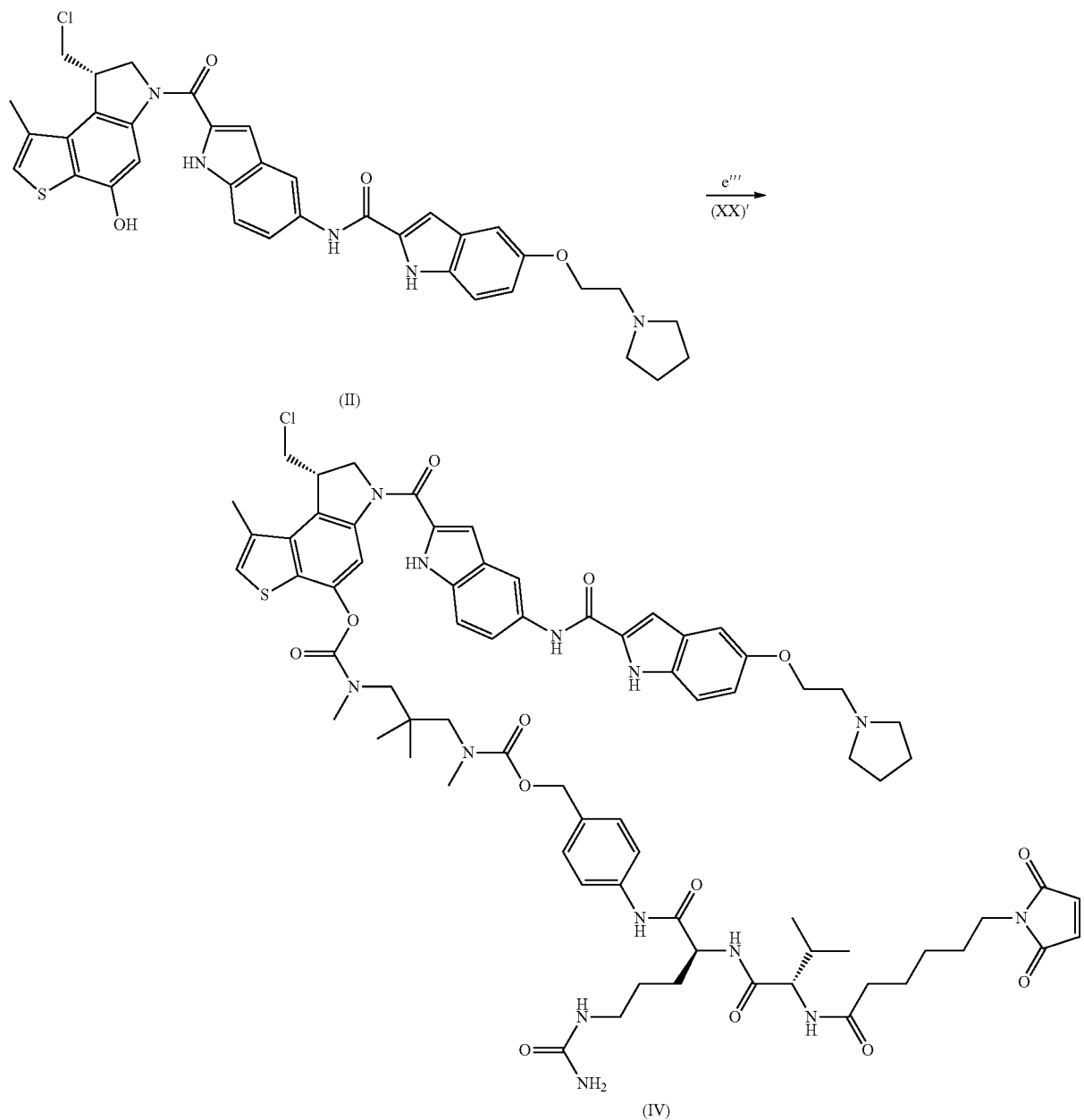

a saturated solution of aqueous NaHCO₃. The crude residue was purified by flash chromatography (DCM-MeOH 100:15) to afford the title compound (2 mg, 20%).

ESI MS: m/z 1422 (MH+)

¹H NMR (500 MHz, methanol-d₃) δ ppm 0.82-1.45 (m 29H) 2.68 (s, 3H) 2.90-3.61 (m, 20 H) 3.84-4.34 (m, 8H) 4.49 (m, 1H) 5.04-5.14 (m, 2H) 6.70-6.77 (m, 2H) 7.01 (dd, J=9.0, 2.4, 1H) 7.18-7.71 (m, 11H) 8.11 (br. s., 2H)

Analogously the following compounds have been prepared:

N-[6-(2,5-dioxo-2,5-dihydro-1H-pyrrol-1 yl)hexanoyl]-L-valyl-N~5~-carbamoyl-N[4-({[{3-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide [(IV)] (Compd 36).

N-[6-2,5-dioxo-2,5-dihydro-1H-pyrrol-1-yl)hexanoyl]-L-valyl-N⁵-carbamoyl-N-[4-({[{3-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide [(IV)] (Compd. 39)

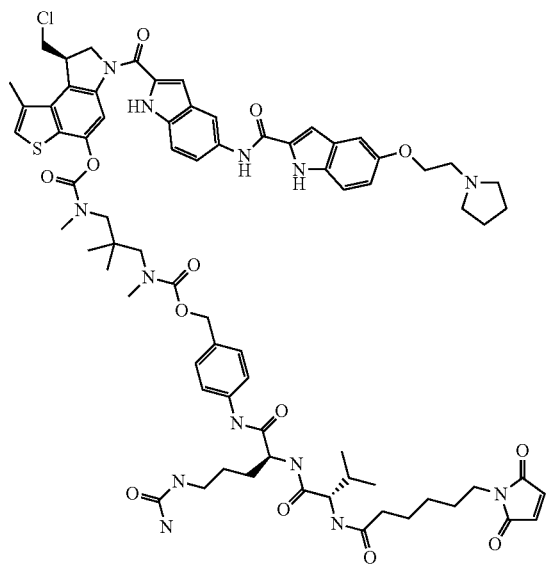 [SMILES: Cc1csc2c(OC(=O)N(C)CC(C)(C)CN(C)C(=O)OCc3ccc(NC(=O)[C@H](CCCNC(N)=O)NC(=O)[C@@H](NC(=O)CCCCCN4C(=O)C=CC4=O)C(C)C)cc3)cc3c(c12)[C@@H](CCl)CN3C(=O)c1cc2cc(NC(=O)c3cc4cc(OCCN5CCCC5)ccc4[nH]3)ccc2[nH]1]

ESI MS: m/z 1424 (MH⁺)

ESI MS: m/z 1264 (MH⁺)

97

N-[6-2,5-dioxo-2,5-dihydro-1H-pyrrol-1-yl)hexanoyl]-L-valyl-N⁵-carbamoyl-N-[4-({[{3-[({[(8R)-8-(chloromethyl)-1-methyl-6-({5-[2-pyrrolidin-1-yl)ethoxy]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide [(IV)] (Compd 40).

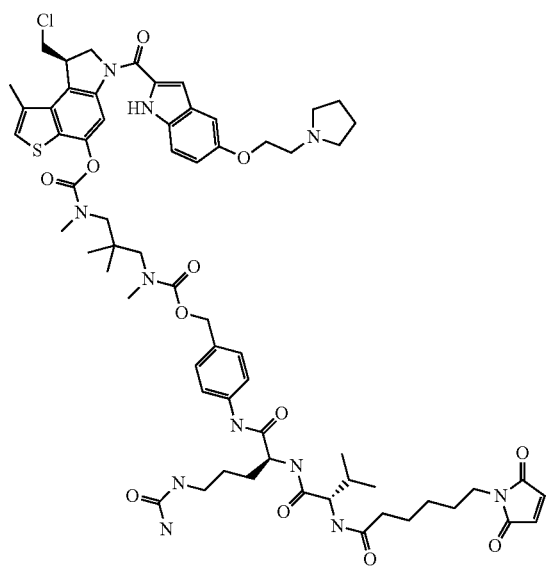 [SMILES: Cc1csc2c(OC(=O)N(C)CC(C)(C)CN(C)C(=O)OCc3ccc(NC(=O)[C@H](CCCNC(N)=O)NC(=O)[C@@H](NC(=O)CCCCCN4C(=O)C=CC4=O)C(C)C)cc3)cc3c(c12)[C@@H](CCl)CN3C(=O)c1cc2cc(OCCN3CCCC3)ccc2[nH]1]

ESI MS: m/z 1264 (MH+)

98

N-[6-2,5-dioxo-2,5-dihydro-1H-pyrrol-1-yl)hexanoyl]-L-valyl-N⁵-carbamoyl-N-[4-({[(3-{[({(8S)-8-(chloromethyl)-1-methyl-6-[(2E)-3-{5-[2-pyrrolidin-1-yl)ethoxy]-1H-indol-2-yl}prop-2-enoyl]-7,8-dihydro-6H-thieno[3,2-e]indol-4-yl}oxy)carbonyl](methyl)amino}-2,2-dimethylpropyl)(methyl)carbamoyl]oxy}methyl)phenyl]-L-ornithinamide [(IV)] (Compd 41).

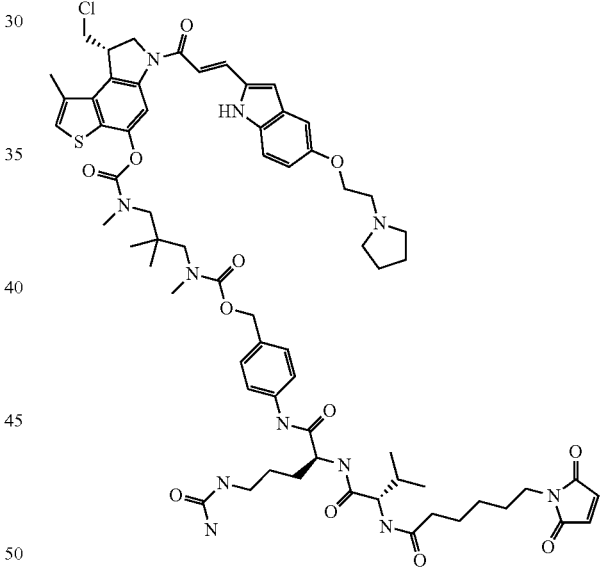

ESI MS: m/z 1290 (MH+)

99

N-[6-2,5-dioxo-2,5-dihydro-1H-pyrrol-1-yl)
hexanoyl]-L-valyl-N⁵-carbamoyl-N-[4-({[(3-
{[({(8R)-8-(chloromethyl)-1-methyl-6-[(2E)-3-{-[2-
(pyrrolidin-1-yl)ethoxy]-1H-indol-2-yl}prop-2-
enoyl]-7,8-dihydro-6H-thieno[3,2-e]indol-4-yl}oxy)
carbonyl](methy)amino}-2,2-dimethylpropyl)
(methyl)carbamoyl]oxy}methyl)phenyl]-L-
ornithinamide [(IV)] (Compd. 42)

100

N-[6-(2,5-dioxo-2,5-dihydro-1H-pyrrol-1-yl)
hexanoyl]-L-phenylalanyl-L-leucyl-N-[4-({[{3-
[({[(8S)-8-(chloromethyl)-1-methyl-6-({5-[({5-[2-
(pyrrolidin-1-yl)ethoxy]-1H-indol-2-yl}carbonyl)
amino]-1H-indol-2-yl}carbonyl)-7,8-dihydro-6H-
thieno[3,2-e]indol-4-yl]oxy}carbonyl)(methyl)
amino]-2,2-dimethylpropyl}(methyl)carbamoyl]
oxy}methyl)phenyl]glycinamide [(IV)] (Compd 46)

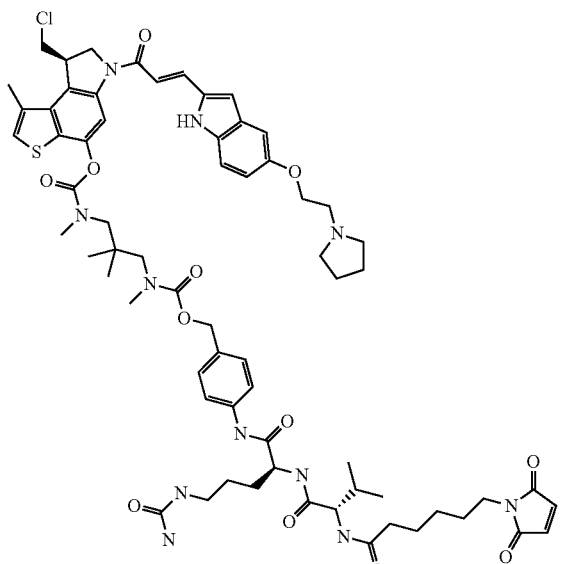

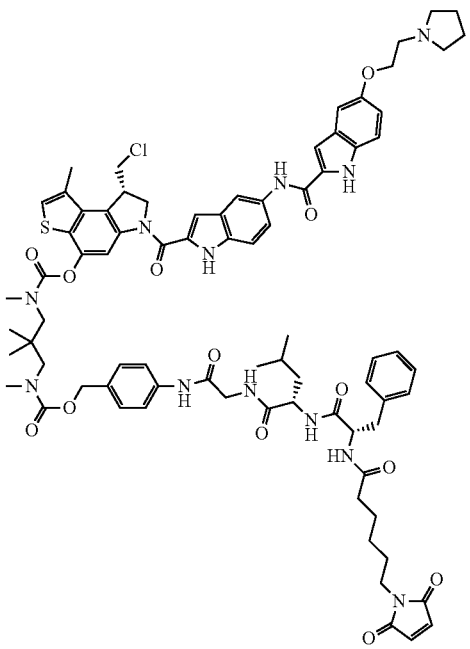 [SMILES: Cc1csc2c(OC(=O)N(C)CC(C)(C)CN(C)C(=O)OCc3ccc(NC(=O)CNC(=O)[C@H](CC(C)C)NC(=O)[C@H](Cc4ccccc4)NC(=O)CCCCCN4C(=O)C=CC4=O)cc3)cc3c(c12)[C@H](CCl)CN3C(=O)c1cc2cc(NC(=O)c3cc4cc(OCCN5CCCC5)ccc4[nH]3)ccc2[nH]1]

ESI MS: m/z 1290 (MH+)

ESI MS: m/z 1483 (MH+)

101

N-[6-(2,5-dioxo-2,5-dihydro-1H-pyrrol-1-yl)hexanoyl]-L-phenylalanyl-L-leucyl-N-[4-({[{3-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]glycinamide [(IV)] (Compd 47)

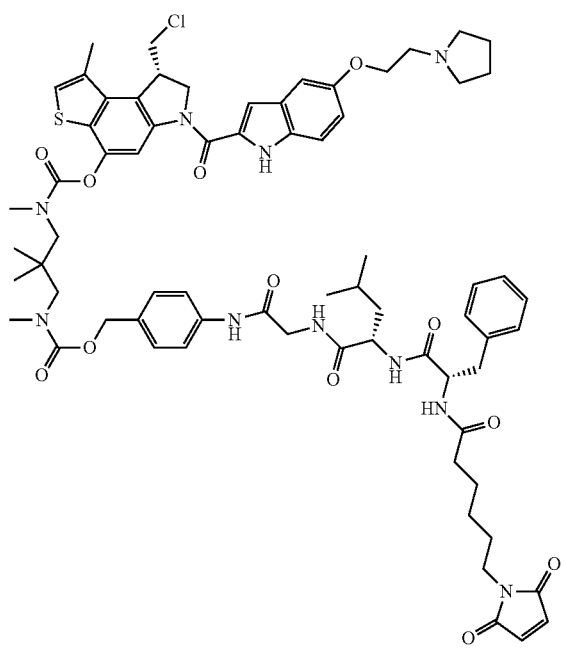 [SMILES: Cc1csc2c(OC(=O)N(C)CC(C)(C)CN(C)C(=O)OCc3ccc(NC(=O)CNC(=O)[C@H](CC(C)C)NC(=O)[C@H](Cc4ccccc4)NC(=O)CCCCCN4C(=O)C=CC4=O)cc3)cc3c(c12)[C@H](CCl)CN3C(=O)c1cc2cc(OCCN3CCCC3)ccc2[nH]1]

ESI MS: m/1325 (MH+)

102

N-[6-(2,5-dioxo-2,5-dihydro-1H-pyrrol-1-yl)hexanoyl]-L-phenylalanyl-L-leucyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]glycinamide [(IV)] (Compd 48)

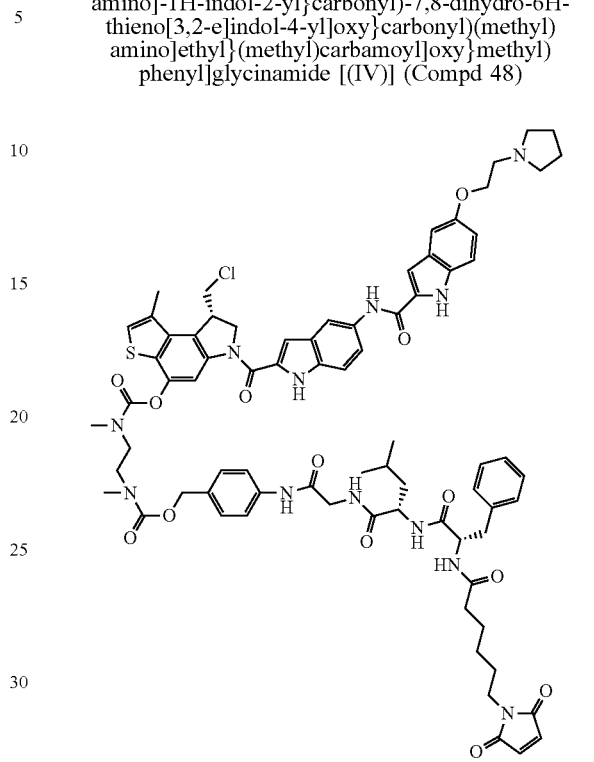

ESI MS: m/z 1441 (MH+)

N-[6-(2,5-dioxo-2,5-dihydro-1H-pyrrol-1-yl)hexanoyl]-L-phenylalanyl-L-leucyl-N-[4-({[{2-[({[(8S)-8-(chloromethyl)-1-methy-6-({5-[2-(pyrrolidin-1-yl)ethoxy]-1H-indo-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]glycinamide [(IV)](Compd 49)

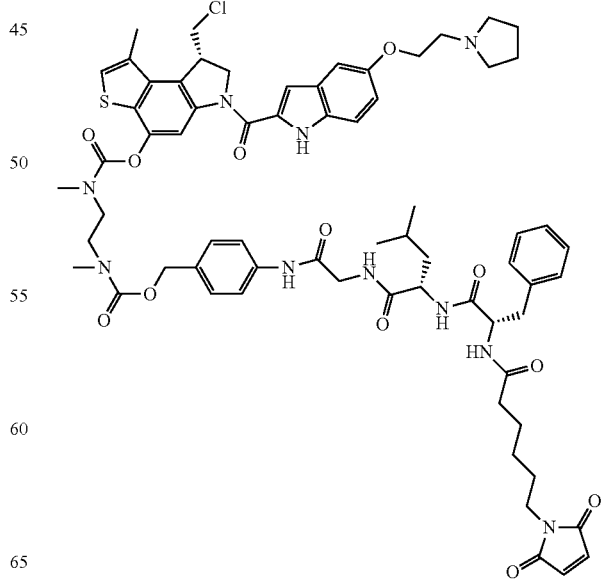

ESI MS: m/z 1283 (MH+)

Example 7

Step c, Deprotection, Step g

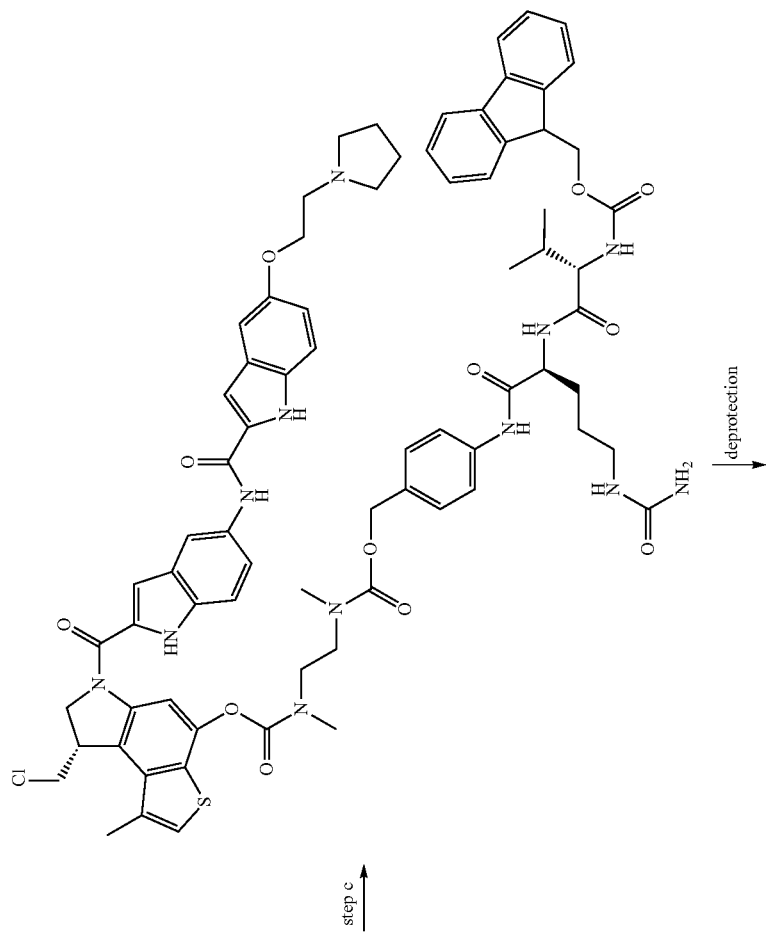
↓ deprotection
↑ step c
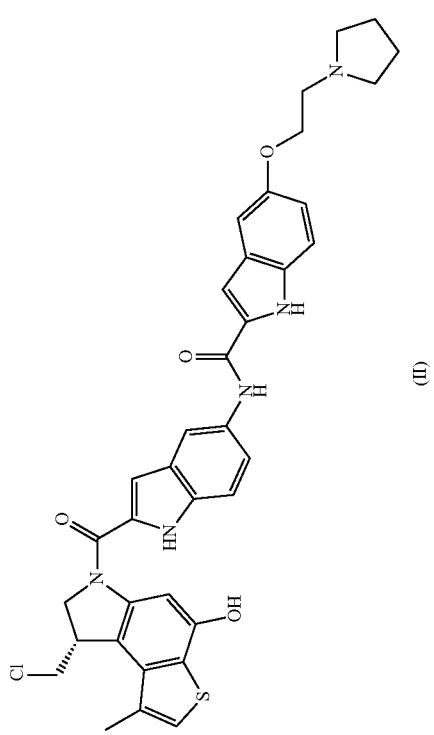
(II)

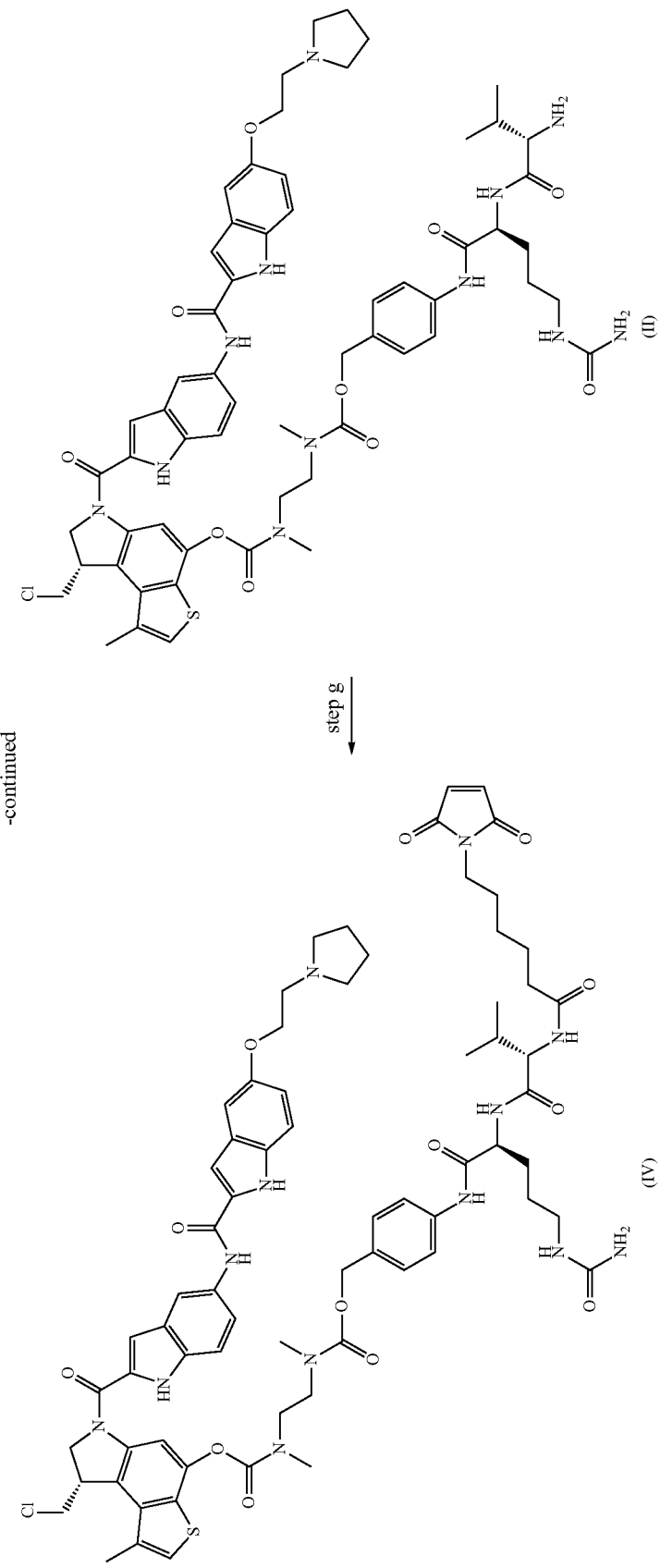

Step c

N-[(9H fluoren-9-ylmethoxy)carbonyl]-L-valyl-N⁵-carbamoyl-N-[4-({[{2-[({[(8S)-8-(chloromethyl)-1-methyl-6-({5-[({5-[2-(pyrrolidin-1-yl)ethoxy]-1H-indol-2 yl}carbonyl)amino]-1H-indol-2-yl}carbonyl)-7,8-dihydro-6H-thieno[3,2-e]indol-4-yl]oxy}carbonyl)methyl)amino]ethyl}(methyl)carbamoyl]oxy}methyl)phenyl]-L-ornithinamide
[(II)]

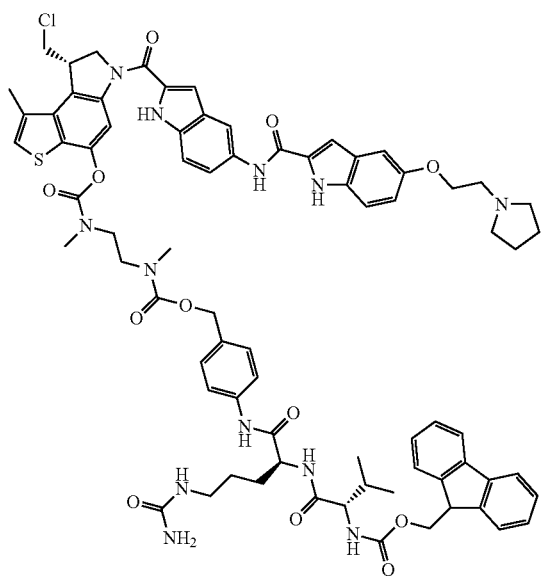 [SMILES: Cc1csc2c(OC(=O)N(C)CCN(C)C(=O)OCc3ccc(NC(=O)[C@H](CCCNC(N)=O)NC(=O)[C@@H](NC(=O)OCC4c5ccccc5-c5ccccc54)C(C)C)cc3)cc3c(c12)[C@H](CCl)CN3C(=O)c1cc2cc(NC(=O)c3cc4cc(OCCN5CCCC5)ccc4[nH]3)ccc2[nH]1]

after treatment with diethyether. The resulting solid compound was diluted with 1 mL of DCM (10% DMF) and N-[(9H-fluoren-9-ylmethoxy)carbonyl]-L-valyl-N⁵-carbamoyl-N-{4-[({methyl[2-(methylamino)ethyl]carbamoyl}oxy)methyl]phenyl}-L-omithinamide hydrochloride (38 mg, 0.05 mmol) and trietylamine (7 mL 0.05 mmol) were added. The mixture was stirred overnight, solvents were evaporated and title compound (12 mg, 42% yield) was isolated by column chromatography purification (DCM/MeOH 8:2).

ESI MS: m/z 1409 (MH+)

¹H NMR (500 MHz, methanol-d₄) δ ppm 2.07 (br. s., 4 H) 2.58 (s, 3 H) 2.93-3.09 (m, 6 H) 3.40-3.69 (m, 8 H) 4.11-4.40 (m, 3 H) 4.43-4.81 (m, 3 H) 4.99-5.17 (m, 2 H) 6.92-7.44 (m, 14 H) 7.46-7.64 (m, 4 H) 7.75 (br. s., 3 H) 8.01-8.22 (m, 2 H) 8.01-8.06 (m, 1 H)

Analogously the following compound has been prepared:

N-[(9H-fluoren-9-ylmethoxy)carbonyl]-L-valyl-N⁵-carbamoyl-N-[4-({[{2-[({[(8S)-8-chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide

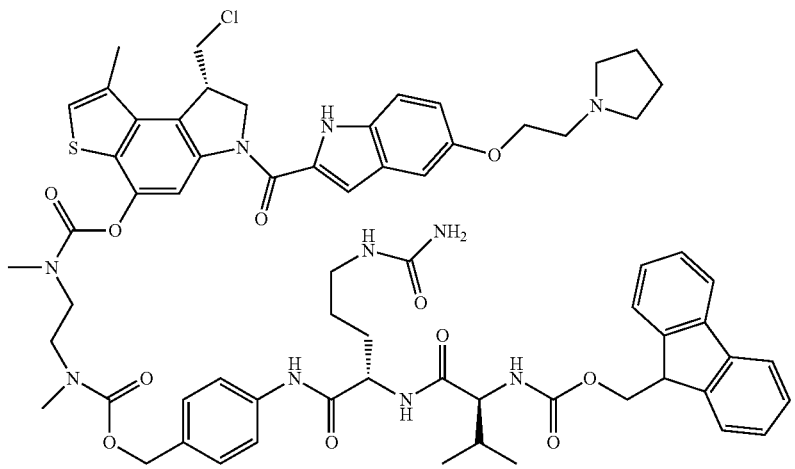 [SMILES: Cc1csc2c(OC(=O)N(C)CCN(C)C(=O)OCc3ccc(NC(=O)[C@H](CCCNC(N)=O)NC(=O)[C@@H](NC(=O)OCC4c5ccccc5-c5ccccc54)C(C)C)cc3)cc3c(c12)[C@H](CCl)CN3C(=O)c1cc2cc(OCCN3CCCC3)ccc2[nH]1]

To a solution of N-(2-{[(8S)-8-(chloromethyl)-4-hydroxy-1-methyl-7,8-dihydro-6H-thieno[3,2-e]indol-6-yl]carbonyl}-1H-indol-5-yl)-5-[2-(pyrrolidin-1-yl)ethoxy]-1H-indole-2-carboxamide hydrochloride (13 mg, 0.02 mmol) in THF/DCM 1:1 (2 mL) at 0° C. under nitrogen atmosphere, were added 4-nitrophenyl chloroformate (20 mg, 0.1 mmol) and triethylamine (20 mL, 0.14 mmol). The mixture was stirred at room temperature for 6 hours, solvent was evaporated and the residue was isolated by filtration ESI MS: m/z 1251 (MH+)

¹H NMR (500 MHz, methanol-d₄) δ ppm 0.94-1.01 (m, 6 H) 1.51-1.95 (m, 4 H) 2.12 (br. s., 5 H) 2.48-2.62 (m, 3 H) 2.89-3.05 (m, 4 H) 3.40-3.54 (m, 4 H) 3.46-3.65 (m, 4 H) 3.58-3.74 (m, 2 H) 3.75-4.05 (m, 1 H) 4.08-4.42 (m, 3 H) 4.50 (m, 1 H) 4.55-4.81 (m, 4 H) 4.96-5.20 (m, 2 H) 6.92-7.81 (m, 17 H) 8.04 (br. s., 1 H)

Deprotection

L-valyl-$N^5$-carbamoyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide [(II)] (Compd 50)

ethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methy)amino]ethyl}methyl)carbamoyl]oxy}methyl)phenyl]-L-ornithinamide (11 mg, 0.0078 mmol) in DMF (1 mL) was added piperidine (4 mL, 0.039 mmol). The mixture was stirred 1 hour at room temperature, solvent was evaporated and the resulting title compound was used without further purification.

Analogously the following compound has been prepared:

L-valyl-$N^5$-carbamoyl-N-[4-({[{2-[({[(8S)-8-chloromethyl)-1-methyl-6-({5-[2-pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide [(II)] (Compd 51)

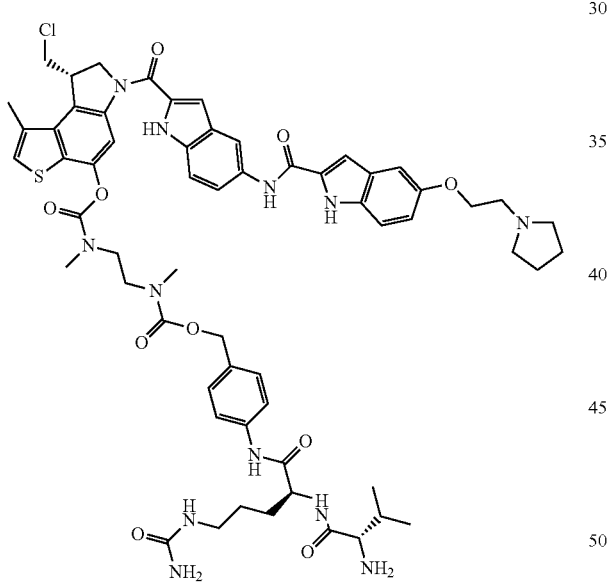

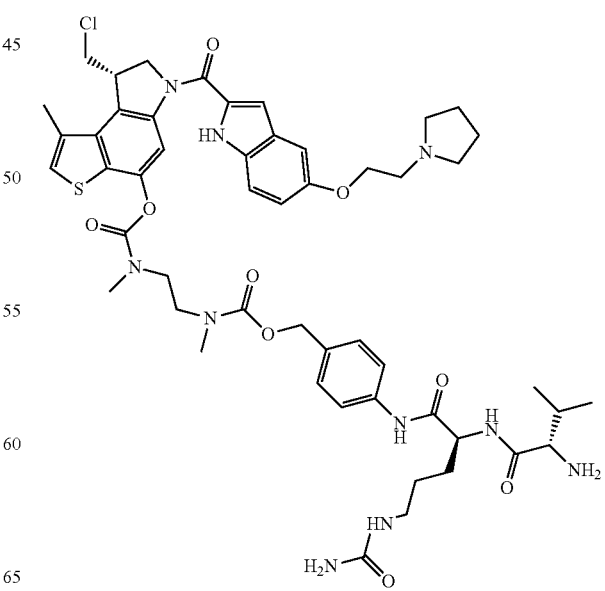

To a solution of N-[(9H-fluoren-9-ylmethoxy)carbonyl]-L-valyl-$N^5$-carbamoyl-N-[4-({[{2-[({[(8S)-8-(chlorom- Step g N-[6-(2,5-dioxo-2,5-dihydro-1H-pyrrol-1-yl)hexanoyl]-L-valyl-N⁵-carbamoyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8 dihydro-6H-thieno[3,2-e]indol-4-yl]oxy}carbonyl)(methyl)amino]ethyl}(methyl)carbamoyl]oxy}methyl)phenyl]-L-ornithinamide [(IV)] (Compd 52)

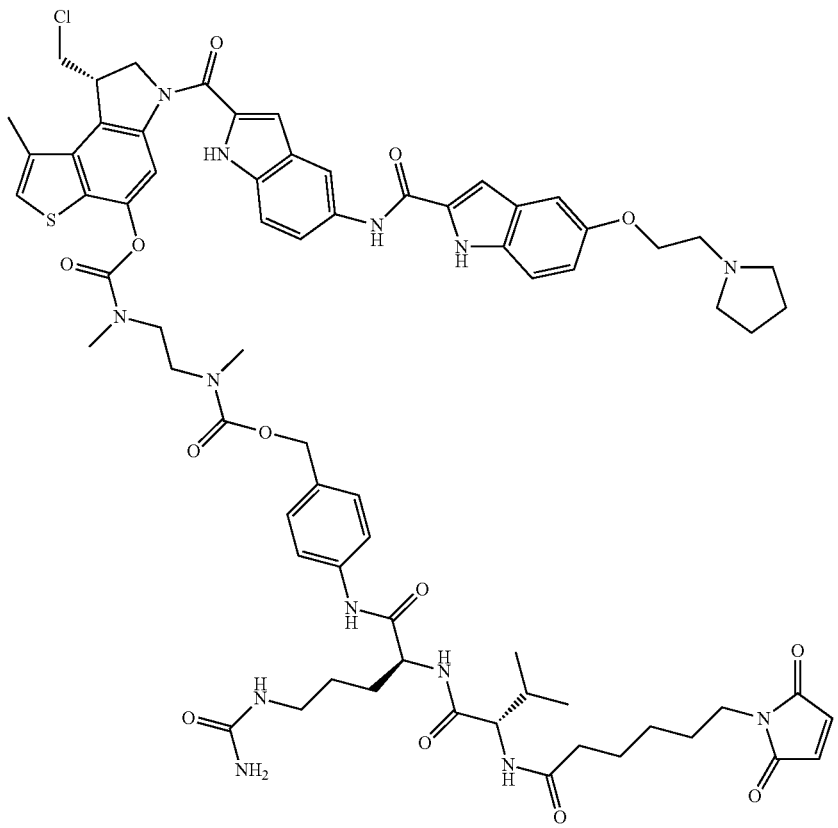 [SMILES: Cc1csc2c(OC(=O)N(C)CCN(C)C(=O)OCc3ccc(NC(=O)[C@H](CCCNC(N)=O)NC(=O)[C@@H](NC(=O)CCCCCN4C(=O)C=CC4=O)C(C)C)cc3)cc3c(c12)[C@H](CCl)CN3C(=O)c1cc2cc(NC(=O)c3cc4cc(OCCN5CCCC5)ccc4[nH]3)ccc2[nH]1]

To a solution of L-valyl-N⁵-carbamoyl-N-[4-({[{2-[({(8S)-8-chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino)ethyl}(methyl)carbamoyl]oxy}methyl)phenyl]-L-ornithinamide (4.6 mg, 0.0039 mmol) in 1 mL of DCM (10% DMF), were added 1-{6-[(2,5-dioxopyrrolidin-1-yl)oxy]-6-oxohexyl}-1H-pyrrole-2,5-dione (3.6 mg, 0.0117 mmol) and triethylamine (2.2 mL, 0.0156 mmol). The mixture was stirred at room temperature for 3 hours, solvents were evaporated and the title compound (2.2 mg, 41% yield) was isolated by column chromatography purification (DCM/MeOH 8:2).

ESI MS: m/z 1380 (MH+)

¹H NMR (500 MHz, methanol-d₄) δ ppm 1.98 (br. s., 4 H) 2.60-2.63 (m, 3 H) 2.89-3.11 (m, 6 H) 3.39-3.72 (m, 10H) 4.07-4.75 (m, 7H) 4.98-5.17 (m, 2H) 6.74 (br. s., 2 H) 7.00 (m, 2 H) 7.07-7.45 (m, 8 H) 7.52 (br. s., 3 H) 8.07-8.11 (m, 1 H)

Analogously the following compounds have been prepared:

N-[19-(2,5-dioxo-2,5-dihydro-1H-pyrrol-1-yl)-17-oxo-4,7,10,13-tetraoxa-16-azanonadecan-1-oyl]-L-valyl-N⁵-carbamoyl-N-[4-({[{2-[({[(8S)-8-(chloromethyl)-1-methyl-6-({5-[({5-[2-pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide [(IV)] (Compd 53)

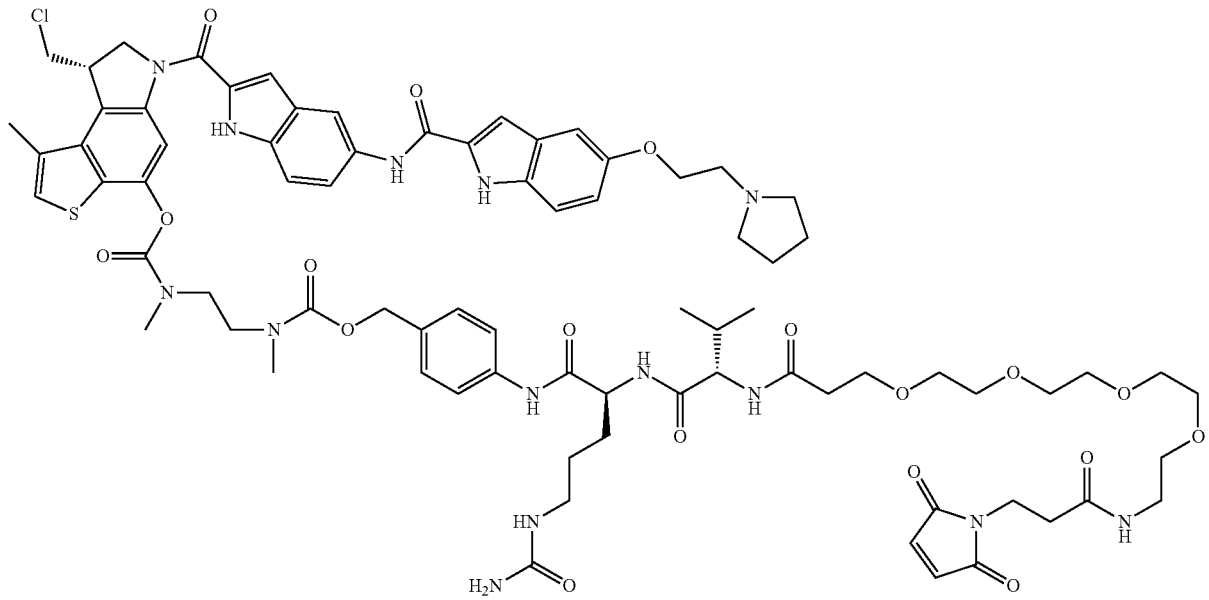 [SMILES: Cc1csc2c(OC(=O)N(C)CCN(C)C(=O)OCc3ccc(NC(=O)[C@H](CCCNC(N)=O)NC(=O)[C@@H](NC(=O)CCOCCOCCOCCOCCNC(=O)CCN4C(=O)C=CC4=O)C(C)C)cc3)cc3c(c12)[C@H](CCl)CN3C(=O)c1cc2cc(NC(=O)c3cc4cc(OCCN5CCCC5)ccc4[nH]3)ccc2[nH]1]

ESI MS: m/z 1585 (MH+)

N-[6-(2,5-dioxo-2,5-dihydro-1H-pyrrol-1-yl)hexanoyl]-L-valyl-N⁵-carbamoyl-N-[4-({[{2-[({[(8S)-8-(chloromethyl)-1-methyl-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide [(IV)](Compd 54)

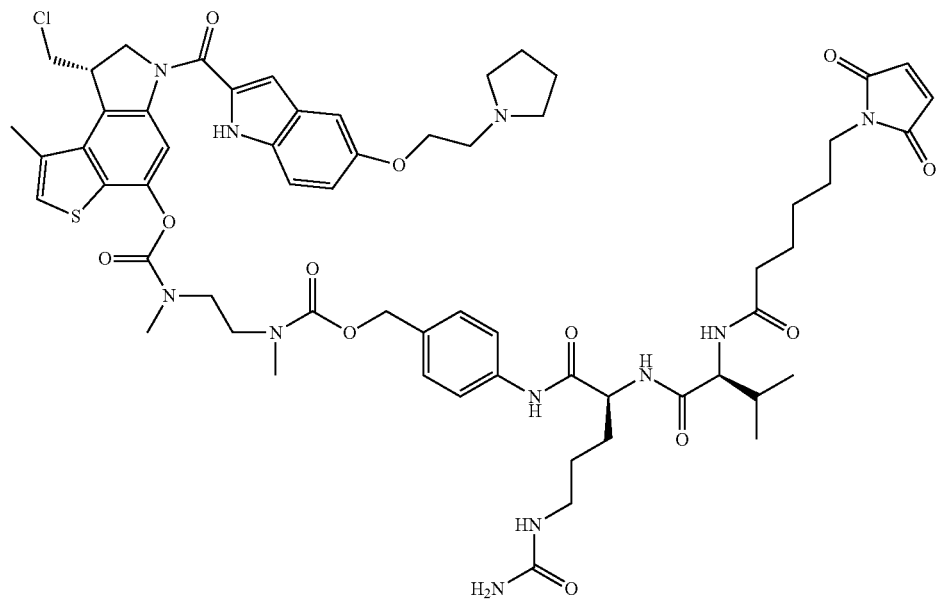 [SMILES: Cc1csc2c(OC(=O)N(C)CCN(C)C(=O)OCc3ccc(NC(=O)[C@H](CCCNC(N)=O)NC(=O)[C@@H](NC(=O)CCCCCN4C(=O)C=CC4=O)C(C)C)cc3)cc3c(c12)[C@H](CCl)CN3C(=O)c1cc2cc(OCCN3CCCC3)ccc2[nH]1]

ESI MS: m/z 1222 (MH+)

¹H NMR (400 MHz, dmf-d7) δ ppm 0.95 (t, J=7.8 Hz, 6 H) 2.16 (m, 1 H) 2.66 (br. s., 3 H) 2.99-3.09 (m, 3 H) 3.09-3.29 (m, 3 H) 3.59 (br. s., 2 H) 3.69 (br. s., 2 H) 3.81 (br. s., 2 H) 4.04 (d, J=10.7 Hz, 1 H) 4.31-4.47 (m, 2 H) 4.61 (br. s., 1 H) 4.83 (br. s., 2 H) 5.11 (d, J=15.7 Hz, 2 H) 5.60 (s, 2 H) 6.29 (br. s., 1 H) 7.00 (m, 3 H) 7.30 (m, 2 H) 7.53 (d, J=8.5 Hz, 2 H) 7.88 (d, J=8.2 Hz, 1 H) 8.13 (d, J=7.8 Hz, 1 H) 8.27 (s, 1 H) 10.1 (m, 1 H) 11.61 (br. s., 1 H)

Preparation of the Intermediate

N-[6-(2,5-dioxo-2,5-dihydro-1H-pyrrol-1-yl)hexanoyl]-L-valyl-N⁵-carbamoyl-N-{4-[({[2,2-dimethyl-3-(methylamino)propyl](methyl)carbamoyl}oxy)methyl]phenyl}-L-ornithinamide (XX)'

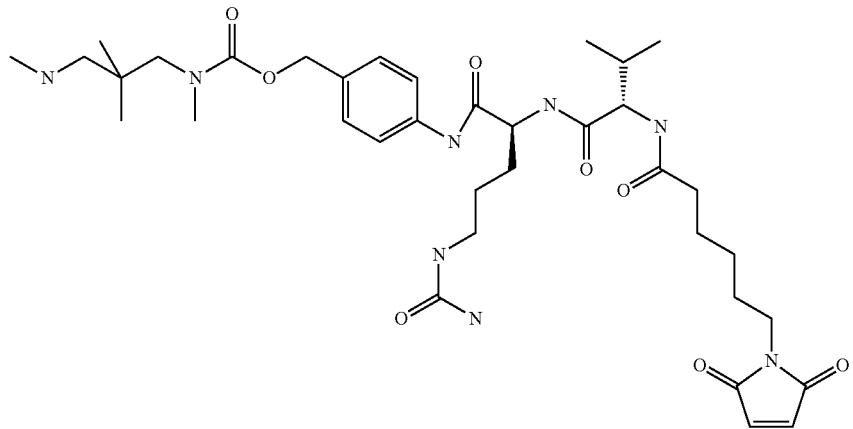 [SMILES: CNCC(C)(C)CN(C)C(=O)OCc1ccc(NC(=O)[C@H](CCCNC(N)=O)NC(=O)[C@@H](NC(=O)CCCCCN2C(=O)C=CC2=O)C(C)C)cc1]

Step 1

N,N'-(2,2-dimethylpropane-1,3-diyl)diformamide

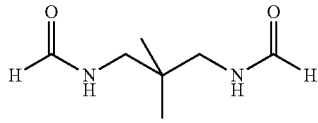

In a round bottomed flask, commercially available 2,2-dimethylpropane-1,3-diamine (851 mg, 8.32 mmol) was reacted with ethylformiate (4.2 ml). The reaction mixture was stirred at 60° C. for 3 hours, until no starting material was detectable (TLC analysis, MeOH:CH₂Cl₂=2:8). The reaction mixture was then evaporated under vacuum, affording the crude product (1.4 g, oil).

ESI MS: m/z 159 (MH+)

¹H NMR (600 MHz, DMSO-d₆) ppm 0.79 (s, 6 H) 2.92 (d, J=6.41 Hz, 4 H) 7.94 (br. s., 2 H) 8.05-8.09 (m, 2 H)

Step 2

N,N',2,2-tetramethylpropane-1,3-diamine

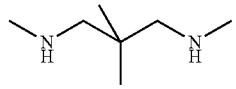

In a dried round bottomed flask, containing N,N'-(2,2-dimethylpropane-1,3-diyl)diformamide (1.4 g, 8.85 mmol) cooled at 0° C. under argon atmosphere, a solution (24 ml) of Lithium Aluminium Hydride in tetrahydrofuran (1M) was added. The reaction mixture was stirred at room temperature for 28 hours. After cooling at 0° C., a solution of water in tetrahydrofuran was added, and the resulting mixture was filtered on a celite pad. The filtrate was dried over anhydrous sodium sulfate, filtered and the product thus obtained as a tetrahydrofuran solution was used without further purification in the next step.

Step 3

2-(biphenyl-4-yl)propan-2-yl [2,2-dimethyl-3-(methylamino)propyl]methylcarbamate

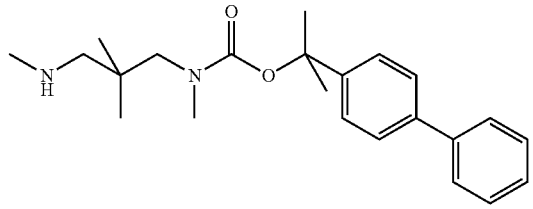 [SMILES: CNCC(C)(C)CN(C)C(=O)OC(C)(C)c1ccc(-c2ccccc2)cc1]

Commercial methyl 4-[({[2-(biphenyl-4-yl)propan-2-yl]oxy}carbonyl)oxy]benzoate (5.54 mmol, 2.16 g) was added to the tetrahydrofuran solution of N,N',2,2-tetramethylpropane-1,3-diamine. The reaction mixture was stirred at room temperature for 24 hours. The solvent was then evaporated under vacuum and the residue was purified by flash chromatography (MeOH:CH₂Cl₂=1:9) affording the desired product (848 mg).

MS (ESI): 369 (MH+)

¹H NMR (600 MHz, DMSO-d₆) δ ppm 0.73-0.83 (m, 5 H) 0.91 (br. s., 3 H) 1.65-1.77 (m, 6 H) 2.78 (br. s., 1 H) 7.32-7.38 (m, 1 H) 7.41 (d, J=8.43 Hz, 2 H) 7.46 (t, J=7.69 Hz, 2 H) 7.58-7.69 (m, 4 H)

Analogously the following compound has been prepared:
2-(biphenyl-4-yl)propan-2-yl methyl[2-(methyl-amino)ethyl]carbamate

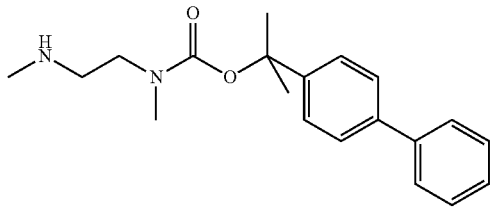 [SMILES: CNCCN(C)C(=O)OC(C)(C)c1ccc(-c2ccccc2)cc1]

MS (ESI): 327 (MH+)

¹H NMR (401 MHz, DMSO-d₆) δ ppm 1.70-1.75 (m, 6 H) 2.23-2.39 (m, 3 H) 7.30-7.39 (m, 1 H) 7.40-7.49 (m, 4 H) 7.58-7.63 (m, 2 H) 7.63-7.68 (m, 2 H)

Step 4

N-[6-(2,5-dioxo-25-dihydro-1H-pyrrol-1-yl)hexanoyl]L-valyl-N-{4-[11-(biphenyl-4-yl)-4,6,6,8,11-pentamethyl-3,9-dioxo-2,10-dioxa-4,8-diazadodec-1-yl]phenyl}-N⁵-carbamoyl-L-ornithinamide

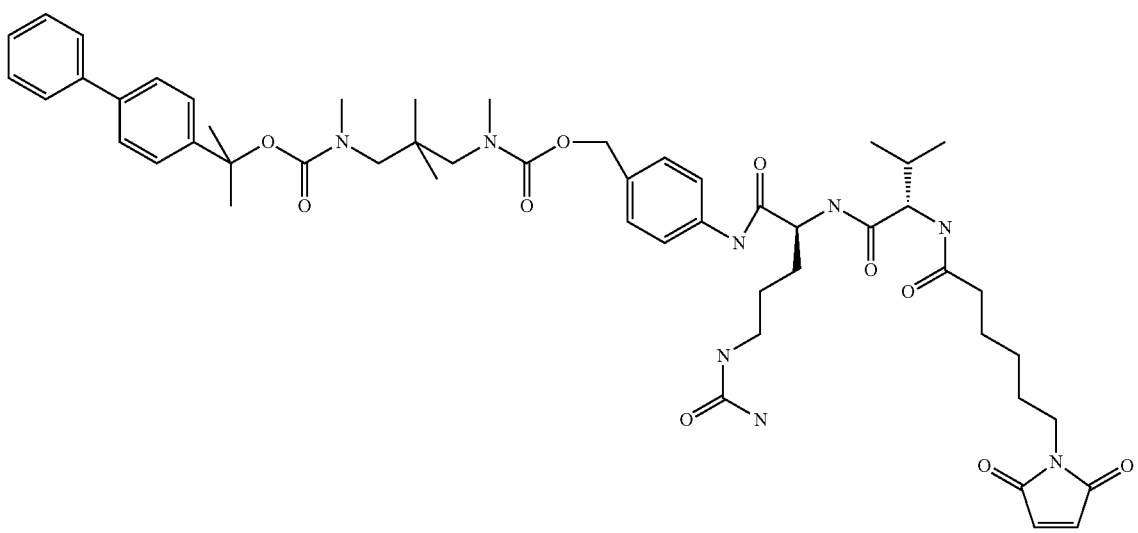 [SMILES: CC(C)[C@H](NC(=O)CCCCCN1C(=O)C=CC1=O)C(=O)N[C@@H](CCCNC(N)=O)C(=O)Nc1ccc(COC(=O)N(C)CC(C)(C)CN(C)C(=O)OC(C)(C)c2ccc(-c3ccccc3)cc2)cc1]

To a solution of N-[6-(2,5-dioxo-2,5-dihydro-1H-pyrrol-1-yl)hexanoyl]-L-valyl-N⁵-carbamoyl-N-[4-({[(4-nitrophenoxy)carbonyl]oxy}methyl)phenyl]-L-omithinamide (0.492 mmol, 363 mg) in anhydrous dimethylsulfoxide (1.0 ml), a solution of 2-(biphenyl-4-yl)propan-2-yl [2,2-dimethyl-3-(methylamino)propyl]methylcarbamate (0.393 mmol, 145 mg) in anhydrous dimethylsulfoxide (0.9 ml) and triethylamine (1.5 mmol, 150 mg) were added. The reaction mixture was stirred at room temperature until no starting material was detectable, then treated with n-hexane (3×6 ml), and the crude residue was used without further purification in the next step.

MS (ESI): 967 (MH+).

Analogously the following compound has been prepared

N-[(9H-fluoren-9-ylmethoxy)carbonyl]-L-valyl-N-{4-[10-(biphenyl-4-yl)-4,7,10-trimethyl-3,8-dioxo-2,9-dioxa-4,7-diazaundec-1-yl]phenyl}N⁵-carbamoyl-L-ornithinamide 8,11-pentamethyl-3,9-dioxo-2, 10-dioxa-4,8-diazadodec-1-yl]phenyl}-N⁵-carbamoyl-L-ornithinamide was treated with dichloroacetic acid (7.8 mmol). The reaction mixture was stirred at room temperature, until no starting material was detectable, then purified by flash column chromatography

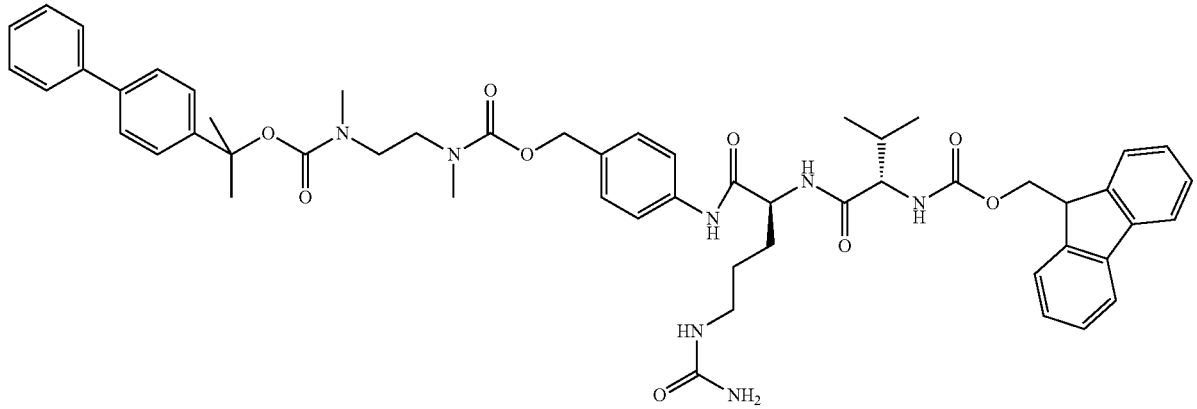 [SMILES: CC(C)[C@H](NC(=O)OCC1c2ccccc2-c2ccccc21)C(=O)N[C@@H](CCCNC(N)=O)C(=O)Nc1ccc(COC(=O)N(C)CCN(C)C(=O)OC(C)(C)c2ccc(-c3ccccc3)cc2)cc1]

MS (ESI): 954 (MH+)
¹H NMR (500 MHz, DMSO-d₆) δ ppm 0.86 (dd, J=13.34, 6.79 Hz, 6 H) 1.69 (br. s., 6 H) 1.86-2.05 (m, 1 H) 2.76 (m, J=9.30 Hz, 2 H) 2.92 (d, J=14.95 Hz, 3 H) 3.01 (m, J=6.10 Hz, 1 H) 3.15-3.15 (m, 0 H) 3.38-3.53 (m, 2 H) 3.93 (t, J=7.63 Hz, 1 H) 4.18-4.26 (m, 2 H) 4.26-4.34 (m, 1 H) 4.42 (br. s., 1 H) 4.92-5.06 (m, 2 H) 5.39 (s, 2 H) 5.96 (t, J=6.02 Hz, 1 H) 7.18-7.48 (m, 12 H) 7.52-7.66 (m, 6 H) 7.70-7.77 (m, 2 H) 7.88 (d, J=7.47 Hz, 2 H) 8.11 (br. s., 1 H) 10.06 (br. s., 1 H)

Step 5

The Title Intermediate

The crude product N-[6-(2,5-dioxo-2,5-dihydro-1H-pyrrol-1-yl)hexanoyl]-L-valyl-N-{4-[11-(biphenyl-4-yl)-4,6,6, (EtOH:CH₂Cl₂=1.5:8.5) on silica gel, affording the desired product (44.0 mg, white solid).
MS (ESI): 729 (MH+)
¹H NMR (500 MHz, METHANOL-d₄) δ ppm 0.97 (d, J=4.42 Hz, 3 H) 0.98 (d, J=4.27 Hz, 3 H) 1.04 (s, 6 H) 1.23-1.35 (m, 4 H) 1.50-1.68 (m, 7 H) 1.76 (dtd, J=13.90, 9.26, 9.26, 5.11 Hz, 1 H) 1.86-1.95 (m, 1 H) 2.07 (dq, J=13.90, 6.86 Hz, 1 H) 2.26-2.31 (m, 2 H) 2.57 (s, 3 H) 2.67 (s, 2 H) 3.04 (s, 3 H) 3.11 (dt, J=13.50, 6.67 Hz, 1 H) 3.16-3.22 (m, 1 H) 3.23 (br. s., 2 H) 3.48 (t, J=7.09 Hz, 2 H) 4.14 (d, J=7.47 Hz, 1 H) 4.49 (dd, J=9.07, 5.11 Hz, 1 H) 5.13 (s, 2 H) 5.94 (s, 3 H) 6.75-6.82 (m, 1 H) 7.36 (d, J=8.54 Hz, 2 H) 7.60 (d, J=8.69 Hz, 2 H).

Preparation of Intermediate

N-[6-(2,5-dioxo-2,5-dihydro-1H-pyrrol-1-yl)hexanoyl]-L-valyl-N⁵-carbamoyl-N-{4-[({methyl[2-(methylamino)ethyl]carbamoyloxy}methyl]phenyl}-L-ornithinamide

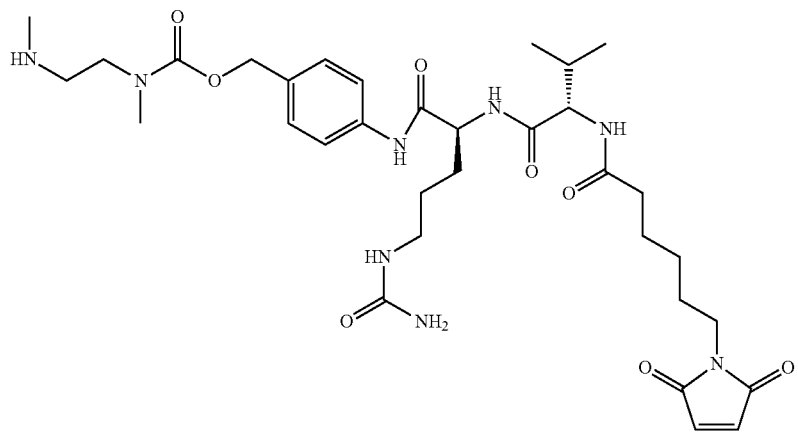 [SMILES: CNCCN(C)C(=O)OCc1ccc(NC(=O)[C@H](CCCNC(N)=O)NC(=O)[C@@H](NC(=O)CCCCCN2C(=O)C=CC2=O)C(C)C)cc1]

Step 6

N-[6-(2,5-dioxo-2,5-dihydro-1H-pyrrol-1-yl)
hexanoyl]-L-valyl-N-{4-[11-(biphenyl-4-yl)-4,6,6,8,
11-pentamethyl-3,9-dioxo-2,10-dioxa-4,8-diazado-
dec-1-yl]phenyl}-N⁵-carbamoyl-L-omithinamide To a solution of the crude product N-[6-2,5-dioxo-2,5-dihydro-1H-pyrrol-1-yl)hexanoyl]-L-valyl-N-{4-[11-(biphenyl-4-yl)-4,6,6,8,11-pentamethyl-3,9-dioxo-2,10-dioxa-4,8-diazadodec-1-yl]phenyl}-N⁵-carbamoyl-L-omithinamide (0.0629 mmol) in anhydrous dimethylformamide (1.5 ml), 1-{6-[(2,5-dioxopyrrolidin-1-

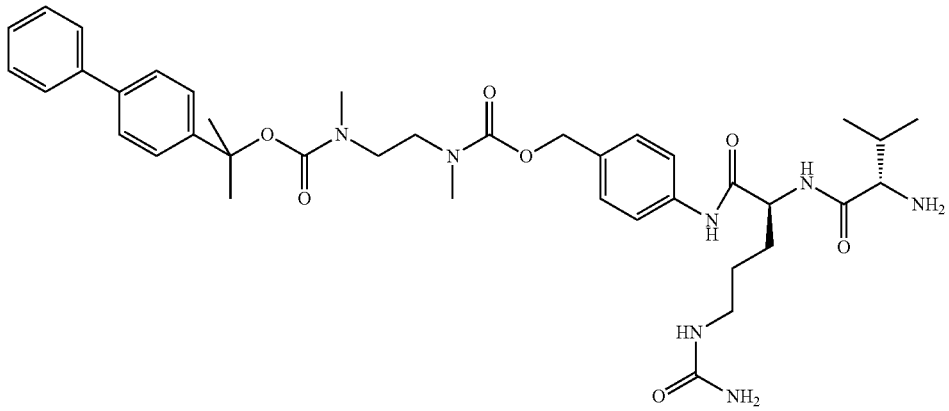 [SMILES: CC(C)[C@H](N)C(=O)N[C@@H](CCCNC(N)=O)C(=O)Nc1ccc(COC(=O)N(C)CCN(C)C(=O)OC(C)(C)c2ccc(-c3ccccc3)cc2)cc1]

To a solution of the product N-[(9H-fluoren-9-ylmethoxy)carbonyl]-L-val-N-{4-[10-(biphenyl-4-yl)-4,7,10-trimethyl-3,8-dioxo-2,9-dioxa-4,7-diazaundec-1yl]phenyl}-N⁵-carbamoyl-L-ornithinamide [prepared as reported above under step 4] (0.063 mmol, 60 mg) in anhydrous dimethylformamide (0.8 ml), piperidine (0.32 mmol, 27.2 mg) was added. The reaction mixture was stirred at room temperature until no starting material was detectable. The solvent was evaporated under vacuum and the crude thus obtained was used without further purification in the next step.

MS (ESI): 732 (MH+)

Step 7

N-[6-(2,5-dioxo-2,5-dihydro-1H-pyrrol-1-yl)
hexanoyl]-L-valyl-N-{4-[10-(biphenyl-4-yl)-4,7,10-
trimethyl-3,8-dioxo-2,9-dioxa-4,7-diazaundec-1-yl]
phenyl}-N⁵-carbamoyl-L-omithinamide yl)oxy]-6-oxohexyl}-1H-pyrrole-2,5-dione (0.189 mmol, 58.3 mg) and triethylamine (0.252 mmol, 25.5 mg) were added. The reaction mixture was stirred at room temperature until no starting material was detectable. The solvent was evaporated under vacuum and the crude was purified by flash column chromatography (eluant:EtOH:CH$_2$Cl$_2$=1:9) on silica gel (230-400 mesh), affording the desiderated product (34 mg, white wax)

MS (ESI): 925 (MH+)

¹H NMR (500 MHz, DMSO-d$_6$) δ ppm 0.83 (dd, J=15.79, 6.79 Hz, 6 H) 1.31-1.40 (m, 1 H) 1.60 (br. s., 1 H) 1.69 (s, 6 H) 1.90-2.02 (m, 1 H) 2.05-2.23 (m, 2 H) 2.89-2.96 (m, 3 H) 3.01 (br. s., 1 H) 3.34-3.38 (m, 2 H) 3.46 (m, J=8.24 Hz, 2 H) 4.19 (t, J=7.40 Hz, 1 H) 4.38 (br. s., 1 H) 4.95-5.05 (m, 2 H) 5.40 (s, 2 H) 5.97 (d, J=−12.20 Hz, 1 H) 6.98-7.02 (m, 2 H) 7.30 (d, J=8.85 Hz, 2 H) 7.37 (dd, J=15.40, 7.93 Hz,

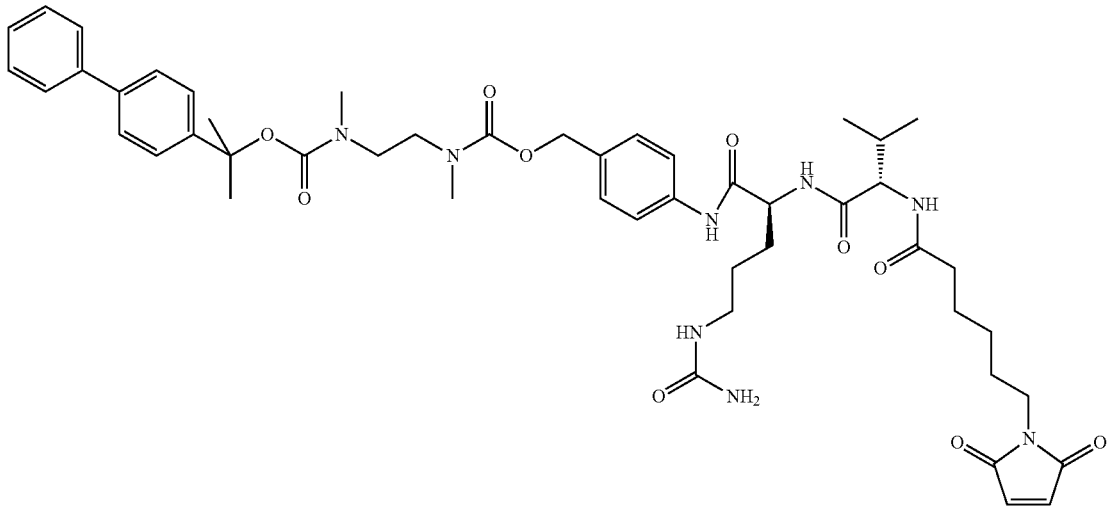 [SMILES: CC(C)[C@H](NC(=O)CCCCCN1C(=O)C=CC1=O)C(=O)N[C@@H](CCCNC(N)=O)C(=O)Nc1ccc(COC(=O)N(C)CCN(C)C(=O)OC(C)(C)c2ccc(-c3ccccc3)cc2)cc1]

3 H) 7.45 (m, J=7.17 Hz, 2 H) 7.52-7.67 (m, 6 H) 7.80 (d, J=8.24 Hz, 1 H) 8.08 (d, J=6.71 Hz, 1 H) 9.76-10.18 (m, 1 H)

Step 8

The Title Intermediate

Reacting the intermediate prepared under step 6 under reaction conditions reported above in step 5, the title compound as a white powder was obtained

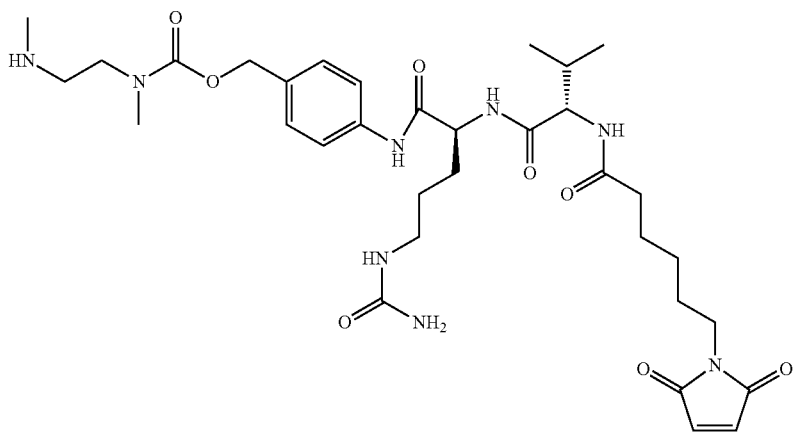 [SMILES: CNCCN(C)C(=O)OCc1ccc(NC(=O)[C@H](CCCNC(N)=O)NC(=O)[C@@H](NC(=O)CCCCCN2C(=O)C=CC2=O)C(C)C)cc1]

The invention claimed is:

1. A method for treating ovarian cancer, which comprises administering to a mammal in need thereof an effective amount of a compound of formula (II)

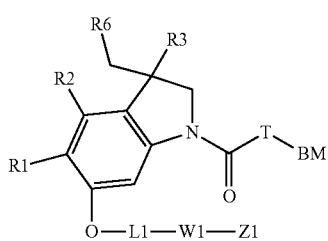

(II)

wherein R1 and R2 taken together form a group (D) or (G):

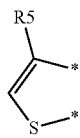

(D)

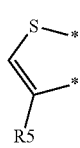

(G)

wherein R5 is hydrogen, linear or branched $C_1$-$C_4$ alkyl, linear or branched $C_1$-$C_4$ hydroxyalkyl or linear or branched $C_1$-$C_4$ aminoalkyl;

R3 and R4 are, each independently, hydrogen or a group selected from an optionally substituted linear or branched $C_1$-$C_4$ alkyl and linear or branched $C_1$-$C_4$ hydroxyalkyl;

R6 is a leaving group;

T is null or N;

BM of formula (V):

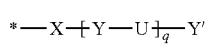

(V)

wherein:

X is null, linear or branched $C_1$-$C_4$ alkyl, linear or branched $C_2$-$C_4$ alkenyl or linear or branched $C_2$-$C_4$ alkynyl;

Y is an optionally substituted aryl or heteroaryl selected from the group consisting of

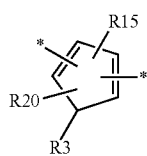

(XVa)

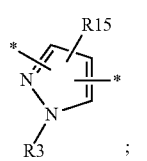

(XVb)

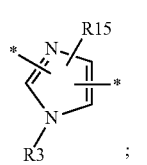

(XVc)

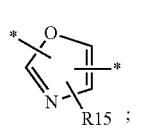

(XVd)

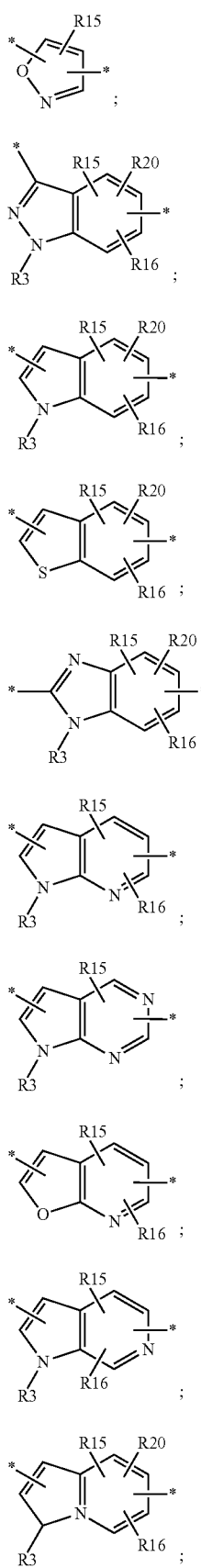
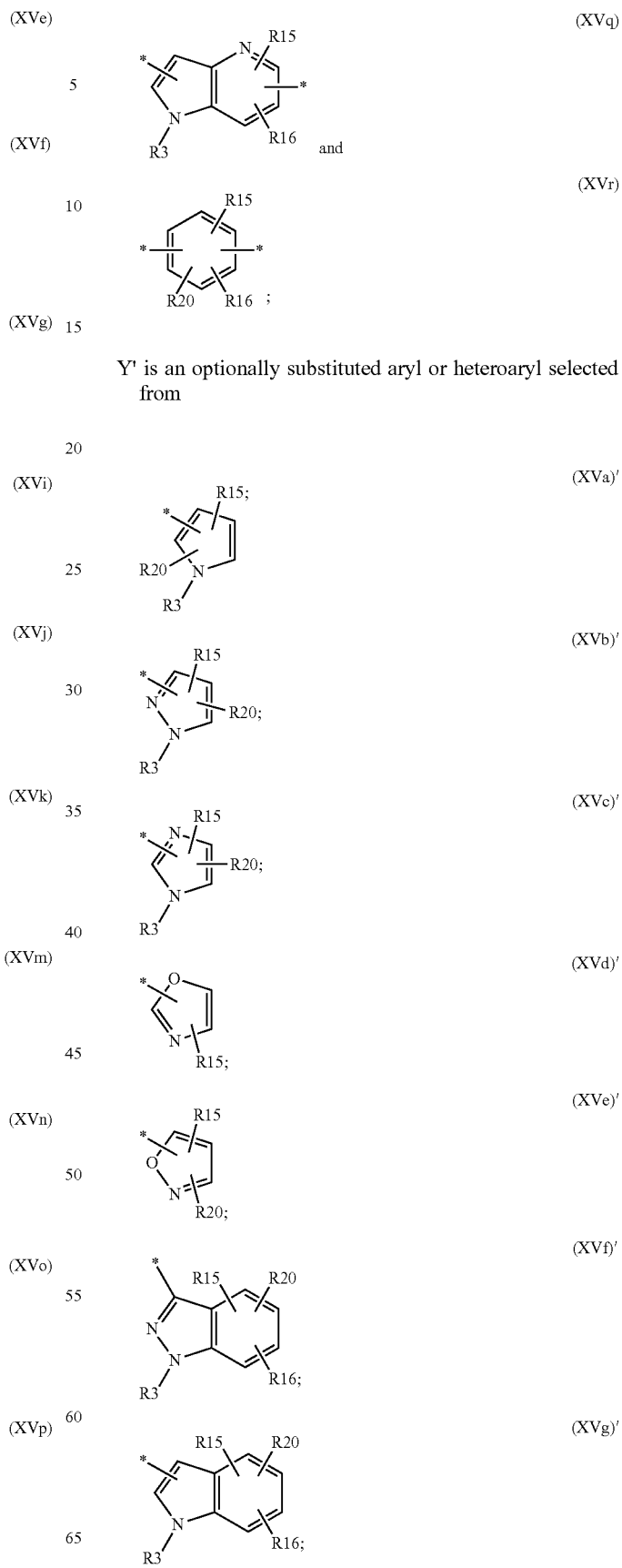
Y' is an optionally substituted aryl or heteroaryl selected from -continued

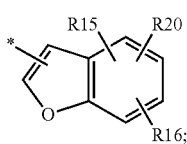
(XVh)'

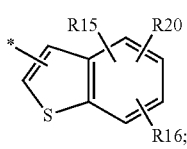
(XVi)'

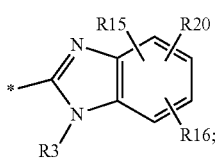
(XVj)'

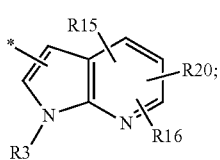
(XVk)'

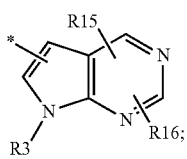
(XVm)'

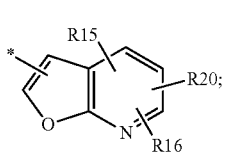
(XVn)'

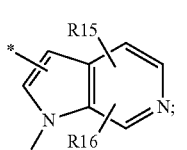
(XVo)'

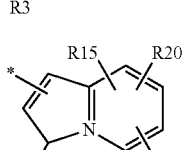
(XVp)'

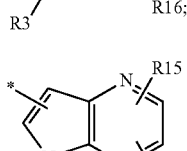
(XVq)'

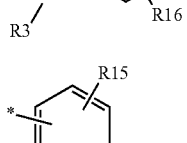
(XVr)'

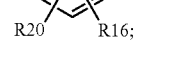

wherein R15, R16 and R20 are independently hydrogen, halogen, hydroxy, NO$_2$, an optionally substituted linear or branched C$_1$-C$_6$ alkyl or C$_1$-C$_6$ alkoxy, cyano,—COOH, —CONH—R3, —N—C(O)O—R3, —C(NH)—NH$_2$ or —NR3R4, and R3 and R4 are as defined above;

U is a moiety of formula (VI) or (VII):

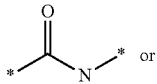
(VI)

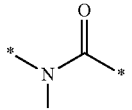
(VII)

wherein R3 is as defined above;

q is an integer from 0 to 4;

L1 is hydrogen or L, wherein L is null or a moiety selected from NHCO—R9 (Xa); —NHCONH—R9 (Xb); —NHCOO—R9 (Xc); —NH—R9 (Xd);

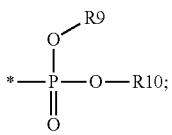
(Xe)

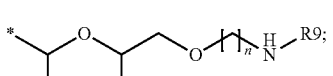
(Xf)

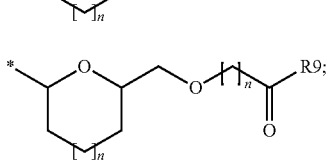
(Xg)

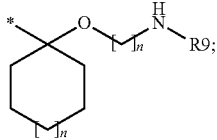
(Xh)

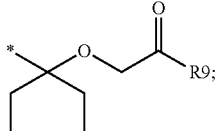
(Xi)

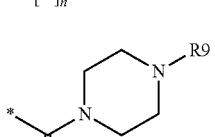
(Xj)

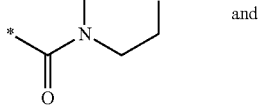
and

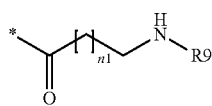 (Xk)

wherein
R9 and R10 are, each independently, hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl, when W1 and Z1 are null, or
R9 and R10 are null when at least one of W1 and Z1 is not null,
n is an integer from 0 to 2 and
n1 is an integer from 0 to 4;
W1 is null or a system comprising one or more groups independently selected from

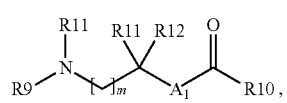 (XIa)

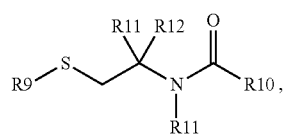 (XIb)

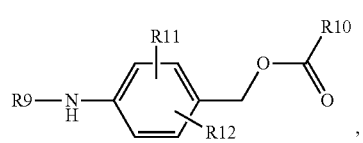 (XIc)

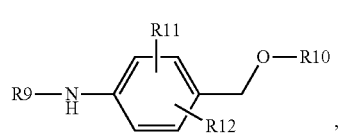 (XId)

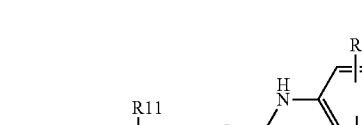 (XIe)

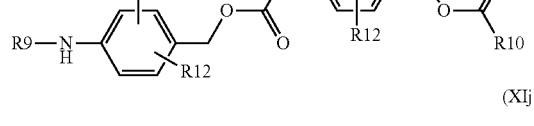 (XIj)

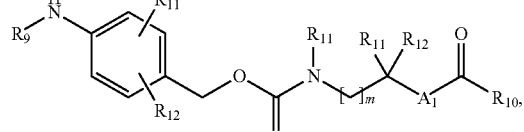 (XIf)

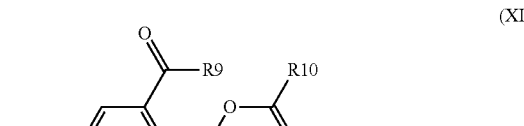

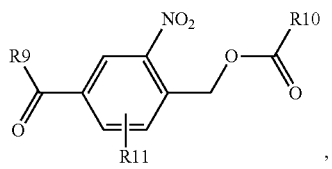 (XIg)

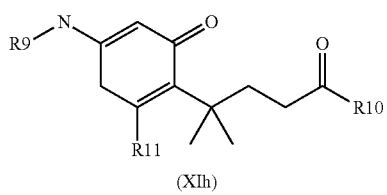 (XIh)

and (XIh)

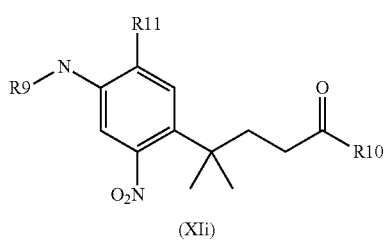 (XIi)

(XIi)

wherein
one of R9 and R10 is null and the other is as defined above,
R11 and R12 are, each independently, hydrogen, halogen, methyl, ethyl or linear or branched $C_1$-$C_4$ hydroxymethyl,
m is an integer from 0 to 3, and
$A_1$ is $CH_2$, $CH_2N$—R12 or N—R12, wherein R12 is as defined above;
Z1 is null or a peptidic linker ($Z_a$), a non peptidic linker ($Z_b$) or hybrid linker($Z_c$), wherein
$Z_a$ is selected from a single amino acid, a dipeptide, a tripeptide, a tetrapeptide and an oligopeptide moiety comprising natural L-amino acids, unnatural D-amino acids, synthetic amino acids or any combination thereof;
$Z_b$ is selected from

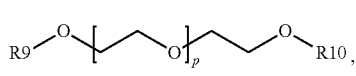 (XIIa)

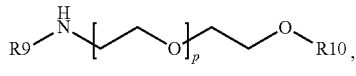 (XIIb)

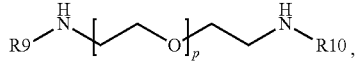 (XIIc)

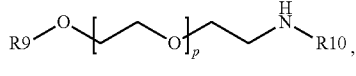 (XIId)

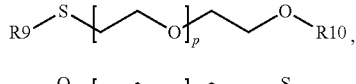 (XIIe)

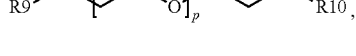 (XIIf)

-continued

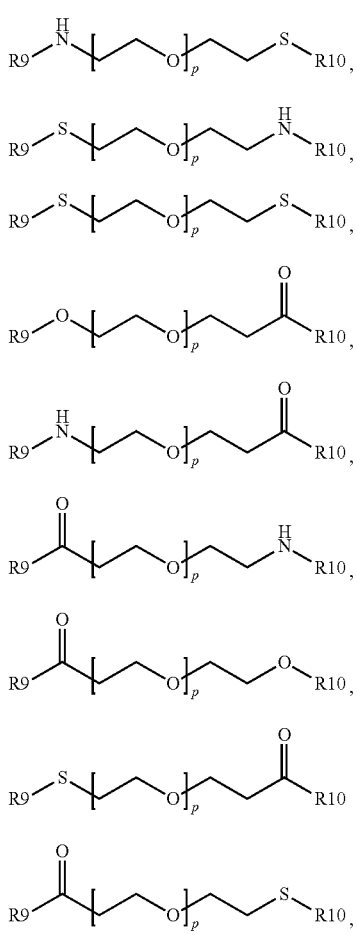

(XIIg)
(XIIh)
(XIIi)
(XIIj)
(XIIk)
(XIIm)
(XIIn)
(XIIo)
(XIIp)

wherein
one of R9 and R10 is null and the other is as defined above and p is an integer from 1 to 20; and
$Z_c$ is a group of formula $Z_a$—$Z_b$ or $Z_b$—$Z_a$ wherein $Z_a$ and $Z_b$ are as defined above;
provided that a compound of formula (II) wherein L1 is hydrogen is excluded when
1) both T and X are null, q is 0 and
Y' is an heterocyclyl moiety of formula (VIII), (VIII)' or (VIII)":

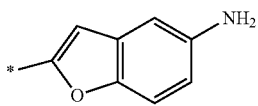

(VIII)

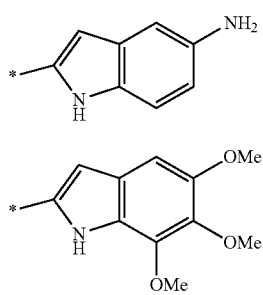

(VIII)'

-continued

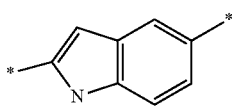

(VIII)"

or
2) both T and X are null, q is 1, U is a group of formula (VII),
Y is an heterocyclyl moiety of formula (IX)

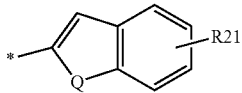

(IX)

and
Y' is an heterocyclyl moiety of formula (VIII)'''

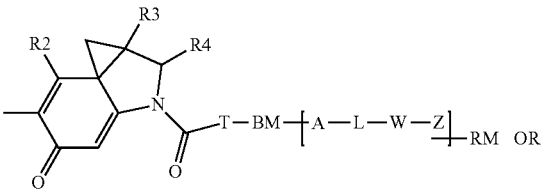

(VIII)''' wherein Q is —NH— or O, and R21 is hydrogen or a group selected from —N($C_2H_5$)$_2$ and —C(NH)NH$_2$;
with the proviso that in a compound of formula (II) when L1 is L, at least one among L, W1 and Z1 is not null;
or the pharmaceutically acceptable salts thereof,
or
a compound of formula (III) or (IV)

(III)

R1—[ring with R2, R3, R4, N]—C(O)—T—BM—[A—L—W—Z]—RM  OR (IV)

R1—[ring with R2, R6, R3, R4, N]—C(O)—T—BM—[A'—L—W—Z]—RM

O—[L1—W1—Z1]—RM1 wherein R1 and R2 taken together form a group (D) or (G):

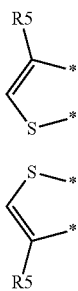 (D)

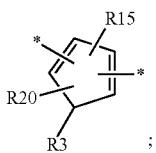 (G)

wherein R5 is hydrogen, linear or branched $C_1$-$C_4$ alkyl, linear or branched $C_1$-$C_4$ hydroxyalkyl or linear or branched $C_1$-$C_4$ aminoalkyl;
R3 and R4 are, each independently, hydrogen or a group selected from an optionally substituted linear or branched $C_1$-$C_4$ alkyl and linear or branched $C_1$-$C_4$ hydroxyalkyl;
R6 is a leaving group;
T is null or N;
BM is of formula (V)':

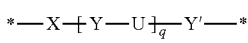 (V)' wherein:
X is null, linear or branched $C_1$-$C_4$ alkyl, linear or branched $C_2$-$C_4$ alkenyl or linear or branched $C_2$-$C_4$ alkynyl,
Y is an optionally substituted aryl or heteroaryl selected from the group consisting of

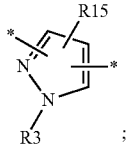 (XVa)

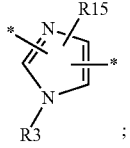 (XVb)

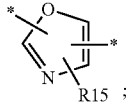 (XVc)

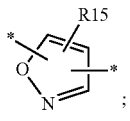 (XVd)

(XVe)

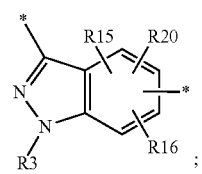 (XVf)

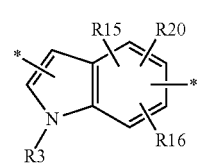 (XVg)

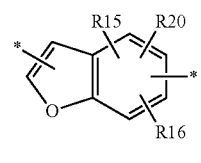 (XVh)

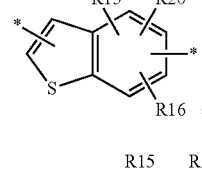 (XVi)

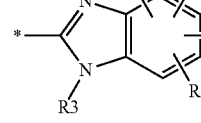 (XVj)

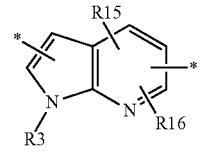 (XVk)

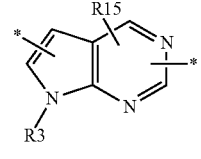 (XVm)

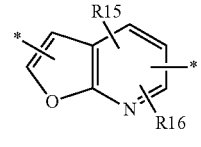 (XVn)

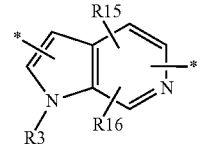 (XVo)

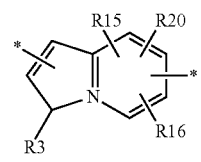 (XVp)

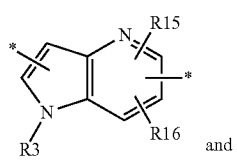 (XVq)
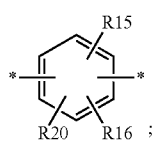 (XVr)
Y' is an optionally substituted aryl or heteroaryl selected from
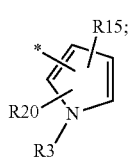 (XVa)'
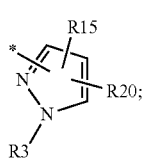 (XVb)'
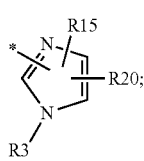 (XVc)'
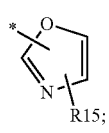 (XVd)'
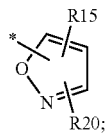 (XVe)'
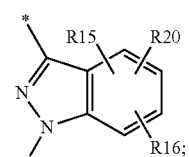 (XVf)'
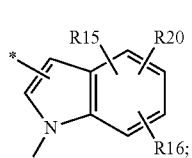 (XVg)'
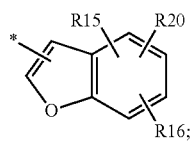 (XVh)'
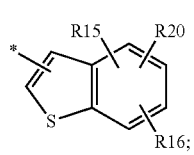 (XVi)'
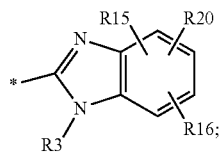 (XVj)'
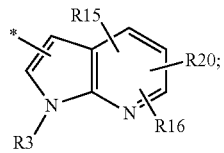 (XVk)'
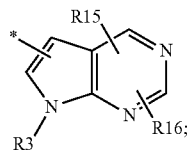 (XVm)'
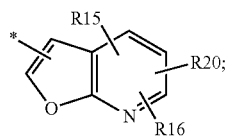 (XVn)'
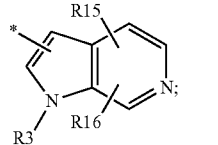 (XVo)'
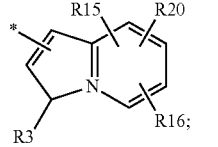 (XVp)'
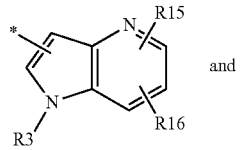 (XVq)' and
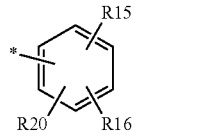 (XVr)'
wherein R15, R16 and R20 are independently hydrogen, halogen, hydroxy, NO$_2$, an optionally substituted linear or branched $C_1$-$C_6$ alkyl or $C_1$-$C_6$ alkoxy, cyano, —COOH, —CONH—R3, —N—C(O)O—R3, —C(NH)—NH$_2$ or —NR3R4, and R3 and R4 are as defined above, U is a moiety of formula (VI) or (VII)

(VI)

(VII)

wherein R3 is as defined above, and
q is an integer from 0 to 4;
A is an atom selected from —O—, —NH—, —CO—;
A' is null or A, wherein A is as defined above;
L is null or a moiety selected from NHCO—R9 (Xa); —NHCONH—R9 (Xb); —NHCOO—R9 (Xc); —NH—R9 (Xd);

(Xe)

(Xf)

(Xg)

(Xh)

(Xi)

(Xj)

(Xk)

wherein

R9 and R10 are, each independently, hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl, when W, Z and RM are null, or R9 and R10 are null when at least one of W, Z and RM is not null, n is an integer from 0 to 2 and
n1 is an integer from 0 to 4;
L1 is hydrogen or L, wherein L is as defined above;
W and W1 are independently null or a system comprising one or more groups independently selected from (XIa)

(XIb)

(XIc)

(XId)

(XIe)

(XIj)

-continued

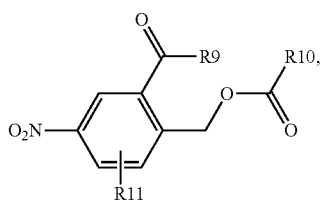 (XIf)

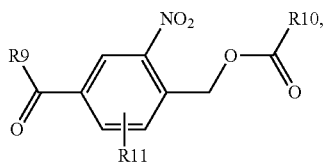 (XIg)

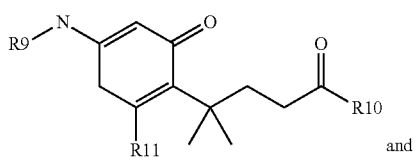 (XIh)

and

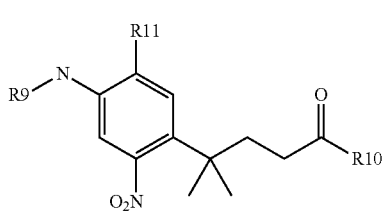 (XIi)

wherein
one of R9 and R10 is null and the other is as defined above,
R11 and R12 are, each independently, hydrogen, halogen, methyl, ethyl or linear or branched $C_1$-$C_4$ hydroxymethyl,
m is an integer from 0 to 3, and
$A_1$ is $CH_2$, $CH_2N$—R12 or N—R12, wherein R12 is as defined above;
Z and Z1 are independently null or a peptidic linker ($Z_a$), a non peptidic linker ($Z_b$) or a hybrid linker ($Z_c$), wherein
$Z_a$ is selected from a single amino acid, a dipeptide, a tripeptide, a tetrapeptide and an oligopeptide moiety comprising natural L-amino acids, unnatural D-amino acids, synthetic amino acids or any combination thereof;
$Z_b$ is selected from

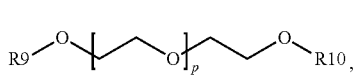 (XIIa)

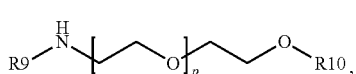 (XIIb)

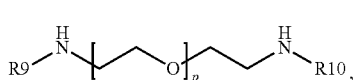 (XIIc)

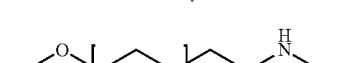 (XIId)

-continued

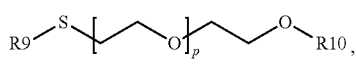 (XIIe)

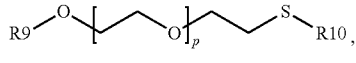 (XIIf)

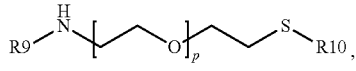 (XIIg)

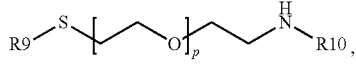 (XIIh)

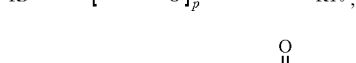 (XIIi)

 (XIIj)

 (XIIk)

 (XIIm)

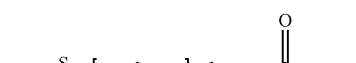 (XIIn)

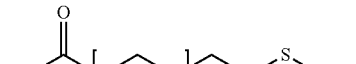 (XIIo)

, and

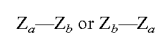 (XIIp)

wherein
one of R9 and R10 is null and the other is as defined above and p is an integer from 1 to 20; and
$Z_c$ is a group of formula $Z_a$—$Z_b$ or $Z_b$—$Z_a$ wherein $Z_a$ and $Z_b$ are as defined above;
RM and RM1 are independently null or a moiety selected from

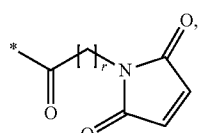 (XIIIa)

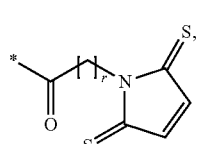 (XIIIb)

-continued (XIIIc)

(XIIId)

(XIIIe)

(XIIIf)

(XIIIg)

(XIIIh)

(XIIIi)

(XIIIj)

(XIIIk)

wherein R13 is $C_1$-$C_3$ alkyl or an electron-withdrawing group selected from the group consisting of $NO_2$ and CN;
r is an integer from 0 to 7; and R11 and R12 are as defined above, said RM being attached to one or more of A, L, W or Z groups and said
RM1 being attached to one or more of L1, W1 or Z1 groups;
provided that
1) a compound of formula (IV) is excluded when A' is null and RM1 is null;
2) a compound of formula (III) or (IV) is excluded when
a) both T and X are null, q is 0 and
Y' is an heterocyclyl moiety of formula (VIII)$^{IV}$ (VIII)$^{IV}$ wherein
Q is —O—, —S—, —NR14—, wherein R14 is hydrogen, $C_1$-$C_4$ alkyl or $C_1$-$C_4$ hydroxyalkyl;
Q1 is —CH= or —N=;
R7 and R8 are independently hydrogen, halogen, hydroxy, $C_1$-$C_4$ alkoxy, cyano, —NCOOR3, —C(NH)—$NH_2$ or —NR3R4, wherein R3 and R4 are as defined above;
or
b) both T and X are null, q is 1 or 2, U is a group of formula (VII),
Y is a heterocyclyl moiety of formula (IX)':

(IX)' and
Y' is a heterocyclyl moiety of formula (VIII)$^{IV}$ (VIII)$^{IV}$ wherein Q, Q1, R7 and R8 are as defined above;
with the proviso that when L1 is L, at least one among L, W1, Z1 and RM1 is not null;
and with the proviso that when A' is A, at least one among L, W, Z and RM is not null;
or the pharmaceutically acceptable salts thereof.

2. The method according to claim 1 wherein the mammal in need thereof is a human.

3. The method according to claim 1, wherein the compound of formula (II), (III) or (IV), as defined in claim 1, is selected from the group consisting of:
N-(6-{[(8S)-8-(chloromethyl)-4-hydroxy-1-methyl-7,8-dihydro-6H-thieno[3,2-e]indol-6-yl]carbonyl}-1H-indol-3-yl)-1H-indole-6-carboxamide,
N-(5-{[(8R)-8-(chloromethyl)-4-hydroxy-1-methyl-7,8-dihydro-6H-thieno[3,2-e]indol-6-yl]carbonyl}-1- methyl-1H-pyrrol-3-yl)-1-methyl-4-{[(1-methyl-4-nitro-1H-pyrrol-2-yl)carbonyl]amino}-1H-pyrrole-2-carboxamide,
(2E)-1-[(8R)-8-(chloromethyl)-4-hydroxy-1-methyl-7,8-dihydro-6H-thieno[3,2-e]indol-6-yl]-3-(1H-pyrrolo[2,3-b]pyridin-3-yl)prop-2-en-1-one,
(2E)-1-[(8S)-8-(chloromethyl)-4-hydroxy-1-methyl-7,8-dihydro-6H-thieno[3,2-e]indol-6-yl]-3-(1H-pyrrolo[2,3-b]pyridin-3-yl)prop-2-en-1-one,
(8R)—N-(5-{[5-({5-[(3-amino-3-oxopropyl)carbamoyl]-1-methyl-1H-pyrrol-3-yl}carbamoyl)-1-methyl-1H-pyrrol-3-yl]carbamoyl}-1-methyl-1H-pyrrol-3-yl)-8-(chloromethyl)-4-hydroxy-1-methyl-7,8-dihydro-6H-thieno[3,2-e]indole-6-carboxamide,
(8S)—N-(5-{[5-({5-[(3-amino-3-oxopropyl)carbamoyl]-1-methyl-1H-pyrrol-3-yl}carbamoyl)-1-methyl-1H-pyrrol-3-yl]carbamoyl}-1-methyl-1H-pyrrol-3-yl)-8-(chloromethyl)-4-hydroxy-1-methyl-7,8-dihydro-6H-thieno[3,2-e]indole-6-carboxamide,
N-(3-{(1E)-3-[(8S)-8-(chloromethyl)-4-hydroxy-1-methyl-7,8-dihydro-6H-thieno[3,2-e]indol-6-yl]-3-oxoprop-1-en-1-yl}-1H-pyrrolo[2,3-b]pyridin-5-yl)-1H-indole-2-carboxamide,
N-(3-{(1E)-3-[(8R)-8-(chloromethyl)-4-hydroxy-1-methyl-7,8-dihydro-6H-thieno[3,2-e]indol-6-yl]-3-oxoprop-1-en-1-yl}-1H-pyrrolo[2,3-b]pyridin-5-yl)-1H-indole-2-carboxamide,
N-(2-{[(8S)-8-(chloromethyl)-4-hydroxy-1-methyl-7,8-dihydro-6H-thieno[3,2-e]indol-6-yl]carbonyl}-1H-indol-5-yl)-5-[2-(pyrrolidin-1-yl)ethoxy]-1H-indole-2-carboxamide,
tert-butyl {2-[(2-{[(8S)-8-(chloromethyl)-4-hydroxy-1-methyl-7,8-dihydro-6H-thieno[3,2-e]indol-6-yl]carbonyl}-1H-indol-5-yl)carbamoyl]-1H-indol-5-yl}carbamate,
(8S)-6-({5-[({5-[(tert-butoxycarbonyl)amino]-1H-indol-2-yl}carbonyl)amino]-1H-indol-2-yl}carbonyl)-8-(chloromethyl)-1-methyl-7,8-dihydro-6H-thieno[3,2-e]indol-4-yl 4-methylpiperazine-1-carboxylate,
(8S)-6-[(5-{[(5-amino-1H-indol-2-yl)carbonyl]amino})-1H-indol-2-yl)carbonyl]-8-(chloromethyl)-1-methyl-7,8-dihydro-6H-thieno[3,2-e]indol-4-yl 4-methylpiperazine-1-carboxylate hydrochloride,
(8S)-8-chloromethyl)-6-({5-[(1H-indol-2-ylcarbonyl)amino]-1H-indol-2-yl}carbonyl)-1-methyl-7,8-dihydro-6H-thieno[3,2-e]indol-4-yl piperazine-1-carboxylate,
(8R)-6-({5-[({5-[(tert-butoxycarbonyl)amino]-1H-indol-2-yl}carbonyl)amino]-1H-indol-2-yl}carbonyl)-8-(chloromethyl)-1-methyl-7,8-dihydro-6H-thieno[3,2-e]indol-4-yl 4-methylpiperazine-1-carboxylate,
(8R)-6-[(5-1{[(5-amino-1H-indol-2-yl)carbonyl]amino}-1H-indol-2-yl)carbonyl]-8-(chloromethyl)-1-methyl-7,8-dihydro-6H-thieno[3,2-e]indol-4-yl 4-methylpiperazine-1-carboxylate hydrochloride,
(8S)-8-(chloromethyl)-1-methyl-6-[(5-{[(5-nitro-1H-indol-2-yl)carbonyl]amino}-1H-indol-2-yl)carbonyl]-7,8-dihydro-6H-thieno[3,2-e]indol-4-yl 4-methylpiperazine-1-carboxylate,
(8R)-8-(chloromethyl)-1-methyl-6-[(5-{[(5-nitro-1H-indol-2-yl)carbonyl]amino}-1H-indol-2-yl)carbonyl]-7,8-dihydro-6H-thieno[3,2-e]indol-4-yl 4-methylpiperazine-1-carboxylate,
(8S)-8-(chloromethyl)-6-[(5-{[(5-hydroxy-1H-indol-2-yl)carbonyl]amino})-1H-indol-2-yl)carbonyl]-1-methyl-7,8-dihydro-6H-thieno[3,2-e]indol-4-yl 4-methylpiperazine-1-carboxylate,
(8R)-8-(chloromethyl)-6-[(5-{[(5-hydroxy-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate,
N-[6-(2,5-dioxo-2,5-dihydro-1H-pyrrol-1-yl)hexanoyl]-L-valyl-N~5~-carbamoyl-N-[4-({[{3-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide,
N-[6-(2,5-dioxo-2,5-dihydro-1H-pyrrol-1-yl)hexanoyl]-L-valyl-N~5~-carbamoyl-N-[4-({[{3-[({[(8R)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide,
[(8S)-8-(chloromethyl)-4-hydroxy-1-methyl-7,8-dihydro-6H-thieno[3,2-e]indol-6-yl]{5-[2-(pyrrolidin-1-yl)ethoxy]-1H-indol-2-yl}methanone,
[(8R)-8-(chloromethyl)-4-hydroxy-1-methyl-7,8-dihydro-6H-thieno[3,2-e]indol-6-yl]{5-[2-(pyrrolidin-1-yl)ethoxy]-1H-indol-2-yl}methanone,
N-[6-(2,5-dioxo-2,5-dihydro-1H-pyrrol-1-yl)hexanoyl]-L-valyl-N$^5$-carbamoyl-N-[4-({[{3-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide,
N-[6-(2,5-dioxo-2,5-dihydro-1H-pyrrol-1-yl)hexanoyl]-L-valyl-N$^6$-carbamoyl-N-[4-({[{3-[[({[(8R)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-omithinamide,
N-[6-(2,5-dioxo-2,5-dihydro-1H-pyrrol-1-yl)hexanoyl]-L-valyl-N$^5$-carbamoyl-N-[4-(({[(3-{[({(8S)-8-(chloromethyl)-1-methyl-6-[(2E)-3-{5-[2-(pyrrolidin-1-yl)ethoxy]-1H-indol-2-yl}prop-2-enoyl]-7,8-dihydro-6H-thieno[3,2-e]indol-4-yl}oxy)carbonyl](methyl)amino}-2,2-dimethylpropyl)(methyl)carbamoyl]oxy}methyl)phenyl]-L-ornithinamide,
N-[6-(2,5-dioxo-2,5-dihydro-1H-pyrrol-1-yl)hexanoyl]-L-valyl-N$^5$-carbamoyl-N-[4-({[(3-{([({(8R)-8-(chloromethyl)-1-methyl-6-[(2E)-3-{5-[2-(pyrrolidin-1-yl)ethoxy]-1H-indol-2-yl}prop-2-enoyl]-7,8-dihydro-6H-thieno[3,2-e]indol-4-yl}oxy)carbonyl](methyl)amino}-2,2-dimethylpropyl)(methyl)carbamoyl]oxy}methyl)phenyl]-L-ornithinamide,
(2E)-1-[(8S)-8-(chloromethyl)-4-hydroxy-1-methyl-7,8-dihydro-6H-thieno[3,2-e]indol-6-yl]-3-(1H-indol-3-yl)prop-2-en-1-one,
N-(2-{[(8R)-8-(chloromethyl)-4-hydroxy-1-methyl-7,8-dihydro-6H-thieno[3,2-e]indol-6-yl]carbonyl}-1-methyl-1H-indol-5-yl)-1-methyl-1H-indole-2-carboxamide,
N-[6-(2,5-dioxo-2,5-dihydro-1H-pyrrol-1-yl)hexanoyl]-L-phenylalanyl-L-leucyl-N-[4-({[{3-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]

oxy}carbonyl)(methyl)amino]-2,2-dimethylpropyl}(methyl)carbamoyl]oxy}methyl)phenyl]glycinamide, N-[6-(2,5-dioxo-2,5-dihydro-1H-pyrrol-1-yl)hexanoyl]-L-phenylalanyl-L-leucyl-N-[4-({[{3-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]glycinamide, N-[6-(2,5-dioxo-2,5-dihydro-1H-pyrrol-1-yl)hexanoyl]-L-phenylalanyl-L-leucyl-N-[4-({-[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]glycinamide, N-[6-(2,5-dioxo-2,5-dihydro-1H-pyrrol-1-yl)hexanoyl]-L-phenylalanyl-L-leucyl-N-[4-({[{2-[({[(8S)-8-(chloromethyl)-1-methyl-6-({5-[2-pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methy)carbamoyl]oxy}methy)phenyl]glycinamide, L-valyl-$N^5$-carbamoyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide, L-valyl-$N^5$-carbamoyl-N-[4-({[{2-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide, N-[6-(2,5-dioxo-2,5-dihydro-1H-pyrrol-1-yl)hexanoyl]-L-valyl-$N^5$-carbamoyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide, N-[19-(2,5-dioxo-2,5-dihydro-1H-pyrrol-1-yl)-17-oxo-, 7,10,13-tetraoxa-16-azanonadecan-1-oyl]-L-valyl-$N^5$-carbamoyl-N-[4-({[{2-[({[(8S)-8-(chloromethyl)-1-methyl-1-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-omithinamide and N-[6-(2,5-dioxo-2,5-dihydro-1H-pyrrol-1-yl)hexanoyl]-L-valyl-$N^5$-carbamoyl-N-[4-({[{2-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)methyl)amino]ethyl}(methyl)carbamoyl]oxy}methyl)phenyl]-L-ornithinamide.

\* \* \* \* \*